Figure 1A:
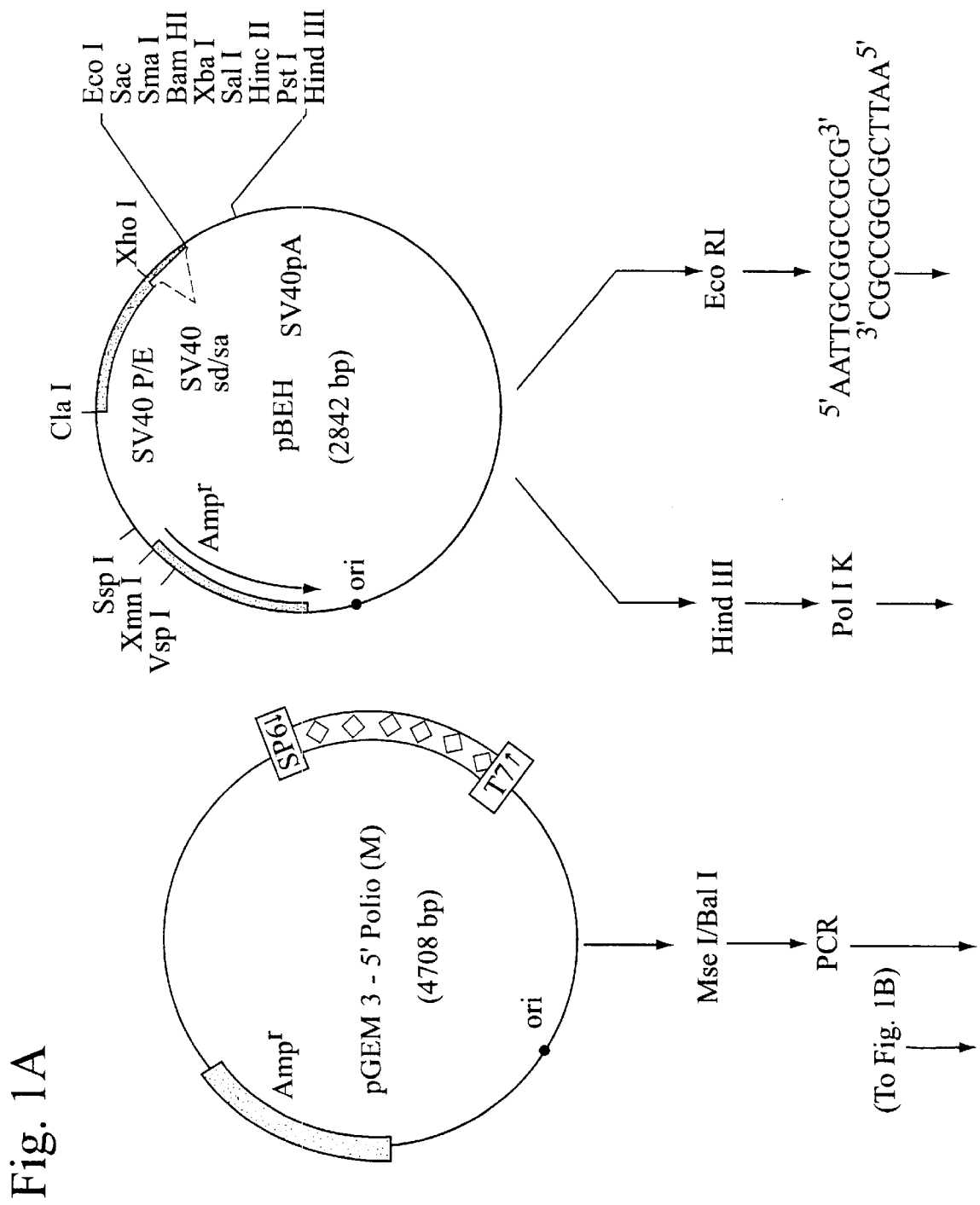

United States Patent [19]
Dirks et al.

[11] Patent Number: 6,060,273
[45] Date of Patent: *May 9, 2000

[54] MULTICISTRONIC EXPRESSION UNITS AND THEIR USE

[75] Inventors: Wilhelm Dirks, Braunschweig; Manfred Wirth, Wolfenbuttel; Hansjörg Hauser, Braunschweig; Wolfram Eichner, Hamburg; Volker Achterberg, Hamburg; Albrecht Dorschner, Hamburg; Wolfgang Meyer-Ingold, Hamburg; Heiko Mielke, Neu Wulmstorf, all of Germany

[73] Assignees: Beiersdorf AG, Hamburg; Gesellschaft fur Biotechnologische Forschung mbH, Braunschweig, both of Germany

[*] Notice: This patent is subject to a terminal disclaimer.

[21] Appl. No.: 08/867,352

[22] Filed: Jun. 2, 1997

Related U.S. Application Data

[63] Continuation of application No. 08/387,347, filed as application No. PCT/EP93/02294, Aug. 26, 1993, abandoned.

[30] Foreign Application Priority Data

Aug. 27, 1992 [DE] Germany .............................. 42 28 468

[51] Int. Cl.$^7$ .................................................. C12N 15/00
[52] U.S. Cl. ..................... 435/69.1; 435/320.1; 435/325; 435/252.3
[58] Field of Search ................................ 435/69.1, 172.3, 435/320.1, 325; 536/23.1, 23.72, 24.1

[56] References Cited

U.S. PATENT DOCUMENTS 5,665,567  9/1997  Eichner et al. .

FOREIGN PATENT DOCUMENTS

| | | |
|---|---|---|
| 0259 632 | 3/1988 | European Pat. Off. . |
| WO 90/01550 | 2/1990 | WIPO . |
| WO 90/08163 | 7/1990 | WIPO . |
| WO 93/03143 | 2/1993 | WIPO . |

OTHER PUBLICATIONS

Ostman et al., "Synthesis and Assembly of a Functionally Active recombinant Platelet–Derived Growth Factor AB Heterodimer", J. Biol. Chem. vol. 263, No. 31, Nov. 5, 1988, pp. 16202–16208.
Hart et al., "Purification of PDGF–AB and PDGF–BB from Human Platelet Extracts and Identification of all Three PDGF Dimers in Human Platelets", Biochemistry, vol. 29, No. 1, Jan. 9, 1990, pp. 166–172.
Falcone et al., "Both the 5' Untranslated region and the Sequences Surrounding the Start Site Contribute to Efficient Initiation of Translation in Vitro", Mol. Cell. Biol. vol. 11, No. 5, May 1991, p. 2662–2663.
Hammacher et al., "A Major Part of Platelet–Derived Growth Factor Purified from Human Platelets is a Heterodimer of one A and one B Chain", J. Biol. Chem. vol. 263, No. 31, Nov. 5, 1988, pp. 16493–16498.

Jackson et al., "The Novel Mechanism of Initiation of Picornavirus RNA Translation", Trends in Biochemical Science vol. 15, No. 12, Dec. 1990, pp. 477–483.
Kaufman et al., "Improved Vectors for Stable Expression of Foreign Genes in Mammalian Cells by Use of The Untranslated Leader Sequence from EMC Virus", Nucl. Acid Res. vol. 19, No. 16, Aug. 25, 1991, pp. 4485–4490.
Gossen et al., "Tight control of gene expression in mammalian cells by tetracycline–responsive promoters", Proc. Natl. Acad. Sci. USA 89:5547–5551 (1992).
Ptashne, Mark, "How eucaryotic transcriptional activators work", Nature 335:683–689 (1988).
Lieber et al, "High level gene expression in mammalian cells by a nuclear T7–phage RNA polymerase", Nucleic Acids Research 17(21):8485–8493 (1989).
Swanson et al, Production of Functional Human Hemoglobin in Transgenic Swine, Bio/Technology 10: 557 (1992).
Iizuka et al, Construction of Less Neurovirulent Polioviruses by Introducing Deletions into the 5' Noncoding Sequence of the Genome, J. Virology 63: 5354 (1989).
Kühn et al, Functional Analysis of the Internal Translation Initiation Site of Foot–and–Mouth Disease Virus, J. Virology 64: 4625 (1990).
Beck et al, Structure of the FMDV Translation Initiation Site of the Structural proteins, Nucleic Acids Research, 11 # 22 (1983).
Jang et al, Cap–Independent Translation of encephalomyocarditis virus RNA: Structural Elements of the Internal Ribosomal Entry Site and Involvement of a cellular 57–kDRNA–binding Protein, Genes & Development 4:1560 (1990).
Dirks & Hauser, in Animal Cell Technology: Products for Today and Prospects for Tomorrow eds Spier et al (Butterworth pub.) Equimolar Expression of Two Protein Chains in Recombinant Mammalian Cells pp 610–617.
Jang et al, A Segment of the 5' Nontranslated Region of Encephalomyocarditis Virus RNA Directs Internal Entry of Ribosomes During In Vitro Translations, J. Virology 62: 2636 (1988).
Dirks et al, Bicistronic Transcription Units for Gene Expression in Mammalian Cells. Gene 128: 247 (1993).
Shipley et al, Differential Effects of Epidermal Growth Factor, Transforming Growth Factor, and Insulin on DNA and Protein Synthesis and Morphology in Serum Free Cultures of AKR–2B Cells, Can. Res. 44: 710 (1984).
Macejak et al, Internal Initiation of Translation Mediated by the 5' leader of a cellular mRNA, Nature 353: 90 (1991).
Jackson et al, A Novel mechanism of Initiation of Picornavirus RNA Translation, TIBS Dec. 1990 p. 477–483.
Wilmut et al, Nature 385:810 (1997), Viable Offspring derived from fetal and adult mammalian cells.
Klon–Schaf mit menschlichen Genen geboren Jul. 25, 1997.
Palmiter et al. Ann Rev. Genetics 20: 465 (1986) Germ Line Transformation of Mice.

*Primary Examiner*—Marianne P. Allen
*Attorney, Agent, or Firm*—Nixon & Vanderhye P.C.

[57] ABSTRACT

Multicistronic expression units allow the equimolar expression of the genes located in the corresponding cistrons. These expression units are particularly suitable for the recombinant production of proteins composed of two or more polypeptide subunits.

17 Claims, 23 Drawing Sheets

Figures 1, 2A:
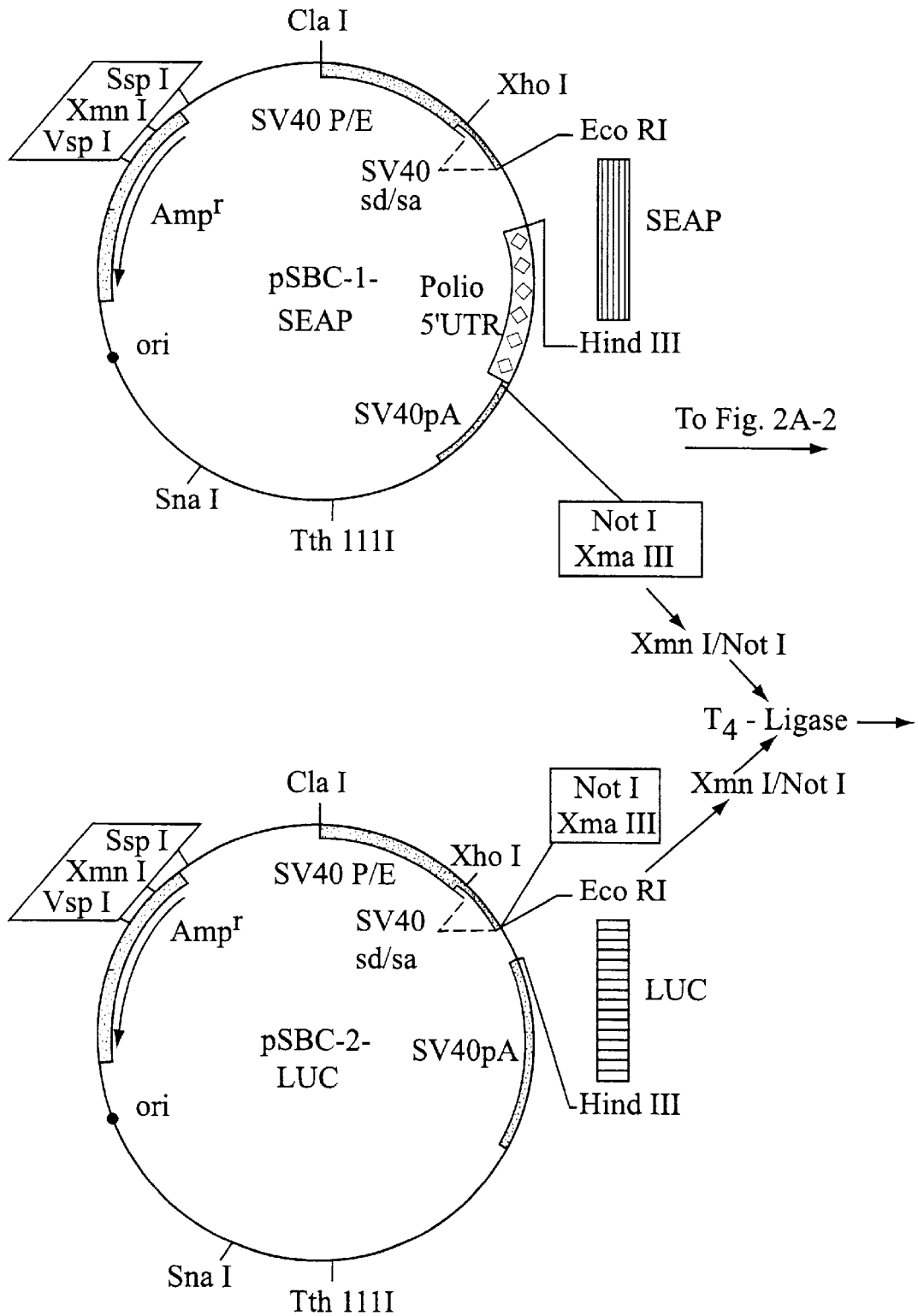
Figures 2, 2A:
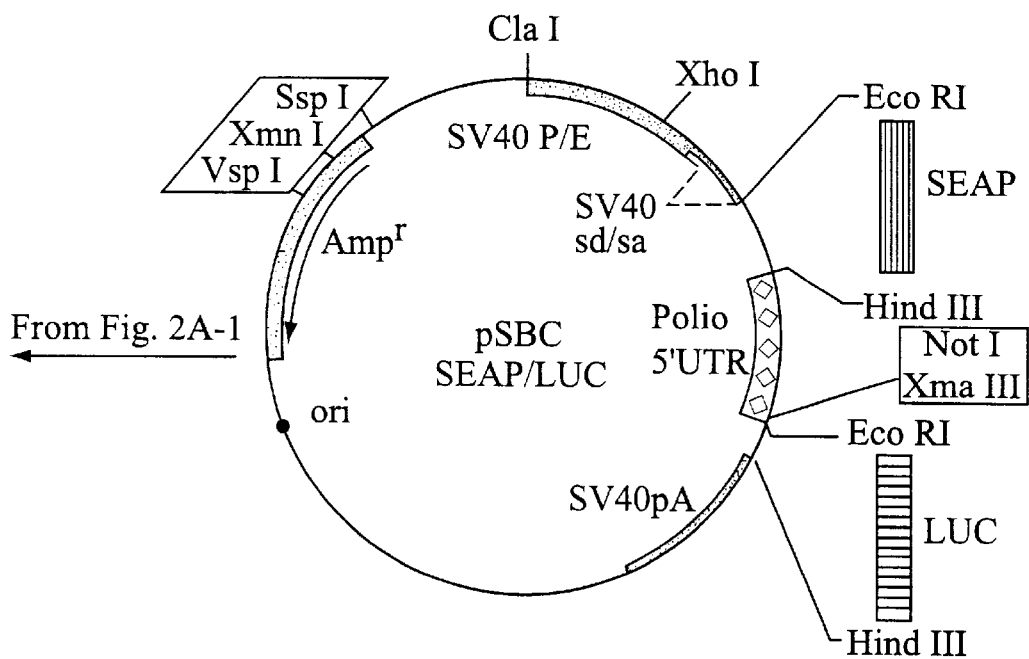
Figures 1, 2B:
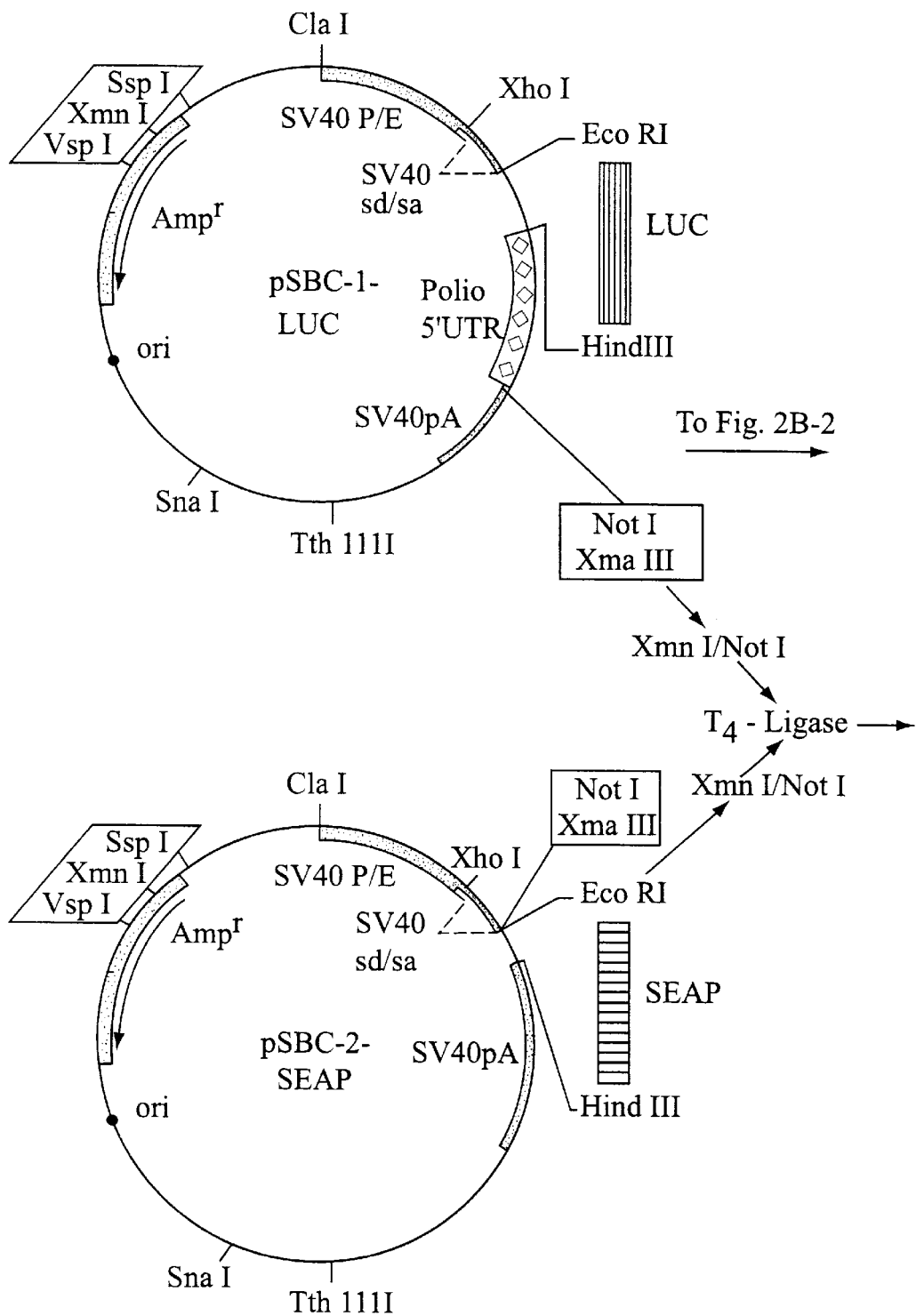
Figures 2, 2B:
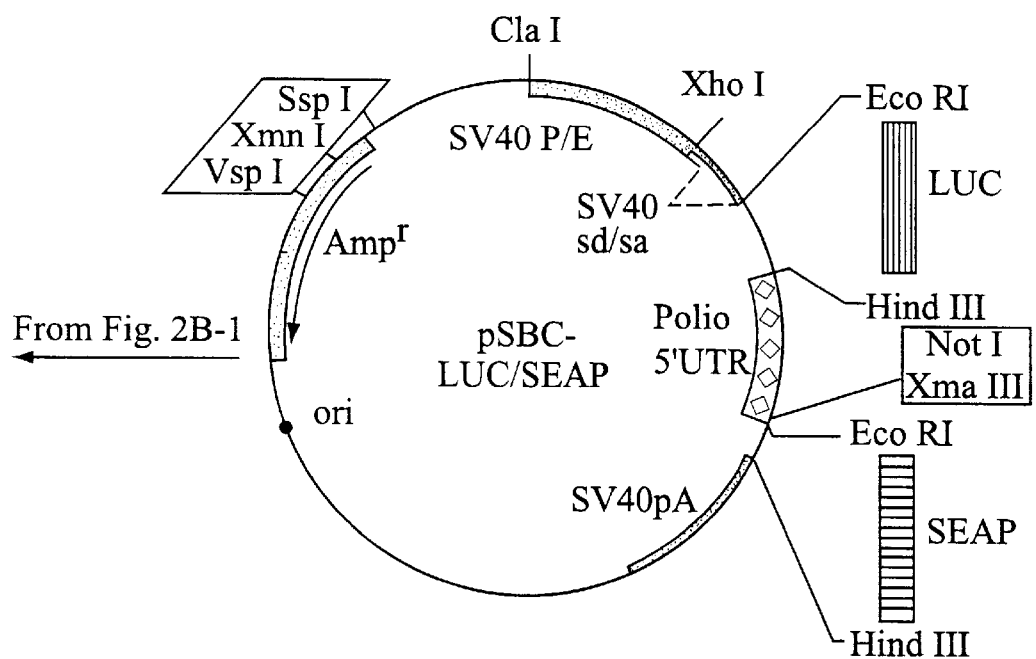
Figure 2C:
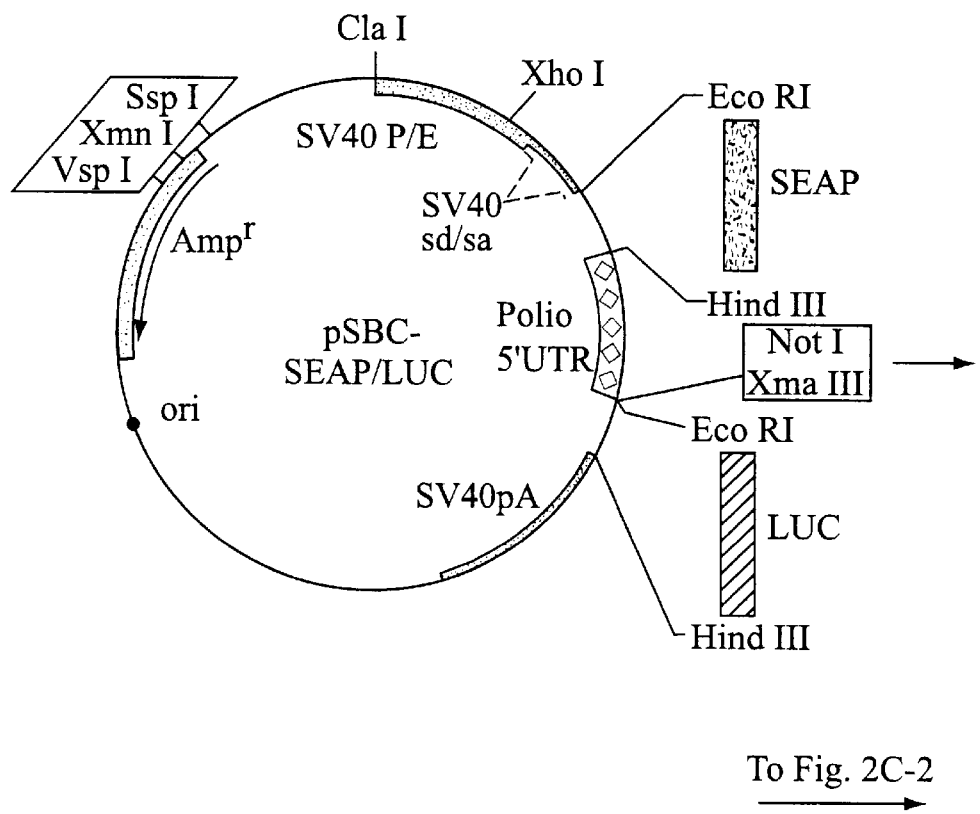
Figure 1:
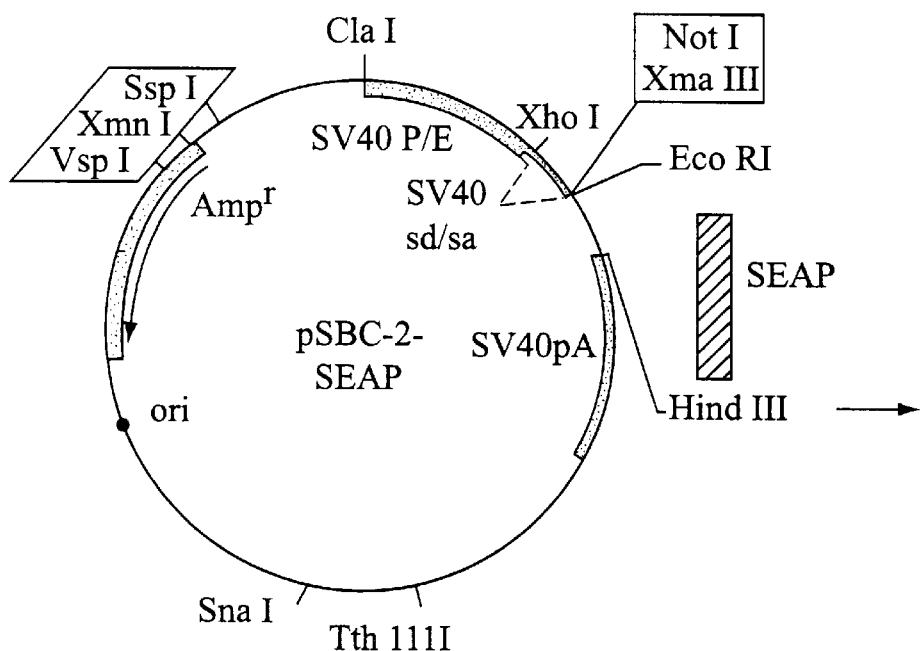
Figures 2, 2C:
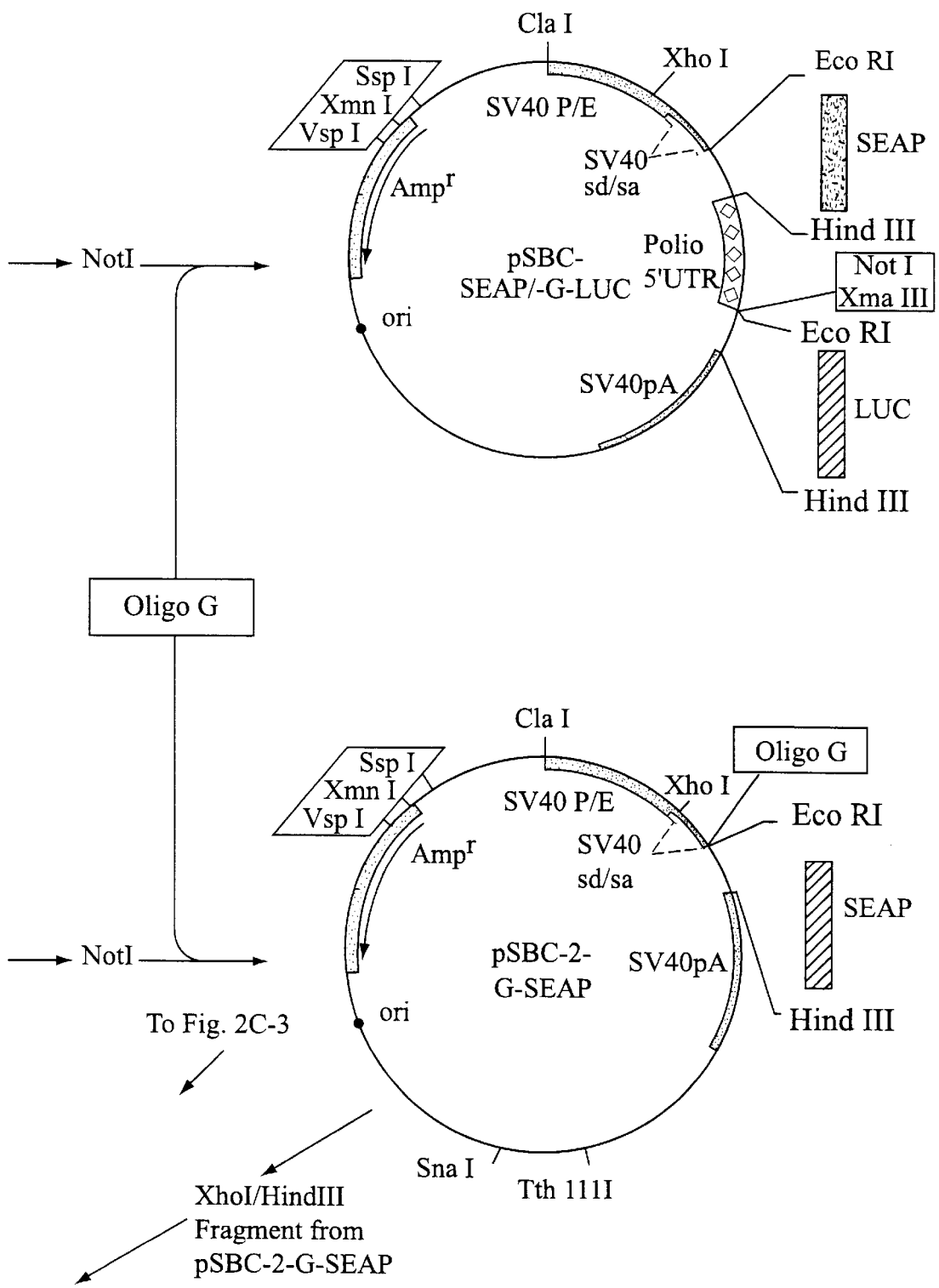

To Fig. 2C-2

Mutagenesis of PDGF - B

Figures 1, 6A:
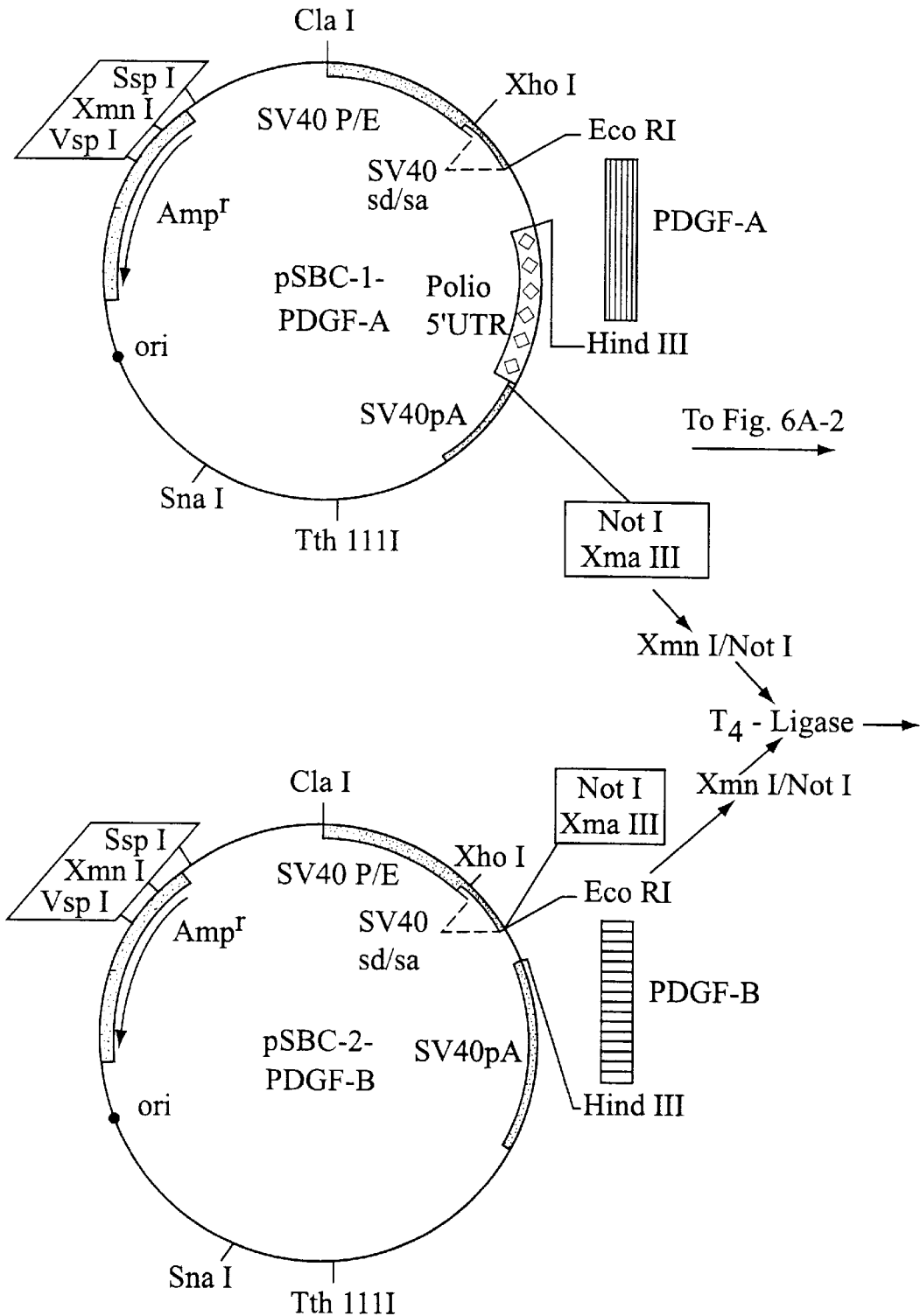
Figures 2, 6A:
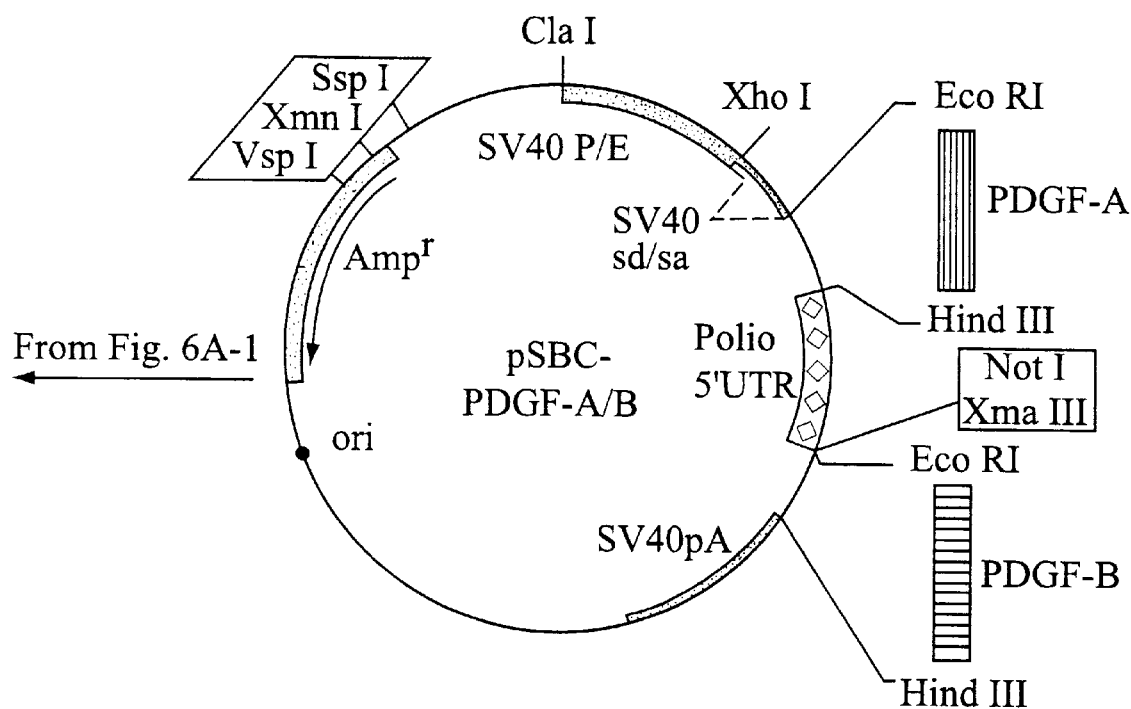
Figures 1, 6B:
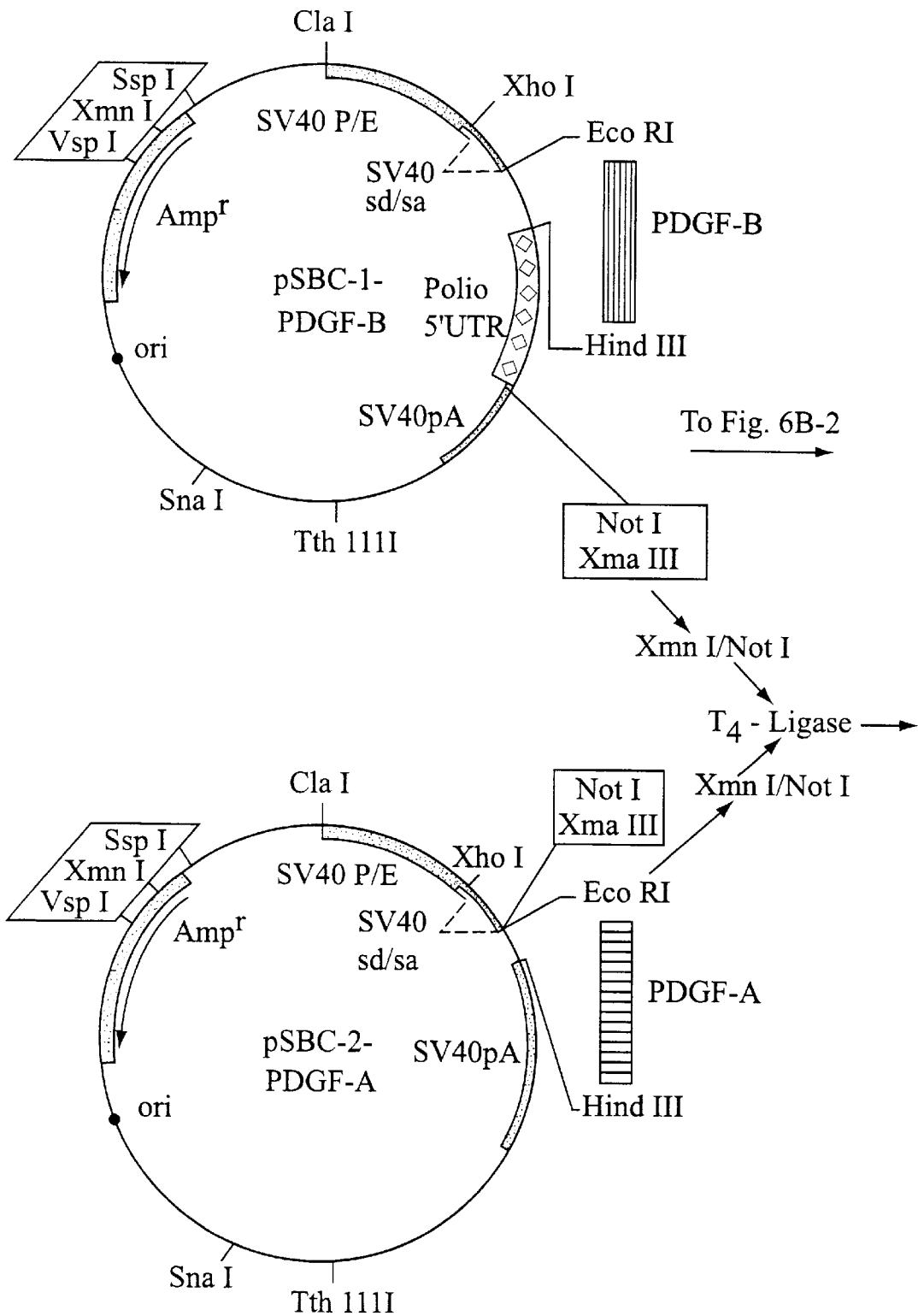
Figures 2, 6B:
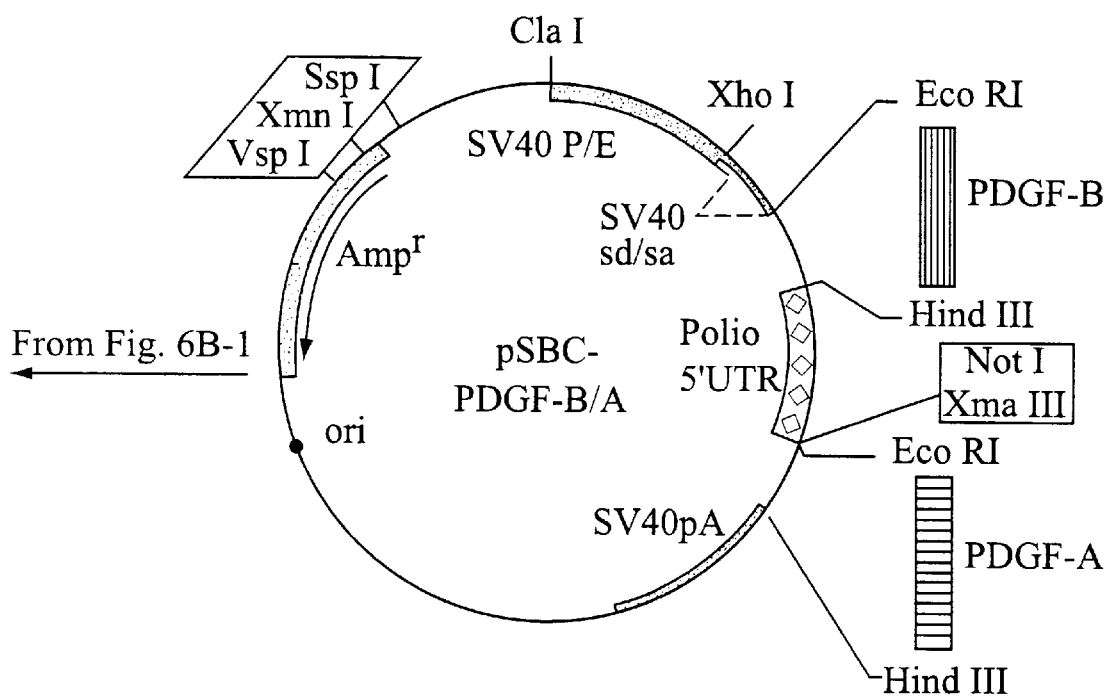
Figure 6C:
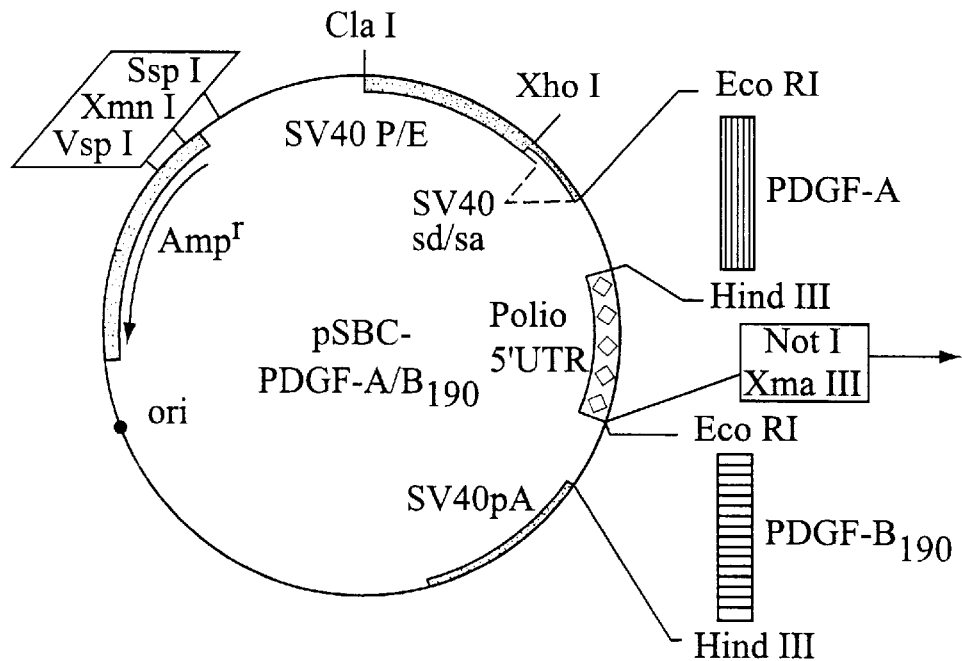
Figure 1:
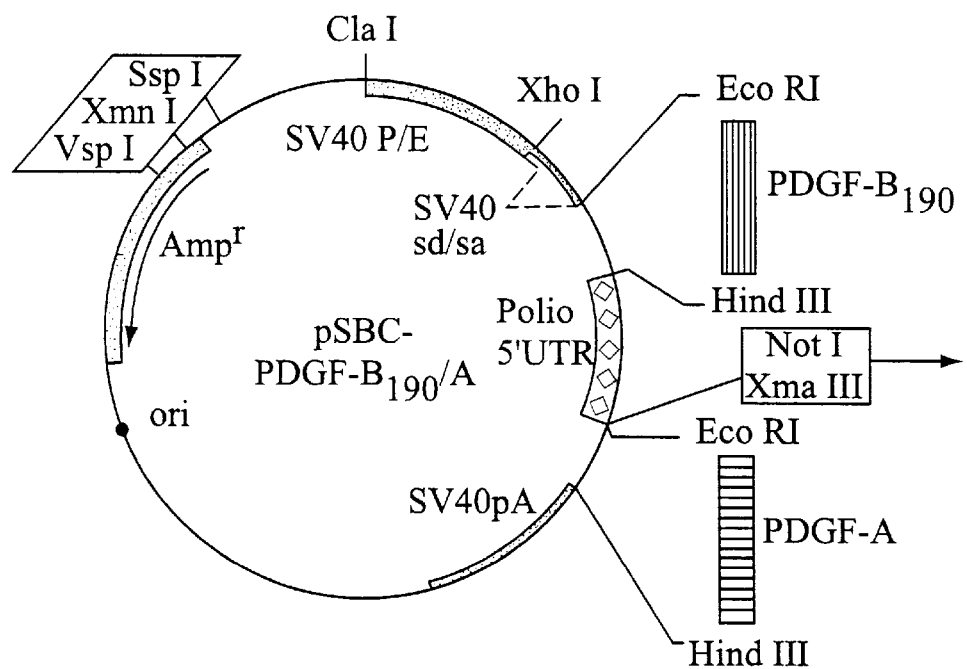
Figures 2, 6C:
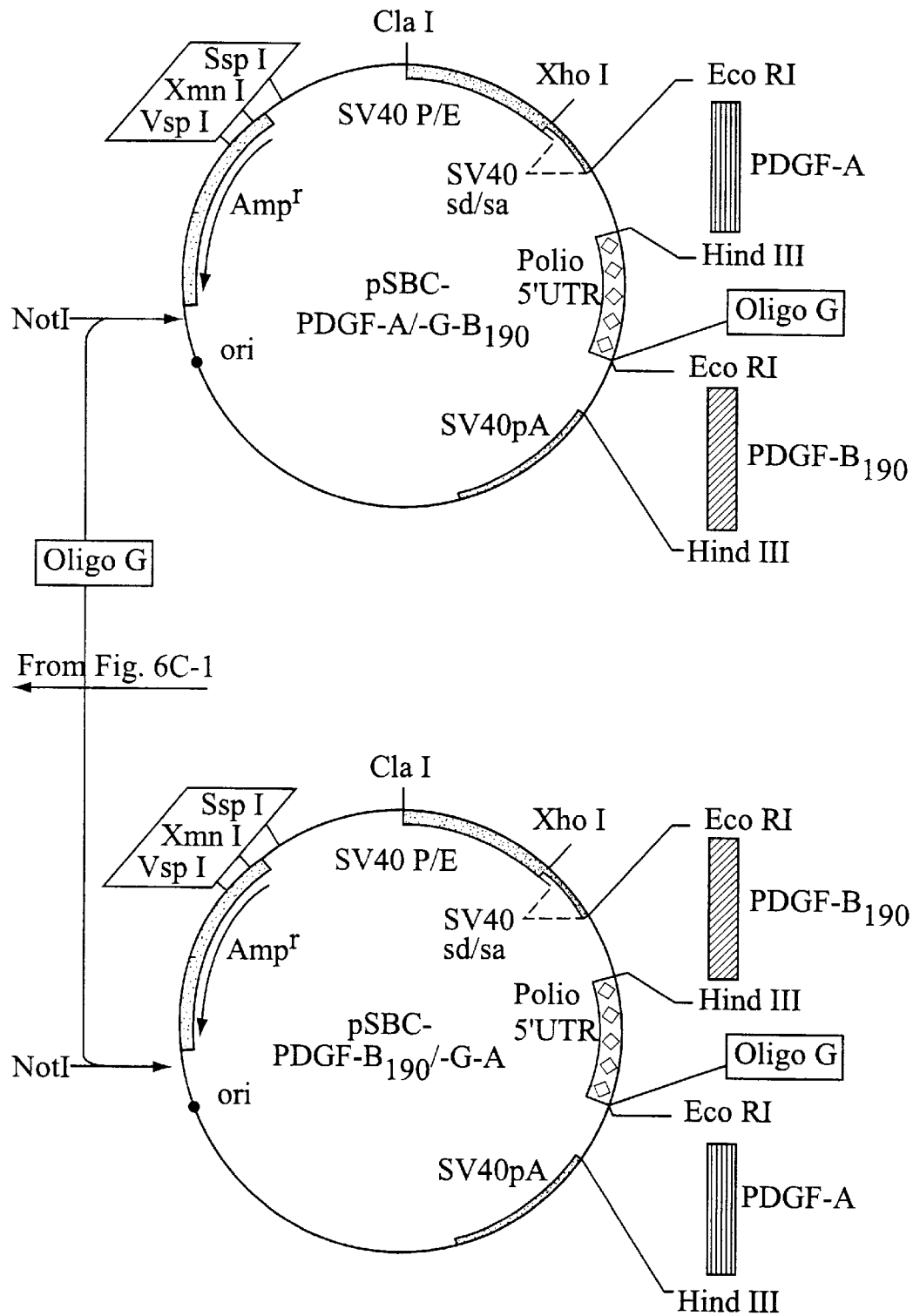

To Fig. 6C-2

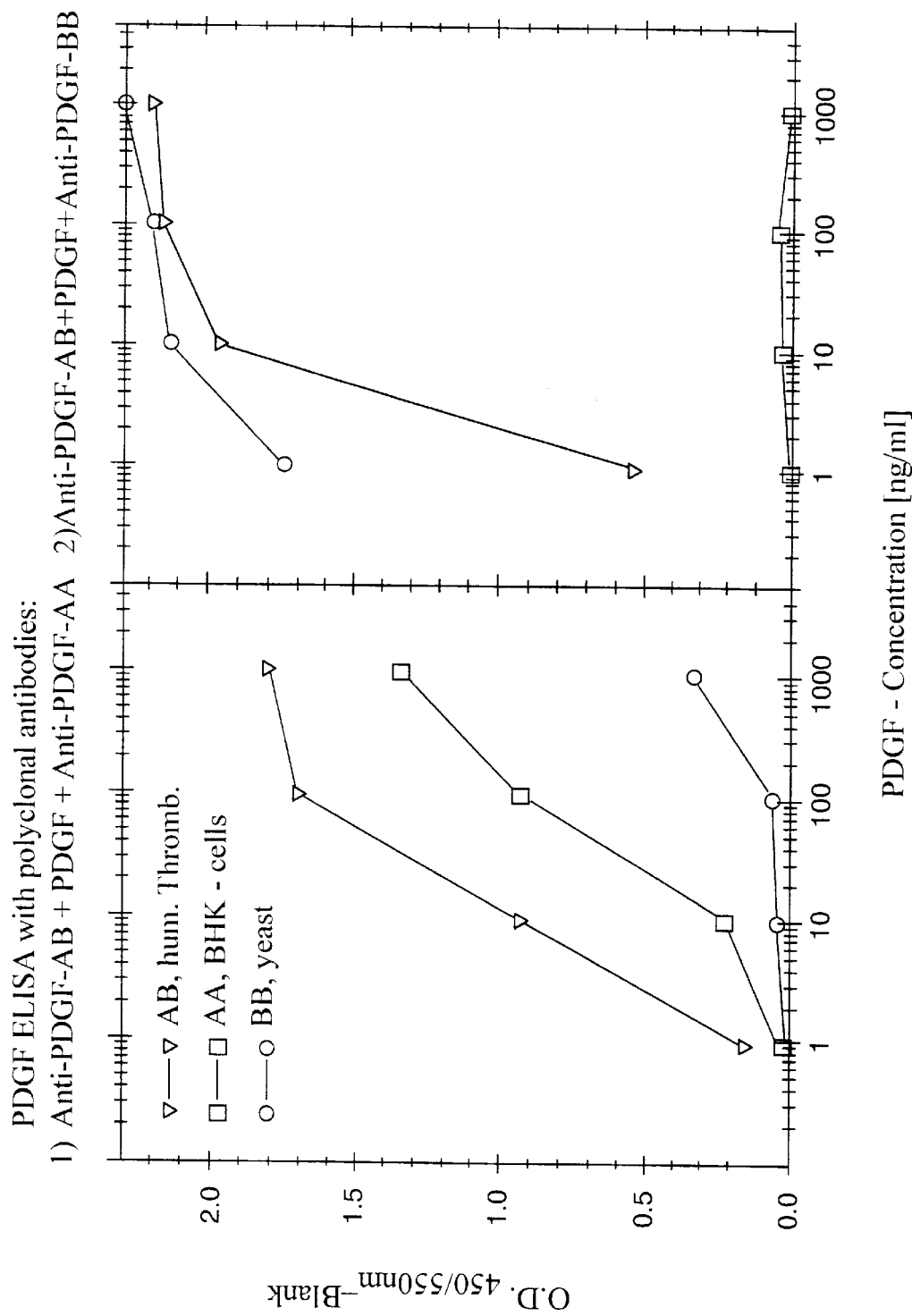

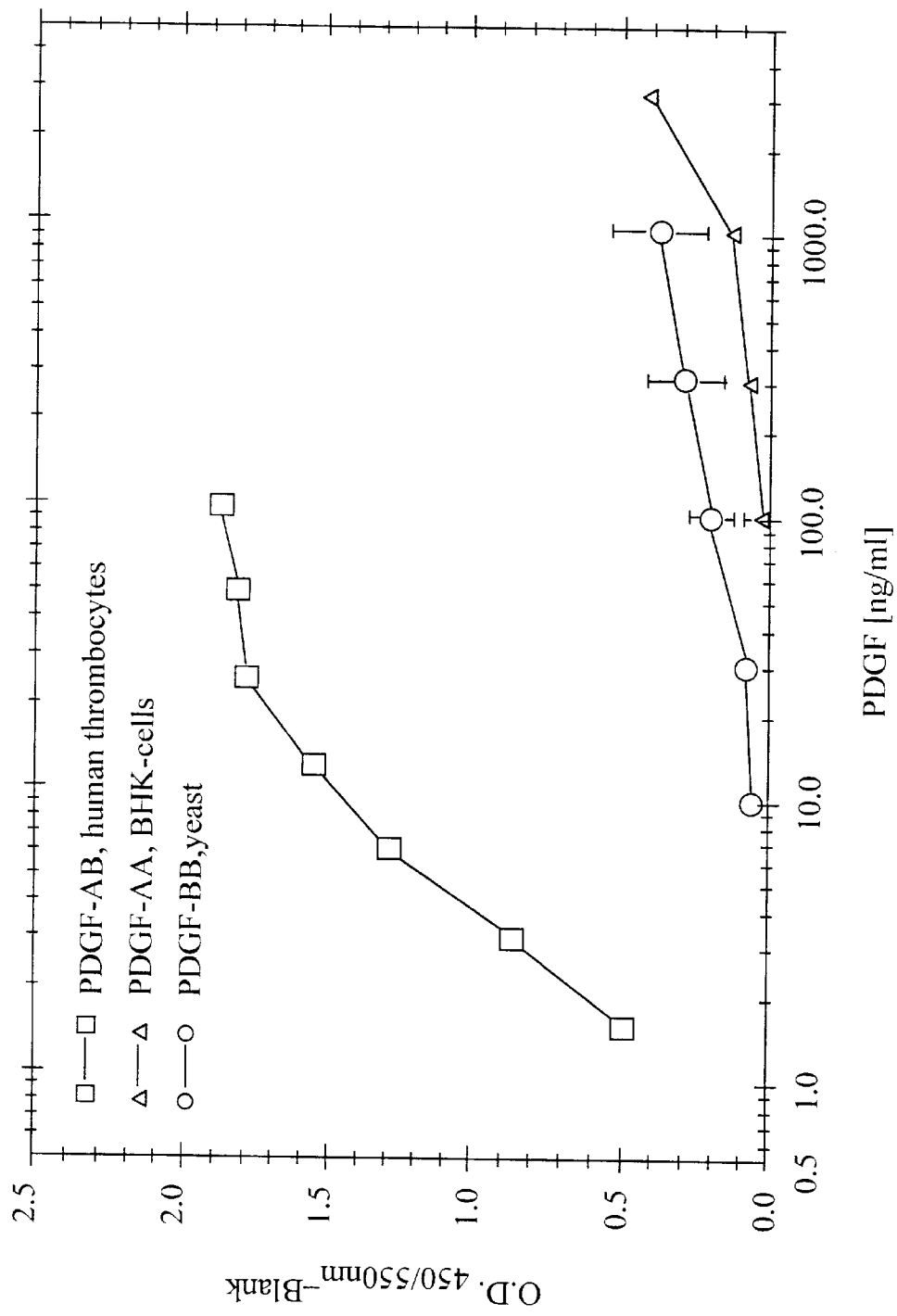

MULTICISTRONIC EXPRESSION UNITS AND THEIR USE

This is a continuation of application Ser. No. 08/387,347, filed Apr. 17, 1995, now abandoned, which was the national stage of International Application PCT/EP93/02294, filed Aug. 26, 1993.

The invention relates to multicistronic expression units and their use for the equimolar expression of polypeptides and subunits thereof in mammalian cells as host cells.

It has been possible for a long time now to prepare individual proteins, whose genes have been isolated by cloning, in various prokaryotic and eukaryotic cells following manipulation and gene transfer. Correct folding and processing and, where appropriate, post-translational modification as well, all of which are often not correctly carried out in prokaryotic and lower eukaryotic expression systems, are necessary for achieving the complete biological activity of many proteins. For this reason, mammalian cells are frequently used as hosts. Besides this, mammalian cells are able to secrete large quantities of proteins.

For various reasons, the simultaneous preparation of two or more protein chains is often required. For example, many natural proteins are, in their functional form, composed of several subunits (e.g. antibodies). In nature, the association of the different subunits of complex proteins takes place after protein synthesis. Other components of the cellular apparatus frequently participate in this association as catalysts or controlling elements, occasionally resulting in folding of the original structures. Interference with the association, e.g. as a consequence of unequal synthesis of the individual components, can have negative consequences both for the proteins which are to be formed and for the host cell. In nature, this system is subject to sophisticated regulation, which is for the most part cell-specific. Since this regulation is in general not adjustable in genetically manipulated cells, the alternatives explained below for simultaneously producing several foreign proteins have been developed and applied:

1) The genes are integrated separately into expression vectors and then cotransferred in an appropriate ratio into the cells. This presupposes that several plasmid copies are simultaneously taken up in a stable manner and continue to be harboured following division. The ratio of the expression of the different genes to each other depends both on the copy number and on the site of integration in the genome of the host cell. By means of elaborate screening processes, it is possible to isolate cell clones which express the individual gene products in the desired ratio.

2) In order to level out the copy number, the different genes are located on a vector in independent transcription units. While this to a large extent ensures stoichiometric representation of the genes, this process too is subject to problems. Thus, even if expression units possessing promoters of equal strength are used, this in no way ensures that the mRNAs, which encode the different proteins, possess the same stability and translation efficiency. Neither does the transcription efficiency of the two genes necessarily need to be identical. In this case, the stoichiometry of the expression is established step-wise with the aid of recombinant DNA stratagems (positioning of the transcription units in relation to each other, and modulation of the strength of the individual promoters by removing or adding individual elements).

3) To avoid the problems associated with the stability of the mRNA of different transcripts, bicistronic or multicistronic vectors were developed. For this purpose, the individual reading frames of the gene segments—cistrons—encoding the protein chains lie on one transcription unit (expression unit). Expression of the multicistronic gene is effected by way of a single promoter. While, in such vectors, translation of the first cistron is normally very efficient, that of the subsequent cistrons depends on the intercistronic sequences. If normal 5' untranslated sequences (5'UTR) from monocistronic genes are used for these intercistronic sequences, the expression of the subsequent cistron is normally very low (as a rule, about 0.5 to 2% of the translation of the first cistron, Kaufman et al., 1987; Boel et al., 1987). It was possible initially to increase this efficiency to about 20% by inserting leader sequences (high efficiency leaders, HEL). Following the discovery and use of particular cellular and viral sequences which allow the possibility of internal translation initiation (IRES: Jackson et al., 1990), it became possible to achieve a translation ratio between the first and subsequent cistron of 3:1.

Translation plays the key role in using bicistronic or multicistronic vectors. Normally, translation is initiated in eukaryotes by the "cap"-dependent mechanism, in the course of which a pre-initiation complex consisting of proteins and RNA is constructed at the 5' end of an mRNA possessing a "cap" (methylated nucleotide). From this point, a suitable translation initiation codon is selected, starting from which the translation is begun. It is believed that this takes place by way of a "scanning" process, with the pre-initiation complex moving along the mRNA in the 3' direction. Apart from a few exceptions, the cistron lying at the 5' end is always efficiently translated in this manner (Kozak, 1989). All the subsequent cistrons are either very inefficiently translated or not translated at all. It was possible to improve the translation efficiency of the subsequent cistrons by optimizing the distance between the genes (intercistronic regions; Kozak, 1987, Wirth et al., 1991) or by using so-called "high-efficiency leader" sequences (HEL, see above) (e.g. Falcone and Andrews, 1991 and reference therein). HEL's are those 5' untranslated regions of genes, or of other sequences as well, which stimulate the initiation of "cap"-dependent translation. Even in such constructs, however, the expression values which are achievable for the second and subsequent cistrons are always clearly lower than those of the first cistron which is regulated in a "cap"-dependent manner.

A mechanism, which was discovered in recent years, for initiating translation internally, i.e. starting the translation at an mRNA without "cap" structure, makes use of specific nucleic acid sequences. These sequences include the untranslated regions of individual picorna viruses, e.g. polio virus and encephalomyo-carditis virus, (Pelletier and Sonenberg, 1988; Jang et al., 1988; Jang et al., 1989) as well as some cellular proteins, e.g. Bid (Macejak and Sarnow, 1991). In the picorna viruses, a short segment of the 5' untranslated region, the so-called IRES (internal ribosomal entry site), is responsible for the internal binding of a pre-initiation complex. A region of 628 nt is necessary for efficiently initiating this translation. Investigations have shown that not only the 400 base pairs of the 3' region of the IRES, but also the extreme 5' part of the picorna-virus untranslated region, are necessary for efficient translation (Simoes and Sarnow, 1991). On the other hand, the "capping", which is the prerequisite for the normal mechanism of initiating translation, leads to a reduction in the efficiency of internal initiation by polio-virus IRES, if it is localized at the 5' end of a corresponding mRNA (Hambidge and Sarnow, 1991). The negative effect is abolished if the IRES is responsible for initiating the second cistron, that is if a cistron is situated between the "cap" and the IRES.

IRES elements can thus function as initiators of the efficient translation of reading frames. In doing this, they have no influence on the "cap"-dependent translation of the first cistron. Furthermore, conversely, an effect on IRES-dependent initiation appears to be independent of "cap"-dependent translation initiation. The mechanisms of the two processes also clearly differ in the use of different cellular factors (Meerovitch et al., 1989; Jang and Wimmer, 1990). In the past, several investigations have been published in which bicistronic expression plasmids were used (Adam et al., 1991; Ghattas et al., 1991; Kaufman et al., 1991; Wood et al., 1991; Wirth et al., 1991). However, since "cap"-dependent translation is clearly stronger than IRES-dependent translation, it was not possible to achieve stoichiometric expression of two protein chains. Previous applications have therefore concentrated on using selective markers in the second cistron. The close coupling of the expression of the selective marker with the gene to be expressed, which constitutes the first cistron, is particularly advantageous when selecting for a high level of expression, in particular if prior gene amplification is required. However, the synthesis of equimolar quantities of protein by bicistronic or multi-cistronic expression vectors has not previously been achieved.

A typical example of the potential importance of the equimolar expression of two different protein chains in recombinant preparation processes is the isolation by genetic manipulation of platelet-derived growth factor (PDGF), one of the main mitogens in human blood serum. PDGF purified from human blood platelets consists of two different, but closely related, polypeptide chains which are linked to each other by disulphide bridges. Under reducing conditions, the dimeric PDGF disassociates into its monomeric subunits, of which the larger ($M_r$ 15–17,000 D) is designated the PDGF-A chain and the smaller ($M_r$ 14,000 D) the PDGF-B chain (Johnsson et al., 1984).

The PDGF-A and PDGF-B protein chains are encoded by different genes. It has been possible to elucidate the complete structure of both gene products by means of cDNA cloning (Ratner et al., 1985, Betsholtz et al., 1986). In this context, it emerged that both PDGF molecules are initially synthesized as unusually long precursor molecules and are subsequently processed intracellularly to give rise to the mature PDGF chains. Two different PDGF-A transcripts, which differ by the presence or absence of a 69-bp segment in the 3' region, can be explained on the basis of alternative splicing (Betsholtz et al., 1986; Wise et al., 1989). This insert gives rise to a change in the coding segment, resulting in short (PDGF-$A_K$, 110 amino acids) and long (PDGF-$A_L$, 125 amino acids) variants of the PDGF-A chain being formed. Both variants are detectable as normal cellular proteins alongside each other, with the shorter form being the more frequent species (Matoskova et al., 1989; Young et al., 1990).

The two genes are localized on different chromosomes and demonstrate a high degree of homology. A large number of studies show that the two genes are subject to different regulatory mechanisms. A consequence of this is that, in nature, the two PDGF chasms are produced in different cell types in different ratios to each other.

All the three possible isoforms of PDGF (AA, AB and BB) occur naturally and are stored in blood platelets in so-called α-granules. Apart from the PDGF-AB heterodimer, which forms the main quantity, up to about 30% PDGF-BB can also be isolated from aged human blood platelets (Hammacher et al., 1988). Freshly prepared blood platelets also contain a high proportion (27%) of PDGF-AA (Hart et al., 1990). It can, therefore, be assumed that in the precursor cells of the thrombocytes, i.e. the megakaryocytes, the proportion of the two homodimers together corresponds approximately to that of the AB heterodimer. Since the concentration of each PDGF species in blood platelets should correlate directly with its individual importance in the wound-healing process, the most frequent isoform, i.e. PDGF-AB, in particular, receives special emphasis in the search for a "wound-healing hormone".

Each of the different isoforms possesses biological activity in vitro. It was only the availability of highly purified, recombinant PDGF isoforms (Hoppe et al., 1989; Hoppe et al., 1990) which made possible comparative studies aimed at differentiating the different spectra of activity of the various PDGF species. Meanwhile, a series of investigations confirms the different potency of PDGF-AA, PDGF-AB and PDGF-BB in chemotaxis and DNA-proliferation tests (Hosang et al., 1989; Nister et al., 1988; Reilly & Broski, 1989; Siegbahn et al., 1990), as well as their differing influence on the liberation of inositol 1,4,5-triphosphate, production of diacylglycerol and $[Ca^{2+}]_i$ mobilization. (Block et al., 1989; Sachinidis et al., 1990 A, 1990 B). Two different PDGF receptor populations, of which the PDGF-α receptor binds all the PDGF isoforms and the β-receptor binds only PDGF-BB (Hart et al., 1988; Heldin et al., 1988) provide a plausible explanation for how differences in the effect of the PDGF isoforms can evolve by way of a different receptor-activating ability. The measurable, and different, in-vitro effects of the PDGF isoforms, together with the demonstration of two different receptor populations, permit the conclusion that the in-vivo spectra of activity of PDGF-AA, PDGF-AB and PDGZ-BB are different. For this reason, the production of pure PDGF-AB, without the presence of PDGF-BB or PDGF-AA as a contaminating protein, is desirable. In order to obtain a homogeneous, well-characterized heterodimer, the homodimers would otherwise have to be completely eliminated by purification, which is additionally exacerbated by the very similar chromatographic properties of all the PDGF species.

A series of different routes for preparing recombinant PDGF homodimers, in particular PDGF-BB, has been known in part for a relatively long time (Kelly et al., 1985; Heldin et al., 1986; Hoppe et al., 1989; Beckmann et al., 1988; Bywater et al., 1988; Stroobant & Waterfield, 1984). A process for preparing highly pure PDGF-AB was described by Hoppe et al. (1990, see also PCT/EP 90/00 063). In this process, the inactive monomers, prepared separately in different *E. coli* cells, are converted into biologically active PDGF-AB by renaturation in vitro.

Despite varying length of the A and B single strands, the gene products of the three PDGF-isoforms that have been synthesized hitherto exhibit biological activities which to a large extent correspond with each other.

The criteria for the simultaneous expression of two (or more) proteins, which were mentioned in the introduction, also apply to the heterologous expression of PDGF-AB heterodimers in eukaryotic systems. The previously published strategies for preparing PDGF-AB in recombinant CHO cells (Östman et al., 1988) and using yeast expression systems [EP 0 259 632] correspond to the case example discussed under 2) above, where both PDGF genes are located on one vector in independent transcription units. Quantification of the different PDGF dimers expressed in this manner in CHO cells gave 19% for PDGF-AA, 69% for PDGF-AB and 12% for PDGF-BB (Ösman et al., 1988).

Not only the stoichiometric representation of both genes, but also, as a first priority, their coordinated expression, are to be viewed as fundamental prerequisites for the preferred synthesis of PDGF-AB heterodimers using eukaryotic expression systems. For this reason, bicistronic expression units present themselves as possible aids for expressing heterodimeric proteins and thus PDGF-AB. A system of this nature is also described for the expression of PDGF in WO 90/01550. However, as explained in more detail under point 3) above, these constricts yield only very limited expression rates for the second (and subsequent) cistron(S). Depending on the PDGF chain localized in the first cistron, homodimers of this type are predominantly formed. Attempts which have previously been described in the literature to express both PDGF genes in a eukaryotic cell using other expression systems led to proportions of homodimer by-product in the region of 30% or more. In order, nevertheless, to obtain highly pure PDGF-AB using these cell systems, elaborate and extremely wasteful purification techniques must be employed.

It is, accordingly, the object of the invention to create agents which render possible the recombinant preparation of 2 or more polypeptides, or their subunits, in quantities which are in each case equimolar, and which furthermore guarantee the preferred formation of hetero(di)mers. The yield and economy of the downstream protein purification processes are thereby substantially improved.

To achieve the object, a multicistronic expression unit for the equimolar expression of polypeptides or subunits thereof in mammalian cells as host cells is proposed according to the invention, which unit is characterized by the general formula

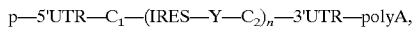

p—5'UTR—$C_1$—(IRES—Y—$C_2$)$_n$—3'UTR—polyA, in which

"p" is a transcriptional promoter,

"5'UTR" is an untranslated nucleotide sequence, n is 1, 2 or 3,

"$C_1$" and "$C_2$" are cistrons which in each case contain a gene encoding a polypeptide or its subunit, wherein, if n is 2 or 3, the sequences of the successive groups (IRES—Y—$C_2$) may be equal or different amongst each other, and further $C_1$ and $C_2$ may be equal or different, "IRES" is a nucleotide sequence of viral, cellular or synthetic origin, which at the stage of translation is responsible for internal initiation, "Y" is a nucleotide sequence which, in synergy with IRES, ensures expression of the gene(s) contained in $C_2$ in such a manner that the gene products of $C_1$ and $C_2$ are expressed in equimolar quantities, "31'UTR" is an untranslated nucleotide sequence, "polyA" is a polyadenylation signal.

In the constructs according to the patent, an equivalence in the translation efficiency was achieved by introducing intercistronic elements and, surprisingly, a 1:1 stoichiometry of the gene products was found. In this way, the essential basis has been created for expressing hetero(di)mers in animal cells. Due to the fact that the capacity of the cell for expression has been fully used up at the level of transcription and translation and, in addition, elaborate purification steps for removing homo(di)mers can to the greatest possible extent be dispensed with as a consequence of almost complete heterodimerization, a high degree of economy in the production of the respective protein in mammalian cells is ensured.

All those promoters which are active in eukaryotic cells, i.e. which can initiate gene expression in eukaryotic cells, are suitable for use as promoters in the expression units according to the invention. In particular, all constitutive and inducible promoters of viral origin (for example the retroviral "long terminal repeats" (LTR's) or the early promoter of cytomegalovirus (CMV)), of cellular origin (for example the human actin or ubiquitin promoters), or of synthetic origin, can be used. The SV40 promoter is preferred according to the invention.

The 5'UTR and the 3'UTR are any, as a rule untranslated, nucleotide sequences which can contain regulatory elements and which serve to link "$C_1$" and "$C_2$" operatively to the transcription control elements. According to the invention, the SV40 sequence from pBEH according to Artelt et al., (1988) is suitable, for example.

All those sequences of viral, cellular or synthetic origin which mediate internal binding of the ribosomes can be used as the IRES. Examples of such sequences are the IRES from polio virus type 1 and additionally the 5'UTR of encephalomyocarditis virus (EMCV), of "Theiler's murine encephalomyelitis virus" (TMEV), of "foot-and-mouth disease virus" (FMDV), of "bovine enterovirus" (BEV), of "coxsackie B virus" (CBV), and of "human rhinovirus" (HRV), and the "human immuno-globulin heavy chain binding protein" (BIP) 5'UTR, the *Drosophila antennapediae* 5'UTR and the Drosdphila ultra-bithorax 5'UTR, or genetic hybrids or fragments from the above-listed sequences. According to the invention, the IRES from polio virus type 1 according to SEQ ID NO:5 is preferred, which encompasses the first 628 nucleotides of the 5' untranslated region of polio virus type 1.

All those nucleotide sequences can be employed as "Y" which, in synergy with the IRES as given in the general formula, ensure expression of the gene(s) contained in $C_2$ in such a way that the gene products of $C_1$ and $C_2$ are expressed in equimolar quantities. In particular, the *Xenopus laevis* β-globin 5'UTR (Falcone and Andrews, 1991; Patient et al., 1983), the alfalfa mosaic virus RNA4 5'UTR (Jobling and Gehrke, 1987), the ferritin 5'UTR (animal, Klausner and Harford, 1989), the tobacco mosaic virus 5'UTR ("omega") plus leader mutants (Gallie et al., 1987A, 1987B; Gallie et al., (1988)), the turnip yellow mosaic virus (TYMV) 5'UTR, the brome mosaic virus (BMV) RNA3 5'UTR and the *Rous sarcoma* virus (RSV) 5'UTR (cf. in each case Gallie et al., 1987B), the adenovirus tripartite leader (L1–3) and variants (Berkner, Zymogenetics WO 90/01550; Berkner and Sharp (1985); Kaufman (1985)), the *Xenopus borealis* 5'UTR β-globin and the *Xenopus tropicalis* 5'UTR β-globin (cf. in each case Knoechel et al., (1986)) are suitable, the β-globin sequence from *Xenopus laevis* according to SEQ ID NO: 6 being particularly preferred according to the invention.

According to a particularly preferred embodiment of the invention, the IRES is the polio virus type 1 UTR according to SEQ ID NO: 5 and "Y" is the β-globin sequence from *Xenopus laevis* according to SEQ ID NO: 6.

In addition, further suitable IRES and "Y" sequences can be ascertained using the process which is described in more detail below and which likewise is part of the invention.

The $C_1$ and $C_2$ cistrons can, independently of each other and in arbitrary sequence, in each case contain a gene which encodes a polypeptide component of a single or heteromeric protein consisting of 2 or more such components, the genes being expressed according to the invention in an equimolar manner and the components accordingly being made available within a host cell in each case in the ratio of 1:1. Thus, cistrons $C_1$ and $C_2$ may be equal or different amongst each other, and the cistrons $C_2$ of the successive groups (IRES—Y—$C_2$) may be equal or different amongst each other. In particular, $C_1$ and $C_2$ can in each case contain genes which encode the different subunits of factor VIII, creatine kinase, haemoglobin, immunoglobulins, histocompatibility antigens, T-cell receptors, scatter factor (HGF-SF), members of the transforming growth factor type β family, bone morphogenic protein (BMP), members of the integrin family, or PDGF, or their natural or synthetic variants and derivatives.

According to a particularly preferred embodiment, the invention relates to PDGF-AB; correspondingly, in the particularly preferred expression unit, "n" is equal to 1, and $C_1$ and $C_2$ alternatively contain a gene encoding the A or the B chain of PDGF, a biologically active analog, or a fragment thereof, both genes being represented simultaneously in the expression unit.

In principle, however, additional changes in the PDGF-B precursor had to be undertaken for producing PDGF-AB, since PDGF-A and PDGF-B precursor molecules differ in their biophysical properties. It is known that the expression of PDGF-B is not inevitably correlated with the secretion of biologically active material. A large part of the expressed PDGF-BB remains in close association with the cytoplasmic membrane (Robbins et al., 1985). When monocistronic expression vectors are used, the expression of PDGF-B is significantly lower than that of PDGF-A in CHO cells. The reason for this is that PDGF-BB is retained extracellularly on the plasma membrane of the producing cell as a result of electrostatic interaction, and only a small portion of it is released into the medium (La Rochelle et al., 1990; La Rochelle et al., 1991; Östman et al., 1991). A short segment of the C-terminal region of the PDGF-B precursor is responsible for bringing about the retention (Östman et al., 1991). In the constructs according to the patent, this segment of the PDGF-B precursor sequence was removed by introducing a stop codon at the 3' end of the mature PDGF-B chain. The correspondingly truncated DNA sequence of the PDGF-B precursor is designated $^{B190}$. Secreted PDGF-BB from culture supernatants of cells which have been transformed with this construct is designated B*.

To prepare PDGF-AB according to the invention, $C_1$ or $C_2$ can contain the PDGF-$A_K$ (SEQ ID NO: 1(encoded amino acid sequence shown in SEQ ID NO:2)) or the PDGF-$A_L$ precursor sequence, the complete PDGF-B precursor sequence (SEQ ID NO: 3(encoded amino acid sequence shown in SEQ ID NO:4)), the v-sis gene from simian sarcoma virus or the base pairs 283 to 609 according to SEQ ID NO: 3(encoded amino acid sequence shown in SEQ ID NO:4), or a gene fragment which encodes a PDGF-B precursor molecule which is truncated by replacing the arginine encoding codon in amino acid position 191 of the PDGF-B precursor by a translation stop codon. The aforesaid genes can be present in any combination as long as in each case a gene encoding the A chain and a gene encoding the B chain are present.

According to the invention, an expression unit is particularly preferred in which $C_1$ and $C_2$ alternatively contain the PDGF-$A_K$ sequence (SEQ ID NO: 1(encoded amino acid sequence shown in SEQ ID NO:2)) or the truncated PDGF-B precursor sequence (SEQ ID NO: 24(encoded amino acid sequence shown in SEQ ID NO:25)), and both genes are represented simultaneously in the expression unit.

To identify further suitable IRES and "Y" sequences as described in detail below, expression units are employed in which "n" is 1 and $C_1$ and $C_2$ contain reporter genes which are different from each other. According to a particularly preferred embodiment of the invention, an expression unit of this nature contains the genes encoding luciferase (SEQ ID NO: 22(encoded amino acid sequence shown in SEQ ID NO:23)) and secretory alkaline phosphatase (SEQ ID NO:20 (encoded amino acid sequence shown in SEQ ID NO:21)) as the reporter genes.

The invention additionally relates to recombinant DNA vectors which contain the expression units according to the invention inserted in an operative manner. Vectors which are preferred according to the invention, and their preparation, are presented in FIGS. 1 to 6C.

The invention additionally includes host cells which are mammalian cells and which are transformed with a vector which carries the expression unit according to the invention inserted in an operative manner. They are preferably CHO or BHK cells.

A particularly preferred embodiment of the invention relates to host cells, in particular BHK cells, which are transformed with vectors which carry one of the expression units encoding PDGF-AB as described in detail above. These are preferably vectors in which $C_1$ and $C_2$ alternatively contain the PDGF-$A_K$ sequence (SEQ ID NO: 1(encoded amino acid sequence shown in SEQ ID NO:2)) or the complete (SEQ ID NO: 3(encoded amino acid sequence shown in SEQ ID NO:4)) or truncated (SEQ ID NO: 24(encoded amino acid sequence shown in SEQ ID NO:25)) PDGF-B precursor sequence.

In accordance with the invention, transformed, PDGF-AB producing, BHK cells were deposited under the designation 92-22-6 (pSBC-PDGF-A/-G-$^{B190}$, see. Tab. 2), corresponding to DSM ACC 2048, or 92-22-7 (pSBC-PDGF-B190/-G-A, see Tab. 2), corresponding to DSM ACC 2049, with the Deutsche Sammlung von Mikroorganismen und Zellkulturen GmbH (DSM) (German collection of microorganisms and cell cultures) on the 11.8.1992.

For identifying further suitable IRES or "Y" sequences, host cells are cultivated which are transformed with vectors which carry the expression units containing the reporter genes, as described in detail above. Preferably, the vectors are vectors according to the invention which contain the genes encoding luciferase and secretory alkaline phosphatase.

In accordance with the invention, host cells transformed with the genes for luciferase (SEQ ID NO: 22(encoded amino acid sequence shown in SEQ ID NO:23)) and secretory alkaline phosphatase (SEQ ID NO: 20(encoded amino acid sequence shown in SEQ ID NO:21)) were deposited under the designation 91-46-9 (pSBC-SEAP/-G-LUC, see Tab. 1), corresponding to DSM ACC 2046, and 91-46-10 (pSBC-G-SEAP-LUC, see Tab. 1), corresponding to DSM ACC 2047, with the German collection of microorganisms and cell cultures (DSM) on the 11.8.1992.

The invention additionally includes processes for preparing those proteins which consist of equimolar portions of different polypeptide subunits, by cultivating host cells, which are transformed with the expression units according to the invention described in detail above, in a suitable medium and separating the protein thus produced from the cells and the medium.

As examples, proteins such as factor VIII, creatine kinase, haemoglobin, immunoglobulins, histocompatibility antigens, T-cell receptors, scatter factor (HGF-SF), members of the transforming growth factor type β family, bone morphogenic protein (BMP), members of the integrin family or PDGF, or natural or synthetic variants or derivatives thereof, can be prepared in this manner.

Using the vectors according to the invention, it is also possible for the first time to produce dimers of PDGF or of other proteins of which different splice forms exist, such as, for example, VEGF (vascular endothelial growth factor), which previously could not readily be prepared, such as dimeric PDGF-A of the type long/short chain, PDGF-$A_L$/PDGF-$A_K$, or molecules of the type PDGF-B/v-sis. Another option is represented by dimers or multimers in which only one chain contains signal sequences for post-translational modification, for example a glycosylation signal. In this way, therefore, proteins which are glycosylated or otherwise modified in a "one-sided" manner can be prepared.

According to a particularly preferred embodiment of the invention, the process is used to prepare heterodimeric rPDGF-AB by cultivating host cells, which are transformed with vectors which carry expression units according to the invention which carry genes encoding the PDGF-A and PDGF-B chains, in a suitable medium as described in detail above. The rPDGF-AB produced in this way is subsequently separated off from the cells and the medium.

It was possible to demonstrate in Example 2 that PDGF-AB heterodimers can be exclusively or virtually exclusively produced with the aid of the bicistronic vector systems according to the invention, and the synthesis of PDGF homodimers can be counteracted. Unexpectedly, the level of expression of the second cistron is stimulated in this construct in such a way that it tallies with the level of expression of the first cistron.

In this connection, and according to the invention, BHK cells are preferably cultivated which are transformed with vectors in which $C_1$ and $C_2$ alternatively contain in each case the PDGF-$A_K$ sequence (SEQ ID NO: 1(encoded amino acid sequence shown in SEQ ID NO:2)) or the complete (SEQ ID NO:3(encoded amino acid sequence shown in SEQ ID NO:4)) or the truncated (SEQ ID NO: 24(encoded amino acid sequence shown in SEQ ID NO:25)) PDGF-B precursor sequence.

All the known media for cultivating mammalian cells, including synthetic, protein-free or protein-poor production media, are suitable as the medium. DMEM (Dulbecco's modified Eagle medium), enriched with 4.5 g/l glucose and 5 to 10% FCS, was preferred according to the invention.

The rPDGF-AB can be separated from the cells and the medium by conventional processes (cf., for example, Östmann et al., 1988). A highly efficient process, which was developed for PDGF-AA from BHK cells (Eichner et al., 1989), is that which is preferred.

The invention finally relates to heterodimeric rPDGF-AB which is essentially free of homodimeric contaminating products and which can be obtained by cultivating the above-described host cells according to the invention. It has emerged, surprisingly, that the host cells transformed with the construct according to the invention secrete the heterodimeric PDGF-AB at a purity of 90% or more, based on the total quantity of PDGF formed. According to the invention, heterodimeric PDGF-AB is preferred which is made available by cultivating BHK cells which are transformed with the construct according to the invention.

The rPDGF-AB according to the invention primarily differs from the previously known recombinant PDGF-AB products on account of its high degree of purity. As remarked in the introduction, no recombinant process has hitherto been described in which 90% or more of the resulting product consists of the heterodimer. Since com plete separation of the homodimers from the heterodimer is virtually impossible, the known products are inevitably mixtures of all 3 isoforms.

In addition to this, the known products, depending on their preparation, suffer from disadvantages in many respects. For example, it is known that heterologous gene expression in yeast cells, as described in EP 259 632 or 288 307, leads to protein products whose glycosylation patterns are altered as compared with the human product. Furthermore, PDGF-B expressed in yeast cells is, at least in part, incompletely processed and/or is proteolytically degraded (cf. WO 92/01716). Products of this nature thus have an altered carbohydrate pattern and are contaminated with products of proteolytic degradation. To avoid the aforesaid disadvantages, WO 92/01716 describes processes for preparing modified PDGF chains in which the consensus sequences for glycosylation, and the protease-sensitive domains, have been removed. However, modifications of this type affect the biological activity of the product (cf. WO 92/01716).

According to a particularly preferred embodiment of the invention, heterodimeric rPDGF-B is obtained by cultivating BHK cells which have been transformed according to the invention, for example by cultivating those cells which were deposited under the designation 92-22-6, corresponding to DSM ACC 2048, or the designation 92-22-7, corresponding to DSM ACC 2049, with the German collection of microorganisms and cell cultures (DSM) on the 11.8.1992.

It is indeed true that WO 90/08163 discloses the recombinant preparation of PDGF-AB in bacterial cells, in particular in *E. coli,* which preparation inevitably leads to an unglycosylated product. However, a PDGF-B chain expressed by this process in *E. coli* cells is truncated at the amino terminus by 12 amino acids. In addition to this, the product from bacteria must be renatured in vitro, a procedure in which the correct intermolecular and intramolecular formation of the disulphide bridges, and the correct folding of the protein, is not guaranteed, with the consequence that the immunological properties of the product may be altered and the biological activity affected.

The heterodimeric rPDGF-AB according to the invention is preferably formulated with pharmaceutically tolerated auxiliary agents and excipients as a pharmaceutical preparation, in particular for wound healing. In this context, it can be contained as the active compound in plasters and wound bandages and the like. While it is particularly suitable for topical application, other forms of administration, in the course of which the active compound is introduced into the wound or administered subcutaneously, are also suitable. For example, the PDGF-AB can be administered subcutaneously, in a suitable matrix having a depot function, in the peripheral region of the wound, or directly injected subcutaneously.

Further, the rPDGF-AB of the present invention is suitable for manufacturing cosmetical preparations, for example for skin regeneration, skin smoothening, prevention of scarring or of skin ageing as well as for application on sunburn.

Suitable auxiliary agents and excipients include water-based cellulose gels, biodegradable polymers and any ointment bases and cream bases, and sprays. Furthermore, additional active compounds which affect wound healing, such as, for example, collagen, fibronectin, factor XIII, fibroblast growth factor (aFGF, bFGF), transforming growth factor type α or β epidermal growth factor, insulin or insulin-like growth factor (IGF I and II), or further growth factors, may be contained in the preparations according to the invention. The products according to the invention can, for example, also be present in wound dressings in aqueous solution.

As explained above, the invention is based on the realization that, by incorporating a particular sequence "Y", the IRES-dependent translation of $C_2$ can be increased such that it achieves the efficiency of "cap"-dependent translation. Accordingly, the sequence "Y" is able to cooperate with the IRES such that an increase of IRES-dependent translation initiation is obtained which at least corresponds to the efficiency of cap-dependent translation efficiency. "Y"

sequences which fulfil this function are described in full above. According to the patent, the β-globin 5'UTR from *Xenopus laevis* is preferred.

Further sequences which fulfil the prerequisites according to the invention can be identified by a process in which, for detecting translation-influencing "Y" sequences which, in synergy with the IRES, bring about the equimolar expression of the gene products of $C_1$ and $C_2$ in expression units according to the invention,
 (a) the sequences to be investigated as Y are introduced into bicistronic or multicistronic expression units in which $C_1$ and $C_2$ in each case contain a reporter gene, these genes encoding different and readily distinguishable gene products,
 (b) vectors are constructed which contain the respective expression unit inserted in an operative manner,
 (c) mammalian cells as host cells are transformed with the vectors from step (b) and cultivated in a suitable medium, and
 (d) the expression products of $C_1$ and $C_2$ are quantified in the medium or following separation from the cells and/or the medium.

Preferably, CHO or BHK cells are used as the host cells in step (c), BHK-21 cells being particularly preferred.

Alternatively, further IRES sequences which fulfil the prerequisites according to the invention can be identified by a process in which, for detecting translation-initiating IRES sequences which, in synergy with "Y", bring about the equimolar expression of the gene products of $C_1$ and $C_2$ in expression units according to claims 1 to 15,
 (a) the sequences to be investigated as the IRES are introduced into expression units in which $C_1$ and $C_2$ in each case contain a reporter gene, these genes encoding different and readily distinguishable gene products,
 (b) vectors are constructed which contain the respective expression unit inserted in an operative manner,
 (c) mammalian cells as host cells are transformed with the vectors from step (b) and cultivated in a suitable medium, and
 (d) the expression products of $C_1$ and $C_2$ are quantified in the medium or following separation from the cells and/or the medium.

In this process, CHO or BHK cells are preferably used as the host cells, and, in a particularly preferred manner, BHK cells are used which contain the genes encoding luciferase and secretory alkaline phosphatase (LUC) and (SEAP), respectively, as the reporter genes.

The invention is explained below with the aid of Figures and Examples.

I. DESCRIPTION OF THE FIGURES

Figure 1B:
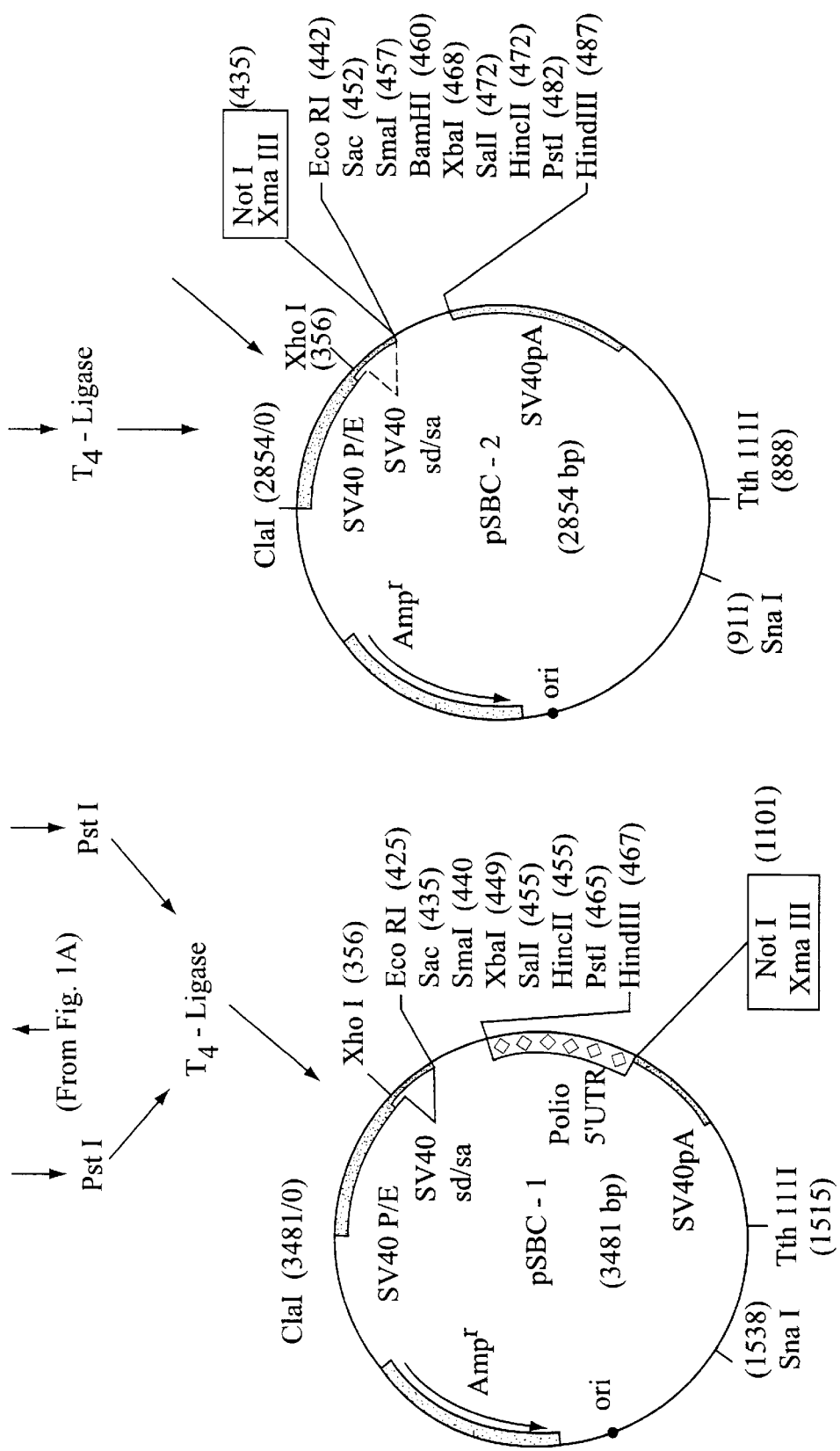

FIGS. 1A and 1B) Preparation of the basic vectors pSBC-1 and pSBC-2

For the construction of vector pSEC-1, a 627 bp MseI/BalI-fragment from the plasmid pGEM3–5'polio (M) (Sarnow, 1989) was employed as the matrix for a PCR using the following primers (FIG. 1):

```
5'-polio #1⁵' TTT CTGCAG AAGCTT AAAACAGCTCTGGGG³' (SEQ ID NO: 14)
                  PstI  HindIII 3'-polio #2⁵' TT GCGGCCGC AATCCAATTCGCTTTATG³' (SEQ ID NO: 15)
                 NotI
```

The 652 bp fragment resulting from the amplification was treated with Pol I K, then cleaved with PstI and inserted into the correspondingly prepared vector pBEH (Artelt et al., 1988). For the construction of vector pSBC-2, the plasmid pBEH was linearized with EcoRI and the following oligonucleotide sequences were hybridized and inserted: 1

```
E-N-E #1  ⁵'AATT GCGGCCGC G³'     (SEQ ID NO: 16)

E-N-E #2          ³'CGCCGGCG CTTAA⁵' (SEQ ID NO: 17)
```

FIGS. 2A and B) Construction of the expression vectors pSBC-LUC/SEAP and pSBC-SEAP/LUC The coding CDNA sequences of the genes for luciferase and secreted alkaline phosphatase were inserted into the monocistronic vectors pSBC-1 and pSBC-2 (FIGS. 2A and 2B) using EcoRI/HindIII restrictions. Fusion of the two vectors to form a bicistronic expression unit was carried out using restriction enzymes XmnI/NotI.

FIG. 2C) Construction of the plasmids pSBC-SEAP/-G-LUC and pSBC-G-SEAP/LUC.

The expression constructs pSBC-SEAP/-G-LUC and pSBC-G-SEAP/LUC are derived from the plasmids depicted in FIGS. 2A and 2B. They contain in addition the oligomer G (SEQ ID NO: 6) which was ligated into the unique NotI site. The oligomer G is constructed in such a way that, by ligation into the NotI site, the 5'-NotI site is lost (a SalI site is contained at this point) but the 3'-NotI site is preserved.

Figures 2, 2C, 3:
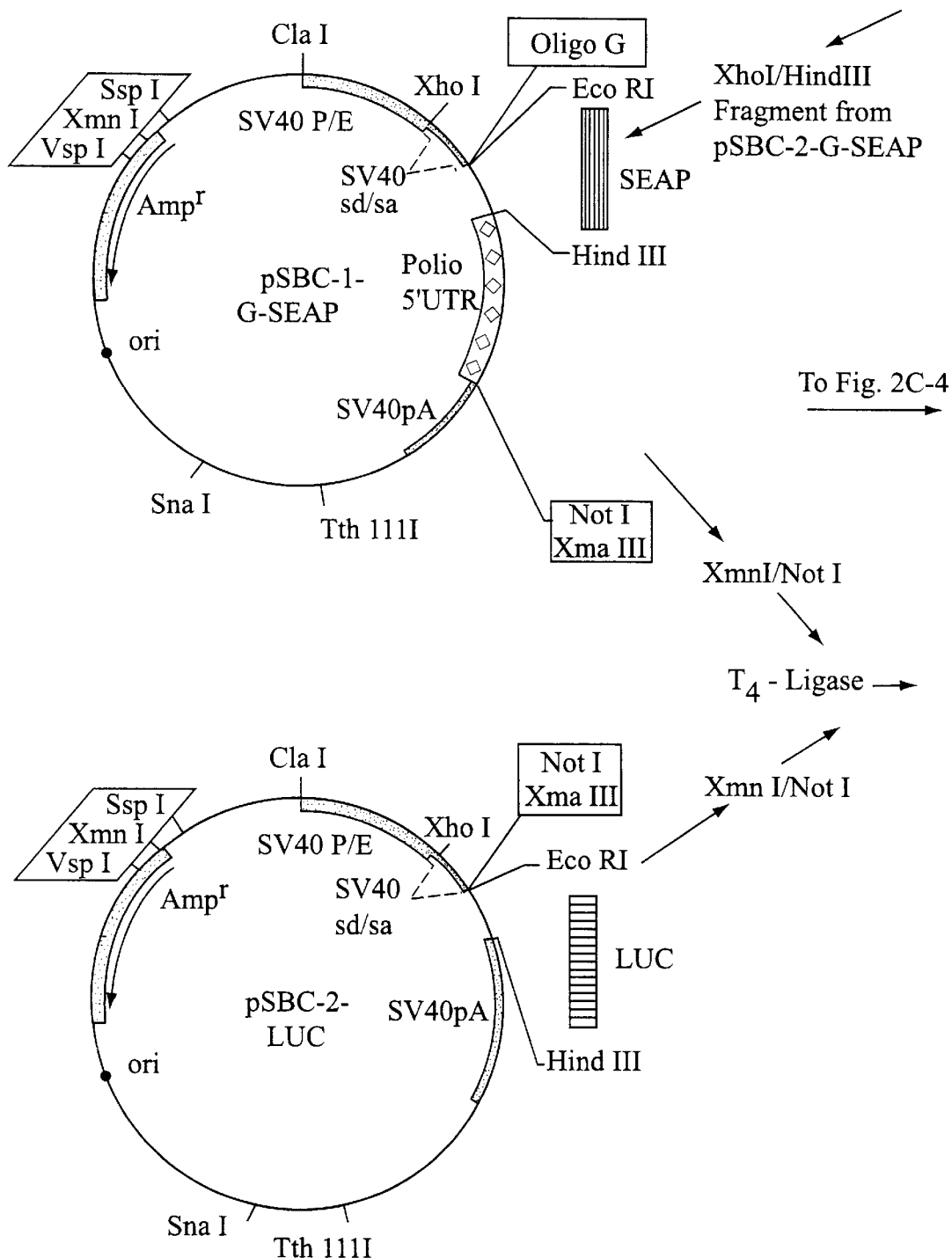

FIG. 3) Schematic representation of the vector M13BCL1

The region of pMVW-2 which is homologous to c-sis (PDGF-B) is indicated on the vector map. The regions of the mature PDGF-B and of the NcoI/SalI adapter are emphasized by black bars.

Figures 2, 2C, 3, 4:
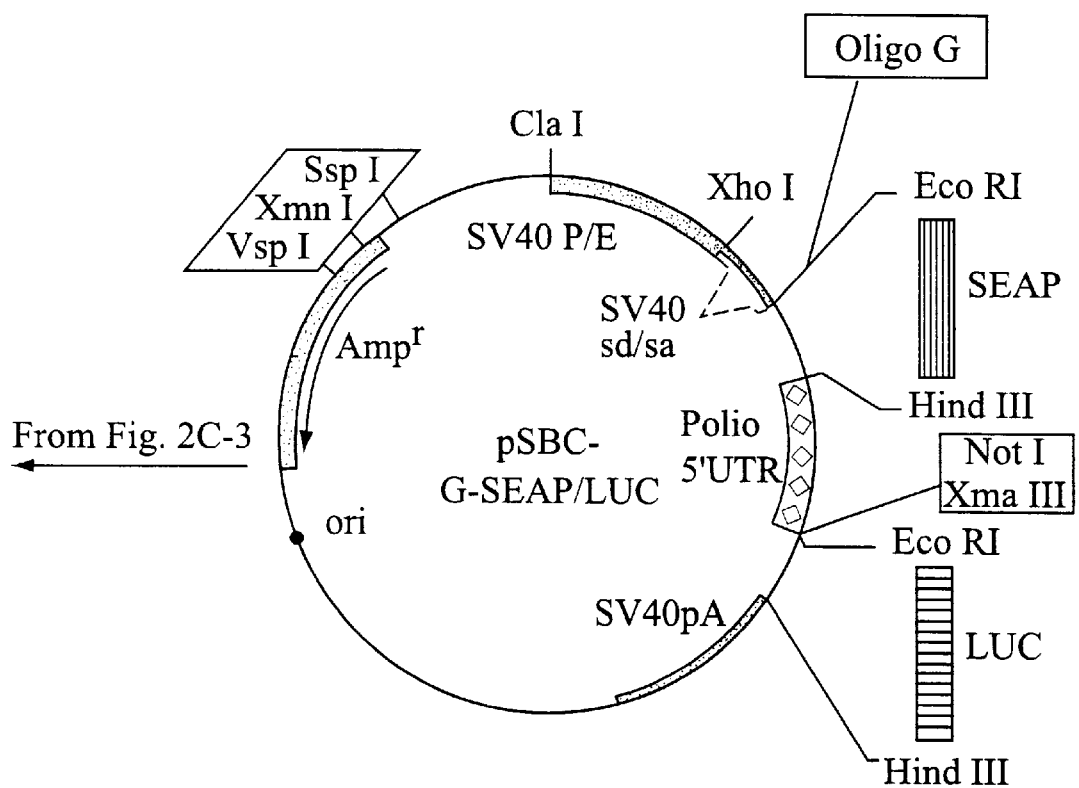
Figure 3:
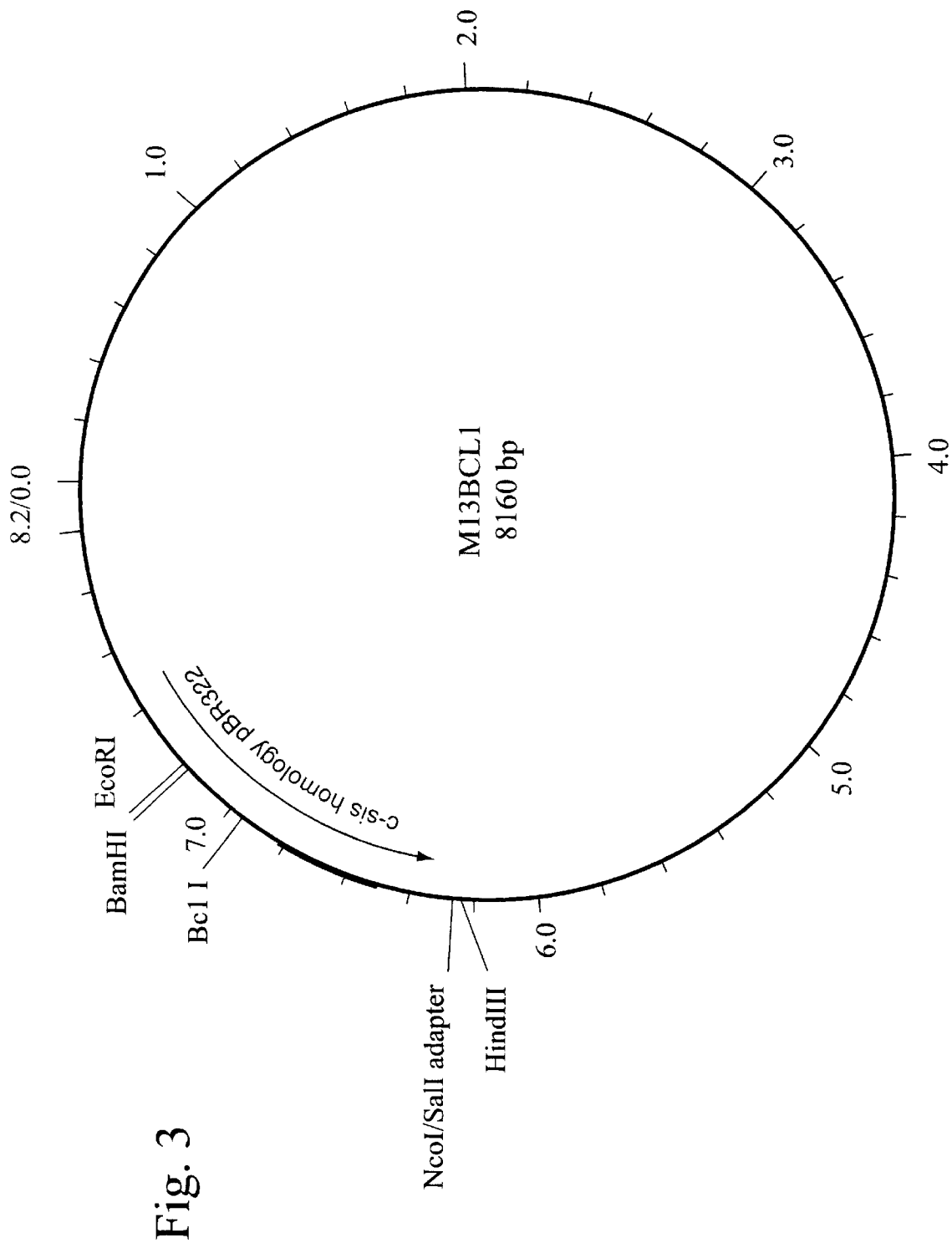
Figures 1, 4:
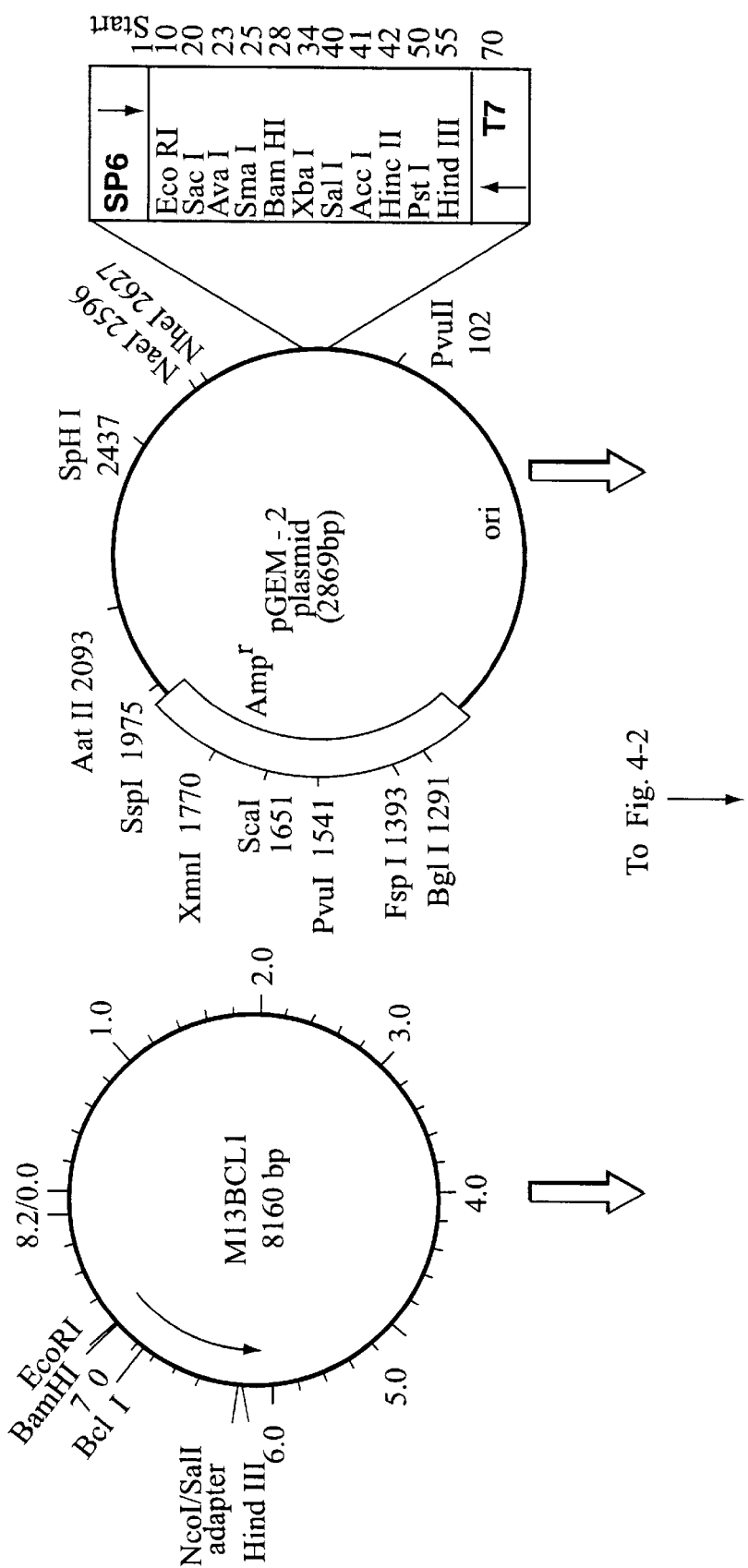
Figures 2, 4:
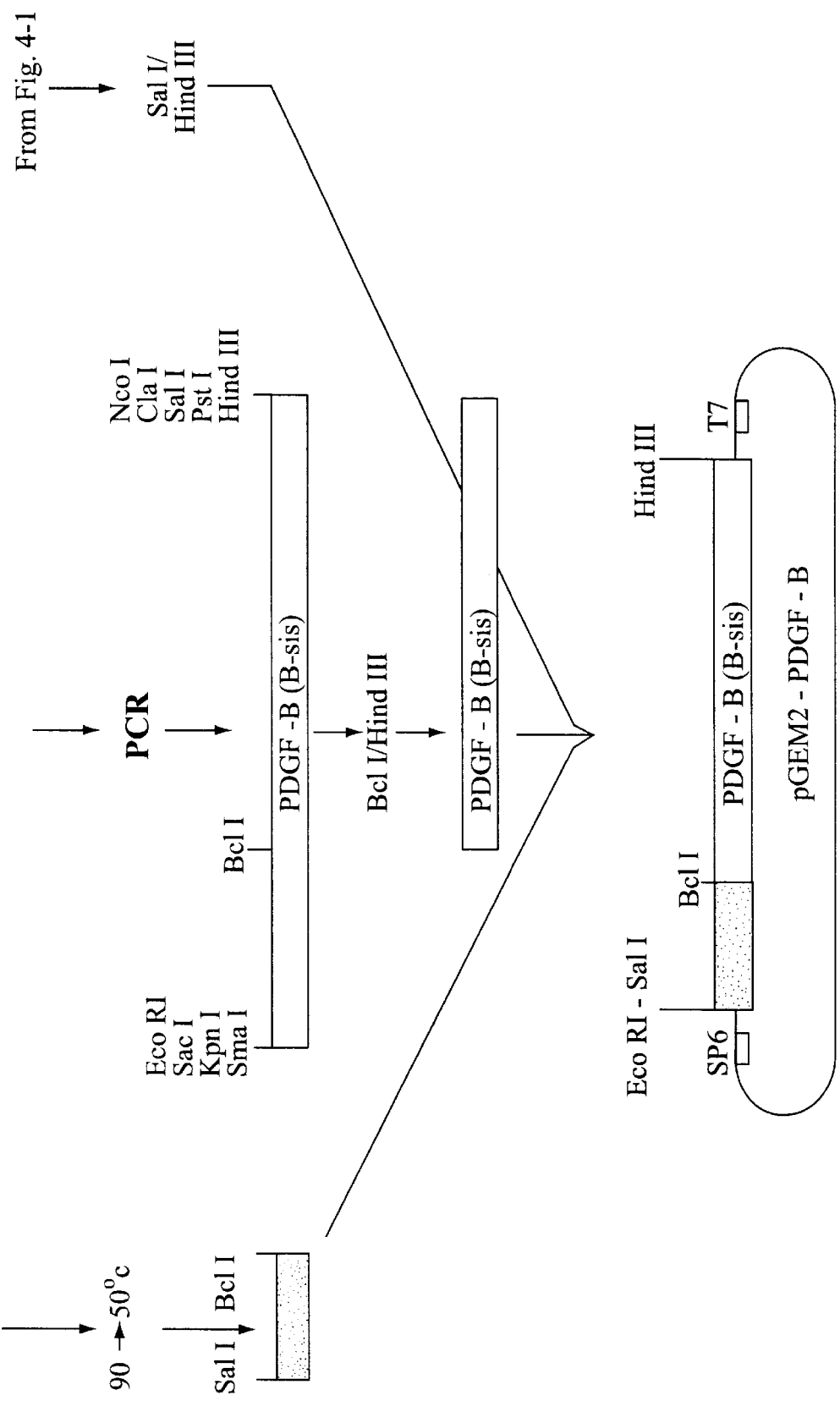

FIG. 4) Reconstitution of the complete PDGF-B precursor sequence

The plasmid pMVW-2 contains the cDNA of the human PDGF-B gene, which is incomplete in the 5'-translated region of the precursor sequence (Weich et al., 1986). In order to reconstitute the authentic PDGF-B precursor, a BclI cleavage site was introduced into the 5'-terminal region of the precursor by means of a C-T exchange in position 30 of the coding segment of clone pMVW-2. As a result of this step, only a short segment of the coding region is finally lost and, in connection with this, the locally encoded amino acid (aspartic acid) is preserved. Since, in most *E. coli* strains, the BclI cleavage site is resistant to enzymic cleavage as a result of methylation, the fragment containing this cleavage site must either be recloned into a dam⁻ strain or amplified by means of a PCR step. The missing region of the precursor is then inserted as a synthetic SalI/BclI fragment [oligomers PPDGFB1 and PPDGFB2].

For this, the 914 bp BamHI/NcoI fragment from pMVW-2 was first inserted by way of a synthetic adapter [oligomers NCCLSA1, SEQ ID NO: 9 and NCCLSA2, SEQ ID NO: 10] into the BamHI/SalI-cleaved bacteriophage M13mp19 (pharmacia). This construct provided the necessary single-stranded DNA for the subsequent in-vitro mutagenesis step, which was carried out using the oligomer-directed in-vitro mutagenesis system (version 2) from Amersham, based on the method of Eckstein et al. [Taylor et al., (1985), Nakamaye K. and Eckstein F. (1986), Sayers et al., (1988)]. Using the synthetic primer PDGBBCL (SEQ ID NO:11) a base exchange (C to T) in position 144 of the sequence depicted under SEQ ID NO: 3(encoded amino acid sequence shown in SEQ ID NO:4) is achieved after the mutagenesis and a BclI cleavage site thereby introduced in the 5' region of the PDGF-B precursor. This mutagenesis derivative was designated M13BCL1 (FIG. 3).

A 1100 bp fragment from M13BCL1 was amplified in a PCR step using the primers M1317MER (SEQ ID NO: 7) and M1324MER (SEQ ID NO: 8), and subsequently subjected to a restriction with BclI/HindIII, and the resulting 770 bp fragment was then isolated. The synthetic oligomers PPDGFB1 (SEQ ID NO: 12) and PPDGFB2 (SEQ ID NO: 13) form the missing 5' region of the PDGF-B precursor up to the BclI cleavage site. After annealing, this double-stranded oligomer was subsequently ligated, together with the 770 bp PDGF-B fragment, into the vector pGEM-2 (Promega), which had previously been prepared by restricting with SalI/HindIII (FIG. 4). The authentic sequence of PDGE-B was verified by sequencing completely.

Figure 5:
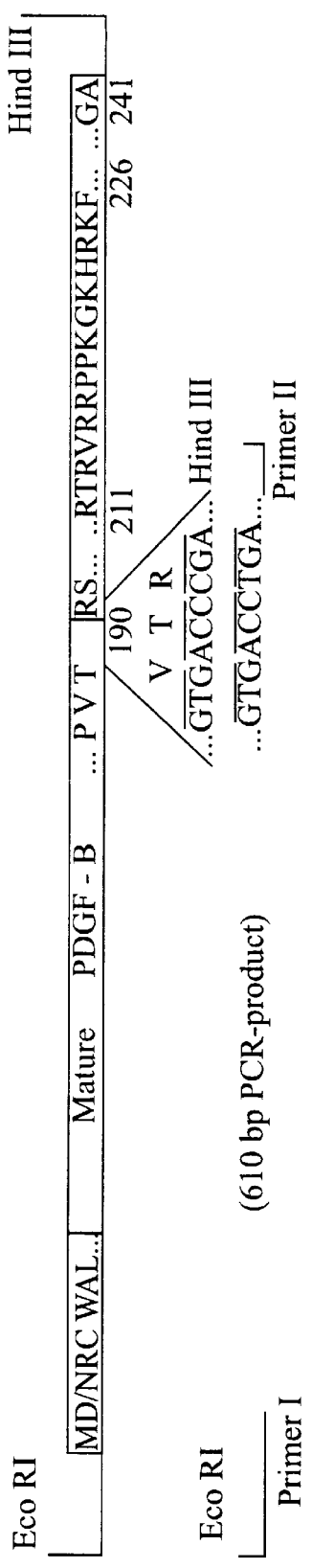

FIG. 5) Preparation of a secretory PDGF-B chain

Using monocistronic expression vectors, the expression of the PDGF-B gene in BHK cells is lower than that of PDGF-A. The reason for this is that PDGF-BB is retained extracellularly on the plasma membrane of the producing cell, and only a small portion is released into the medium (La Rochelle et al., 1991; Östmann et al., 1991). The retention of PDGF-B is mediated by the carboxy-terminal region, which, in the natural situation, is cleaved off in association with the release of PDGF-B (La Rochelle et al., 1991). In order to prepare a variant of PDGF-B which can more readily be secreted, a PCR-mediated mutagenesis was carried out in which a stop codon was inserted at the amino acid in position 191 (Arg) of the PDGF-B precursor. The region which is responsible for the retention is not expressed in the mutant (PDGF-B190, SEQ ID NO: 24(encoded amino acid sequence shown in SEQ ID NO:25)) prepared in this way. The 610 bp-long PCR product was obtained using the following primers (FIG. 5):

PDGF-B190 Primer I    5'GAATTCGAGCTCGCCCGGG3'  (SEQ ID NO: 18)

PDGF-B190 Primer II   5'CCCGGGAAGCTTCCGGTTATCAGGTCACAGGCCGTGC3' (SEQ ID NO: 19)

FIGS. 6A and B) Construction of the expression vectors pSBC-PDGF-A/B and pSBC-PDGF-B/A The complete coding cDNA for the PDGF-B precursor (Ratner et al., 1985) is present in the vector pGEM2-PDGF-B (FIG. 4). The complete cDNA sequence of the short variant of the PDGF-A chain (Betsholtz et al., 1986) is contained in the expression vector pODA (Eichner et al., 1989). This vector was obtained by cloning the RsaI fragment from pPGF-1 (Hoppe et al., 1987) into the SV-40 expression vector pBEH (Artelt et al., 1988). The coding cDNA sequences of the PDGF-A and PDGF-B chains were inserted into the monocistronic vectors pSBC-1 and pSBC-2 using EcoRI/HindIII restrictions (FIG. 1). The fusion of the two vectors to form a bicistronic expression unit was carried out using the restriction enzymes XmnI/NotI (FIG. 6A, 6B).

FIG. 6C) Schematic representation of the plasmids pSBC-PDGF-A/-G-B190 and pSBC-PDGF-B190/-G-A The expression constructs pSBC-PDGF-A/-G-B 190 and pSBC-PDGF-B190/G-A are derived from the plasmids depicted in FIGS. 6A and 6B. They additionally contain the oligomer G (SEQ ID NO:6 ), which was ligated into the unique NotI site. The oligomer G is constructed in such a way that ligation into the NotI site results in the 5'-NotI site being lost (a SalI site is contained at this location), but, however, the 3'-NotI site is preserved.

FIG. 7), Sandwich-ELISA for detecting PDGF-A and PDGF-B chains with the aid of two polyclonal anti-PDGF anti-bodies: calibration curves from PDGF standards.

Polystyrene plates were coated with goat anti-PDGF-AB-IgG (polyclonal, from Collaborative Research); following incubation with various PDGF standards (see below), bound PDGF was detected with the aid of polyclonal rabbit anti-PDGF-AA or anti-PDGF-BB, followed by peroxidase-labelled anti-rabbit-IgG. When anti-PDGF-AA is used (ELISA I.1), O.D. signals are obtained in the sequence: PDGF-AB>PDGF-AA>>PDGF-BB (7.1). Using anti-PDGF-BB (ELISA I.2), maximum O.D. values are obtained for PDGF-AB and PDGF-BB from 10 ng/ml, while PDGF-AA does not yield any signal up to 1000 ng/ml (7.2). [Source of the standards: AB: from human blood platelets, from Promega Corp. No. G 6191; BB: recombinant from yeast, from Promega Corp. No. G 5191; AA: recombinant from BHK cells, about 70% pure (Eichner et al., 1989)].

FIG. 8) Sandwich-ELISA for detecting PDGF-AB with the aid of a monoclonal and a polyclonal anti-PDGF anti-body: calibration curves from PDGF standards.

Polystyrene plates were coated with sheep anti-mouse IgG and subsequently incubated with a mouse hybridoma supernatant (from clone 1B3, contains monoclonal antibodies against the B chain in PDGF-AB and PDGF-BB); following incubation with various PDGF standards (see legend to FIG. 7), PDGF-AB was detected with the aid of a polyclonal rabbit anti-PDGF-AA, followed by peroxidase-labelled anti-rabbit IgG.

Using PDGF's from eukaryotic sources, a specific signal is obtained with PDGF-AB (from human blood platelets), a slight cross reaction being obtained with PDGF-BB.

Figure 9:
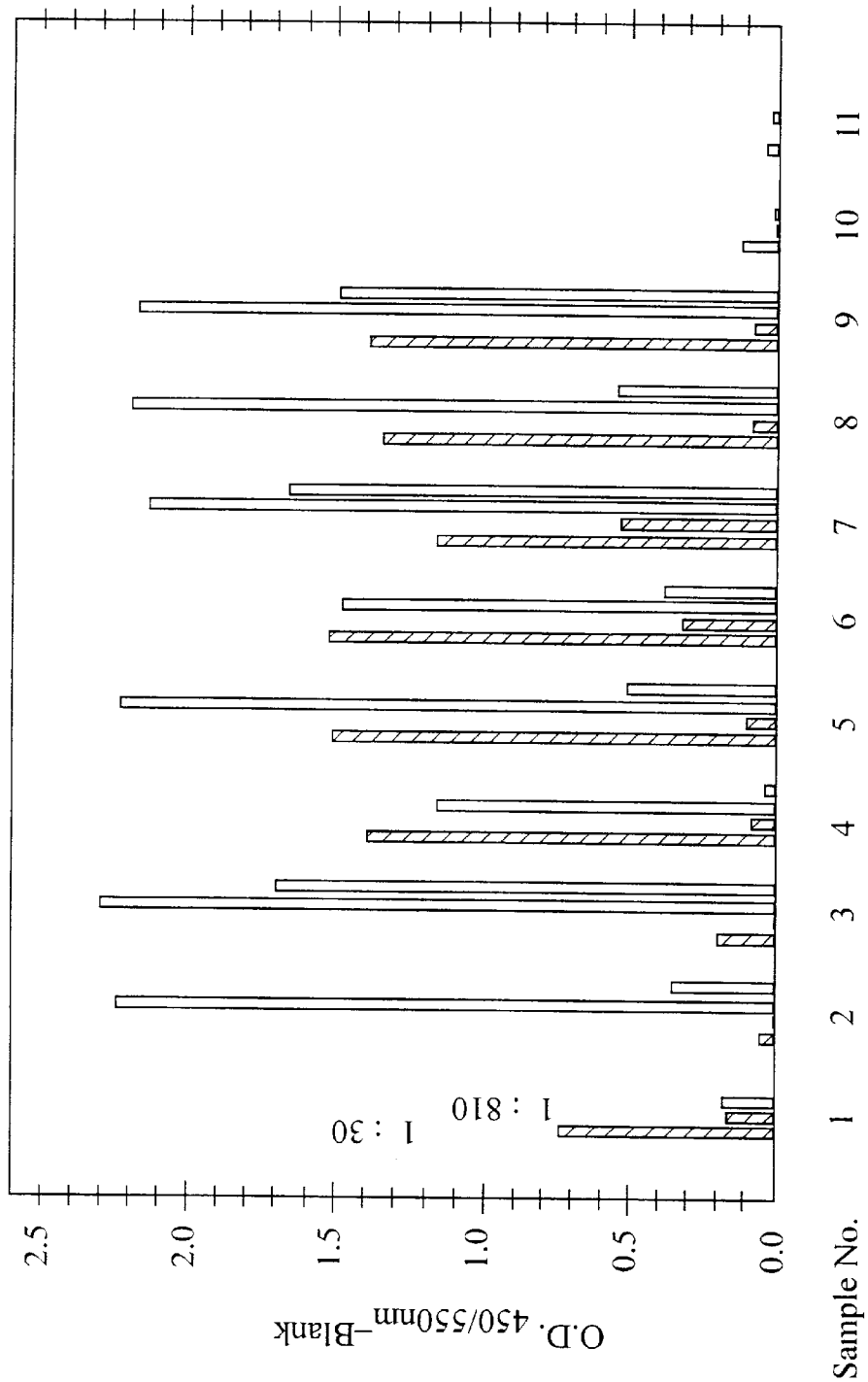

FIG. 9) Detection of- the PDGF-A chain or PDGF-B chain in culture supernatants of recombinant BHK cells using ELISA I:

Calibration curves from standards, see FIGS. 7.1 and 2; the samples originated from BHK cells which had been transfected with the following genes:

Sample 1: pSBC-2-PDGF-A; sample 2: pSBC-2-PDGF-B; sample 3: pSBC-2-G-PDGF-B190; sample 4: pSBC-PDGF-A/B; sample 5: pSBC-PDGF-B/A; sample 6: pSBC-PDGF-A/-G-B190; sample 7: pSBC-PDGF-B190/-G-A; sample 8: pSBC-2-PDGF-A+pSBC-2-PDGF-B; sample 9: pSBC-PDGF-A+pSBC-2-G-PDGF-B190; sample 10: pSBC-LUC/-G-SEAP; sample 11: pSBC-SEAP/-G-LUC.

TABLE 1

Increasing the expression of reporter genes by inserting a cellular sequence (globin) into monocistronic and bicistronic vectors
left-hand side: schematic representation of the DNA constructs

| | DNA | expected size of the mRNA |
|---|---|---|
| 1) | pSBC-2-LUC | 1870 nt |
| 2) | pSBC-1-LUC | 2497 |
| 3) | pSBC-2-G-LUC | 1904 |
| 4) | pSBC-1-G-LUC | 2531 |
| 5) | pSBC-SEAP/LUC | 4407 |
| 6) | pSBC-G-SEAP/LUC | 4441 |
| 7) | pSBC-SEAP/G-LUC | 4441 |
| 8) | pSBC-SEAP/LUC (delta) polio | 3780 |
| 9) | pSBC-LUC/SEAP | 4407 |

L = structural gene for luciferase
S = structural gene for secreted alkaline phosphatase
IRES = "internal ribosomal entry site"
G = sequence from Xenopus laevis globin mRNA
pA = polyadenylation site from SV40 centre: Northern blot analysis

The mRNA from the total pool of the BHK cells, which had been stably transfected with the monocistronic and bicistronic expression constructs for LUC and SEAP, was examined. The RNA was isolated by the method of Purchio et al., (1979), fractionated on a 1% agarose-formaldehyde gel (Lehrach et al., 1977), blotted onto a nylon membrane and hybridized with [$^{32}$P]-labelled actin-, LUC- and SEAP-specific probes. In accordance with expectation, the monocistronic mRNAs have a size of about 1900–2500 nt, whereas, in the case of the bicistronic mRNAs, the size corresponding to the coding sequences of the two reporter genes (about 3800–4400 nucleotides) is present. This demonstrates that the corresponding gene products are read off a single bicistronic mRNA.

right hand side: results of luciferase and SEAP expression

The results were determined as described under 1.1 and 1.2.

Table 2) Productivity of the monocistronic and bicistronic expression vectors for the PDGF-A and PDG:--B chains in BHK cells The concentration of PDGF in the culture supernatants was determined with the aid of mitogen tests. PDGF-AB was specifically detected using ELISA II (see 2.3, calibration curves from standards, see FIG. 8).

II. EXAMPLES

The expression applications listed in the Examples are based on monocistronic and bicistronic transcription units.

The genes to be expressed are in each case integrated into the vectors pSBC-1 and pSBC-2. The vector construction simplifies the recombination of pSBC-1 and pSBC-2 to form the bicistronic vector, as demonstrated in FIGS. 2A–2C for the expression of the LUC and SEAP genes and in FIGS. 6A–6C using the example of the PDGF-A and PDGF-B genes. Following transfer of the plasmid pSBC-PDGF-A/-G-B190 (G=β-globin sequence from the Xenopus laevis according to SEQ ID NO: 6) into animal cells, translation of PDGF-A is effected in a cap-dependent manner and translation of PDGF-B in dependence on the polio-IRES. In a corresponding manner, pSBC-PDGF-B190/-G-A and the reporter genes LUC and SEAP are translated by monocistronic and/or bicistronic mRNA molecules.

Example 1

Expression of the Reporter Genes LUC and SEAP Using the Bicistronic Vector System 1.1 Method of detecting luciferase Luciferase is contained in cell extracts. Its activity can be quantitatively determined by adding luciferin (substrate), ATP and $Mg^{2+}$, and can be taken to be a measure of the activity of the luciferase gene. The following reaction takes place (de Wet et al., 1987):

luciferase+luciferin+ATP+$Mg^{2+}$—luciferase.luciferyl-AMP+$PP_i$ luciferase.luciferyl-AMP+$O_2$—luciferase+oxyluciferin+AMP+$CO_2$+hv 1.2 Method of detecting secreted alkaline phosphatase Alkaline phosphatase is an enzyme which catalyzes the hydrolysis of bound phosphate. The membrane-located enzyme occurring in eukaryotes possesses a glycophospholipid anchor by which it is bound to the membrane by its C-terminal end. Since secreted proteins are often more convenient to detect than are those which are located internally with the cell or in the membrane, an artificial translation termination signal was introduced into the sequence of alkaline phosphatase from human placenta (513 amino acids) at position 489 (Berger et al., 1988). The protein mutant produced following transfection of the corresponding expression plasmid is efficiently secreted into the medium and is outstandingly suitable for use as a reporter molecule (SEAP=secreted alkaline phosphatase). It can be detected calorimetrically or luminometrically (Berger et al., 1988).

1.3 Preparation of transformed BHK cells

The monocistronic and bicistronic expression vectors, which carry the coding sequences of the reporter genes LUC and SEAP or the PDGF-A and PDGF-B chains (c.f. FIGS. 2A–C and 6A–C), were transfected by the calcium phosphate precipitation technique into BHK cells (Wigler et al., 1979; Graham & van der Eb, 1973). A day before the transfection, 2–3×10$^5$ BHK cells/24 cm$^2$ were transferred into new culture flasks. Four hours prior to the transfection, a media change was carried out using DME medium. 5 μg of the abovementioned plasmid DNA, and 0.5 μg of the selection plasmids pAG60 and pSV2pac (Colbére-Garapin, 1981; Vara et al., 1986), which encode a neomycin resistance gene and puromycin resistance, respectively, were suspended together in 250 μl of 250 mM $CaCl_2$. The solution was slowly added, while continuously agitating by blowing in sterile air, to 250 μl of 2×HEPES buffer (280 mM NaCl; 50 mM HEPES; 1.5 mM $NaH_2PO_4$, pH 7.1), and the resulting precipitate was added to the nutrient medium. Two days after the transfection, selection for stably transfected cells was begun by changing the medium from DME medium to double selection medium (5 μg/ml puromycin;

500 μg/ml G418) (Wirth et al., 1988). Representative clones of the PDGF-producing or LUC/SEAP-producing BHK cells were deposited with the DSM on the 11.8.1992 as follows:

-pSBC-PDGF-A/-G-B190=DSM ACC2048
-pSBC-PDGF-B190/-G-A=DSM ACC2049
-pSBC-SEAP/-G-LUC=DSM ACC2046
-pSBC-G-SEAP/LUC=DSM ACC2047

1.4 Expression of equimolar quantities of the gene products LUC and SEAP as a result of introducing a translation-augmenting sequence prior to the IRES-regulated cistron The results of the investigations with the reporter gene constructs pSBC-LUC/SEAP and pSBC-SEAP/LUC in Tab. 1 demonstrate that expression of the IRES-dependent-translation in the bicistronic construct is always clearly less than that in the cistron translated in a cap-dependent manner. This corresponds to the values known from the literature. The β-globin sequence from *Xenopus laevis* (SEQ ID NO: 6) was inserted into the unique NotI cleavage site in the monocistronic and bicistronic reporter gene constructs (FIG. 2C). In the bicistronic expression vectors, it is located directly between the promoter and the 5'UTR of the first cistron or between the IRES element and the 5'UTR of the second cistron.

Augmentation of the translation efficiency of the individual cistrons was measured with the aid of reporter gene constructs as depicted in FIGS. 2A–2C. Table 1 shows that the β-globin sequence stimulates the cap-dependent translation of luciferase in the monocistronic expression unit by a factor of 5 and the IRES-dependent translation in bicistronic expression units by a factor of 3. The latter leads to equimolar expression of cistrons 1 and 2 in bicistronic vectors. The Northern blot depicted in Table 1 shows that the corresponding gene products are read off from a monocistronic and a bicistronic mRNA, respectively. The fact that the specific mRNA concentrations are of the same order of magnitude in the cells proves that the expression-augmenting effect of the globin sequence is realized at the level of translation.

Equimolar expression of the gene products of the first and second cistrons was achieved by introducing the 5'UTR of the globin gene from *Xenopus laevis* (SEQ ID NO: 6).

Example 2

Expression of PDGF-AB Heterodimer Using the Bicistronic Vector System 2.1 Preparation of conditioned cell culture supernatants The BHK cells were transformed in analogy with 1.3. After counting the colonies, the cells are trypsinized off, taken up in fresh selection medium and adjusted to a cell count of $10^5$ cells/ml. In each case, 10 ml of this cell suspension are transferred into a flask having a floor area of 65 cm² and cultivated for a further 24 h. The medium is then removed, the cell lawn washed twice with PBS, and the medium replaced with 10 ml of production medium (DMEM, without serum and selective antibiotics). After 24 h, the medium is taken off. The harvested supernatants are stored until analysis at −20° C. The cells are counted and stored in liquid nitrogen. At the time of harvesting, the cell count/flask is $0.8–1.2 \times 10^7$.

2.2 Detection of PDGF in the culture supernatants using the mitogen test

The mitogenic activity of PDGF can be determined by measuring the stimulation of the rate of DNA synthesis in density-arrested fibroblasts. This does not permit differentiation of the isoforms, since all the PDGF species are biologically active in this test.

The assay was carried out in accordance with Shipley et al., (1984) using AKR-2B mouse fibroblasts in 24-well plates. In this test, pure PDGF demonstrates half-maximum stimulation at a concentration of about 5 ng/ml. This value was employed in order to determine productivities. The results of the mitogen test are compared with the values from the PDGF-AB-ELISA in Tab. 2.

2.3 Detection of PDGF-AB heterodimer in the culture supernatants using PDGF ELISAs Two 'two-antibody sandwich assays' were constructed which permit I.) rough quantification of the PDGF-A and PDGF-B chains in PDGF dimers and II.) specific quantification of PDGF-AB in the presence of PDGF-AA and PDGF-BB.

I. Sandwich Assay using two polyclonal anti-PDGF antibodies 96-well polystyrene plates (from Dynatech, U-Platte, No. M124B) are coated in the following sequence (in each case 4 washings with PBS containing 0.05% Tween 20 between each step):

I.1 Polyclonal goat anti-PDGF-AB-IgG (from Collaborative Research, No. 40017); binds PDGF-AB, PDGF-BB and, to a small extent, PDGF-AA), 2 μg/ml in 0.05 M carbonate/bicarbonate buffer, 50 μl at 4° C. overnight I.2 % BSA (from E. Merck, No. 12018) in PBS, pH 7.5, 100 μl at R.T. for 1 h.

I.3 PDGF-containing solutions, diluted in PBS containing 0.1% BSA and 0.05% Tween 20 (PBS+), 50 μl at R.T. for 1 h.

I.4.1 Polyclonal rabbit anti-PDGF-AA-IgG (from Genzyme, No. ZP-214, binds to the A chain of dimeric PDGF), 2 μg/ml in PBS+, 50 μl at R.T. for 1 h; (ELISA I.1) or I.4.2 Polyclonal rabbit anti-PDGF-BB-IgG (from Genzyme, No. ZP-215, binds to the B chain of dimeric PDGF), as I.4.1 (ELISA I.2)

I.5 POD-labelled goat anti-rabbit IgG (from Pierce, No. 31460), 0.1 μg/ml in PBS+, 50 μl at R.T. for 1 h, detection using the substrate tetramethylbenzidine in accordance with E. S. BOS et al. (J. Immunoassay 2 (1981), 187–204).

II. Sandwich assay using a monoclonal and a polyclonal anti-PDGF antibody

The same plates as in ELISA I are coated in the following sequence (quantities, buffers and incubation times as above):

II.1 Sheep anti-mouse IgG (from Boehringer Mannheim, No. 1097 105), 3 μg/ml.

II.2 1% BSA in PBS

II.3 Mouse hybridoma supernatant from clone 1B3 [obtained by fusing SP2/O-myeloma cells with spleen cells from mice which had been immunized with recombinant PDGF-AB (from *E. coli* in accordance with J. Hoppe et al., 1990)], 2 μg/ml IgG2a. The monoclonal antibody binds specifically to the B chain of PDGF dimers.

II.4 ⁻PDGF-containing solutions

II.5 Polyclonal rabbit anti-PDGF-AA-IgG (see I.4.1), 2 μg/ml

II.6 as I.5

2.4 Expression of equimolar quantities of the PDGF A and B chains as a result of introducing a translation-augmenting sequence prior to the IRES-regulated cistron Bicistronic constructs containing the PDGF-B which was mutated as described in FIG. 5 would normally lead to expression of the PDGF A and B chains in the ratio 3:1, corresponding to the arrangement in the bicistronic vector. Equimolar expression of the two genes was achieved by introducing translation-augmenting sequences into the 3' region of the internal ribosomal entry site of the polio element. Such an element is, for example, the β-globin isoforms (PDGF-AA, PDGF-AB or PDGF-BB). The specific proportion of heterodimeric PDGF-AB can be determined by the PDGF-AB specific ELISA II. The percentage proportion of PDGF homodimers can be determined with a high degree of accuracy from the difference between the result of the mitogen test and that of this latter analysis.

TABLE 1

*$10^6$ BHK cells sequence from *Xenopus laevis* (SEQ ID NO: 6). This β-globin sequence (oligomer G) was inserted into the unique NotI cleavage site in the bicistronic vectors (FIG. 6C). In the resulting plasmids, it is located directly between the IRES element and the 5'UTR of the second cistron.

2.5 Results:

The results of three different analyses of PDGF from culture supernatants of recombinant BHK cells are presented in FIG. 9 and Table 2.

Using ELISA I, it is possible to make a rough estimate of the proportions of the two PDGF chains. Conclusions can therefore be drawn with regard to the efficiency of the intercistronic elements, and bicistronic constructs can be characterized in which approximately equal quantities of PDGF-A and PDGF-B are translated. However, in this context, it should be taken into account that PDGF-AB gives a stronger signal in ELISA I.1 than does PDGF-AA. The mitogen test provides a serviceable value for the total quantity of rPDGF present in the culture supernatants, without being able to differentiate between the different

TABLE 2

| Plasmid | monocis. | bicis. | Elisa* | Mitogentest* |
|---|---|---|---|---|
| pSBC-2-PDGF-A | + | − | 14.3 | 1000 |
| pSBC-2-PDGF-B | + | − | 5 | 250 |
| pSBC-PDGF-A/B | − | + | 291 | 600 |
| pSBC-PDGF-B/A | − | + | 520 | 550 |
| pSBC-2-PDGF-$B_{190}$ | + | − | 17.5 | 2000 |
| pSBC-2-PDGF-A/G-$B_{190}$ | − | + | 1020 | 1100 |
| pSBC-2-PDGF-$B_{190}$/G-A | − | + | 2550 | 2500 |
| pSBC-2-PDGF-A + B | + | − | 590 | 900 |
| pSBC-2-PDGF-G-A + G-$B_{190}$ | + | − | 380 | 1300 |

*PDGF in ng/ml $10^6$ BHK/24 h

ABBREVIATIONS:
B190 - C-terminally truncated PDGF-B precursor (DNA)
B' - PDGF-B chain (protein), originating from truncated PDGF-B precursor
BHK - Hamster cell line
bp - Base pair(s)
BSA - Bovine serum albumin
CHO - Hamster cell line DMEM - Dulbecco's modified Eagle medium
ELISA - Enzyme-linked immunosorbent assay
G - β-globin sequence from *Xenopus laevis*
IgG - Class G immunoglobulin
IRES - Internal ribosomal entry site
LUC - Luciferase
nt - Nucleotide(s)
PBS - Phosphate-buffered sodium chloride solution
PCR - Polymerase chain reaction
PDGF - Platelet-derived growth factor
SEAP - Secreted alkaline phosphatase
UTR - Untranslated region

LITERATURE

Adam M. A., Ramesh N., Miller A. D., and Osborne W. R. A. (1991) J. Virol. 65, 4985–4990.
Artelt P., Morelle C., Ausmeier M., Fitzek M., and Hauser H. (1988) Gene 68, 213–219.
Beckmann M. P., Betsholtz C., Heldin C. -H., Westermark B., Di Marco E., Di. Fiore P. P., Robbins K. C., and Aaronson S. A. (1988) Science 241, 1344–1349.
Berger J., Hauber J., Hauber R., Geiger R., Cullen B. R. (1988) Gene 66, 1–10.
Berkner K. L. and Sharp P. A. (1985) Nucl. Acids Res. 13, 841–857.
Betsholtz C., Johnsson A., Heldin C. -H., Westermark B., Lind P., Urdea M. S., Eddy R., Shows T. B., Philpott K., Mellor A. L., Knott T. J., and Scott J. (1986) Nature 320, 695–699.
Block L. H., Ebmmons L. R., Vogt E., Sachinidis A., Vetter W., and Hoppe J. (1989) Proc. Natl. Acad. Sci. USA 86, 2388–2392.
Boel E., Berkner K. L., Nexoe B. A., and Schwartz T. W. (1987) FEBS Lett. 219, 181–188.
Bywater M., Rorsman F., Bongcam-Rudloff E., Hark G., Hammacher A., Heldin C. -H., Westermark B., and Betsholtz C. (1988) Mol. Cell. Biol. 8, 2753–2762.
Colbére-Garapin F., Horodniceanu F., Kourilsky P., and Garapin A. C. (1981) J. Mol. Biol. 150, 1–14.
de Wet, J. R., Wood K. V., DeLuca M., Helinski D. R. and Subramani S. (1987) Mol. Cell. Biol. 7, 725–737.
Eichner W., Jäger V., Herbst D., Hauser H. and Hoppe J. (1989) Eur. J. Biochem. 185, 135–140.
Falcone D., and Andrews D. W. (1991) Mol. Cell. Biol. 11 (5), 2656–2664.
Gallie D. R., Sleat D. E., Watts J. W., Turner P. C. and Wilson T. M. A. (1987A) Nucl. Acids Res. 15, 3257–3272.
Gallie D. R., Sleat D. E., Watts J. W., Turner P. C. and Wilson T. M. A. (1987B) Nucl. Acids Res. 15, 8692–8711.
Gallie D. R., Sleat D. E., Watts J. W., Turner P. C. and Wilson T. M. A. (1988) Nucl. Acids Res. 16, 883–893.
Ghattas I. R., Sanes J. R., and Majors J. E. (1991) Mol. Cell. Biol. 22, 5848–5859.
Graham F., and van der Eb L. (1973) Virology 52, 456–487.
Hambidge S. J., and Sarnow P. (1991) J. Virol. 65, 6312–6315.
Hammacher A., Hellmann U., Johnsson A., Östman A., Gunnarsson K., Westermark B., Wasteson Å., and Heldin C. -H. (1988) J. Biol. Chem. 263, 16493–16499.
Hart C. E., Forstrom J. W., Kelly J. D., Seifert R. A., Smith R. A., Ross R., Murray M. J., and Bowen-Pope D. F. (1988) Science 240, 1529–1531.
Hart C. E., Bailey M., Curtis D. A., Osborn S., Raines E., Ross R., and Forstrom J. W. (1990) Biochemistry 29, 166–172.
Heldin C. -H., Johnsson A., Wennergren S., Wernstedt C., Betsholtz C., and Westermark B. (1986) Nature 319, 511–514.
Heldin C. -H., Bäckström G., Östman A., Hammacher A., Rönnstrand L., Rubin K., Nister M., and Westermark B. (1988) EMBO J. 7, 1387–1393.
Hoppe J., Schumacher L., Eichner W. and Weich H. A. (1987), FEBS Lett. 223, 243–246.
Hoppe J., Weich H. A., and Eichner W. (1989) Biochemistry 28, 2956–2960.
Hoppe J., Weich H. A., and Eichner W., and Tatje D. (1990) Eur. J. Biochem. 187, 207–214.
Hosang M., Rouge M., Wipf B., Eggiman B., Kaufmann F., and Hunziker W. (1989) J. Cell. Physiol. 149, 558–564.
Jackson R. J., Howell M. T., and Kaminski A. (1990) Trends Biochem chem. Sci. 15, 477–483.
Jang S. K., Kräusslich H., Nicklin M. J. H., Duke G. M., Palmenberg A. C., and Wimmer E. (1988) J. Virol. 62, 2636.
Jang S. K., Davies M. V., Kaufmann R. J., and Wimmer E. (1989) J. Virol. 63 (4), 1651–1660.
Jang S. K., and Wimmer E. (1990) Genes Dev. 4, 1560–1572.
Jobling S. A. and Gehrke L. (1987) Nature 325, 622–625.
Johnsson A., Heldin C. -H., Wasteson A., Westermark B., Deuel T. F., Huang J. S., Seeburg P. H., Gray A., Ullrich A., Scrace G., Stroobant P., Waterfield M. D. (1984) EMBO J. 136, 921–928.
Kaufman R. J. (1985) Proc. Natl. Acad. Sci. (USA) 82, 689–693.
Kaufman R. J., Murtha P., and Davies M. V. (1987) EMBO J. 6, 187–193.
Kaufman R. J., Davies M. V. Wasley L. C., and Michnick D. (1991) Nucleic Acids Res. 19, 4485–4490.
Kelly J. D., Raines E. W., Ross R., and Murray M. J. (1985) EMBO J. 4, 3399–3405.
Klausner R. D. and Harford J. B. (1989) Science 246, 870–872.
Knoechel W., Korge E., Basner A., and Meyerhof W. (1986) J. Mol. Evol. 23, 211–223.
Kozak M. (1987) Mol. Cell. Biol. 7 (10), 3438–3445.
Kozak M. (1989) Mol. Cell. Biol. 9, 5134–5142.
La Rochelle W. J., Giese N., May-Siroff M., Robbins K. C., and Aaronson S. A. (1990) Science 248, 1541–1544.
La Rochelle W. J., May-Siroff M., Robbins K. C., and Aaronson S. A. (1991) Genes & Development 5, 1191–1199.
Lehrach H., Diamond D., Wozney J. M., and Boedtker H. (1977) Biochemistry 16, 4743–4751.
Macejak D. G., and Sarnow P. (1991) Nature (London) 353, 90–94.
Matoskova B., Rorsman F., Svensson V. and Betsholtz C. (1989), Mol. Cell. Biol. 9, 3148–3150.
Meerovitch K., Pelletier J., and Sonenberg N. (1989) Genes Dev. 3, 1026–1034.
Millan, J. L. (1986) J. Biol. Chem. 261, 3112–3115
Nakamaye K. and Eckstein F. (1986) Nucl. Acids Res. 14, 9679–9698.
Nister M., Hammacher A., Mellström K., Siegbahn A., Rönnstrang L., Westermark B., and Heldin C. -H. (1988); Cell 52, 791–799.
Östman A., Rall L., Hammacher A., Wormstead M. A., Coit D., Valenzuela P., Betsholtz C., Westermark B., and Heldin C. -H. (1988) J. Biol. Chem. 263, 16202–16208.
Östman A., Andersson M., Betsholtz C., Westermark B., and Heldin C. -H. (1991) Cell Regulation 2, 503–512.
Patient R. K., Harris R., Walmsley M. E. and Williams J. G. (1983) J. Biol. Chem. 258, 8521–8523.

Pelletier J., and Sonenberg N. (1988) Nature 334, 320.
Purchio A. F. and Fareed G. C. (1979) J. Virol. 29, 763–769.
Ratner L., Josephs S. F., Jarrett R., Reitz M. S. and Wong-Staal F. (1985), Nucl. Acids Res. 13, 5007–5018.
Reilly C. F. and Broski J. E. (1989) Biochem. Biophys. Res. Commun. 160, 1047–1054.
Robbins K. C., Leal F., Pierce J. H., and Aaronson S. A. (1985) EMBO J. 4, 1783–1792.
Sachinidis A., Locher R., Vetter W., Tatje D., and Hoppe J. (1990) J. Biol. Chem. 265, 10238–10243.
Sachinidis A., Locher R., Hoppe J., and Vetter W. (1990) FEBS Lett. 275, 95–98.
Sarnow P. (1989) J. Virol. 63, 467–470.
Sayers J. R., Schmidt W. and Eckstein F. (1988) Nucl. Acids Res. 16, 791–802.
Shipley G. D., Childes C. B., Volkenant M. E. and Moses H. L. (1984) Cancer Res. 44, 710–716.
Siegbahn A., Hammacher A., Westermark B., and Heldin C.-H. (1990) J. Clin. Invest. 85, 916–920.
Simoes E. A. F., and Sarnow P. (1991) J. Virol. 65, 913–921.
Stroobant P., and Waterfield M. D. (1984) EMBO J. 3, 2963–2967.
Taylor J. W., Ott J. and Eckstein F. (1985) Nucl. Acids Res. 13, 8764–8785.
Vara J., Portela A., Oritin J. and Jimenez A. (1986) Nucl. Acids Res. 14, 4617–4624.
Weich H. A., Sebald W., Schairer H. U., and Hoppe J. (1986), FEBS Lett. 198, 344–348.
Wigler M., Sweet R., Sim G. K., Wold B., Pellicer A., Lacy E., Maniatis T., Silverstein S., and Axel R. (1979) Cell 16, 777–785.
Wirth M., Bode J., Zettlmeiβ1 G., and Hauser H. (1988) Gene 73, 419–426.
Wirth M., Schumacher L., and Hauser H. (1991) In Modern Approaches to Animal Cell Technology, Griffiths B., Spier R., and Meigner R., eds. Butterworths), pp. 338–343.
Wise R. J., Orkin S. H. and Collins T. (1989) Nucl. Acids Res. 17, 6591–6601.
Wood C. R., Morris G. E., Alderman E. M., Fouser L., and Kaufman R. J. (1991) Proc. Natl. Acad. Sci. USA 88, 8006–8010.
Young R. M., Mendoza A. E., Collins T. and Orkin S. H. (1990) Mol. Cell. Biol. 10, 6051–6054.

We claim:

1. Host cell which is a PDGF-AB producing BHK which is one of the clones 92-22-6, corresponding to DSM ACC 2048, or 92-22-7, corresponding to DSM ACC 2049, and has been transformed with an expression vector containing a multi-cistronic expression unit for the equimolar expression of polypeptides or subunits thereof in mammalian cells as host cells, characterized by the general formula p-5'UTR-$C_1$-(IRES-Y-$Cam_2$)$_n$-3'UTR-polyA, in which "p" is a transcriptional promoter,
      "5'UTR' is an untranslated nucleotide sequence,
      n is 1,
      "$C_1$" and "$C_2$" are cistrons which alternatively contain a gene encoding the A or B chain of PDGF or a biologically active analog or a fragment thereof, both genes being represented simultaneously in the expression unit,
      "IRES" is the polio virus type 1 UTR according to SEQ ID NO:5.
      "Y" is the β-globin sequence from *Xenopus laevis* according to SEO ID NO:6,
      "3'UTR" is an untranslated nucleotide sequence, and
      "polyA" is a polyadenylation signal.

2. Host cell which is the clone 91-46-9, corresponding to DSM ACC 2046, and has been transformed with an expression vector containing a multicistronic expression unit for the equimolar expression of polypeptides or subunits thereof in mammalian cells as host cells, characterized by the general formula p-5'UTR-$C_1$-(IRES-Y-$C_2$)$_n$-3'UTR-polyA, in which "p" is a transcriptional promoter,
      "5'UTR" is an untranslated nucleotide sequence,
      n is 1, "$C_1$" and "$C_2$" are cistrons which in each case contain a gene encoding a polypeptide or its subunit, and $C_1$ and $C_2$ contain reporter genes which are different from each other, "IRES" is a nucleotide sequence of viral, cellular or synthetic origin, which at the stage of translation is responsible for internal initiation, "Y" is a nucleotide sequence which, in energy with IRES, ensures expression of the gene(s) contained in $C_2$ in such a manner that the gene products of $C_1$ and $C_2$ are expressed in equimolar quantities, "3'UTR" is an untranslated nucleotide sequence, and "polyA" is a polyadenylation signal.

3. Multicistronic expression unit for the equimolar expression of polypeptides or subunits thereof in mammalian cells as host cells, characterized by the general formula p-5'UTR-$C_1$-(IRES-Y-$C_2$)$_n$-3'UTR-polyA, in which "p" is a transcriptional promoter, "5'UTR" is an untranslated nucleotide sequence, n is 1, 2 or 3, "$C_1$" and "$C_2$" are cistrons which in each case contain a gene encoding a polypeptide or its subunit, wherein, if n is 2 or 3, the sequences of the successive groups (IRES-Y-$C_2$) may be equal or different amongst each other, and further $C_1$ and $C_2$ may be equal or different, "IRES" is the 5'UTR of polio virus type 1, of encephalomyocarditis virus (EMV), of "Theiler's murine encephalomyelitis virus" (TMEV), of "bovine enterovirus" (BEV), of "coxsackie B virus" (CBV), or of "human rhinovirus" (HRV), or the "human immunoglobulin heavy chain binding protein" (BIP) 5'UTR, the *Drosophila antennapediae* 5'UTR or the *Drosphila ultrabithorax* 5'UTR, or genetic hybrids or fragments from the above listed sequences, "Y" is the β-globin sequence from *Xenopus laevis,* the alfalfa mosaic virus RNA4 5'UTR, ferritin 5'UTR (animal), tobacco mosaic virus 5'UTR (omega), or their leader mutants, turnip yellow mosaic virus (TYMV), brome mosaic virus (BMV) RNA3 5'UTR, *Rous sarcoma* virus (RSV) 5'UTR, adenovirus tripartite leader (L1–3) and variants thereof, *Xenopus borealis* 5'UTR β-globin sequence or *Xenopus tropicalis* 5'UTR β-globin sequence which, in synergy with IRES, ensures expression of the gene(s) contained in $C_2$ in such a manner that the gene products of $C_1$ and $C_2$ are expressed in equimolar quantities, "3'UTR" is an untranslated nucleotide sequence, and "polyA" is a polyadenylation signal.

4. A host cell comprising an expression unit of claim 3.

5. Process for preparing proteins consisting of equimolar proportions of polypeptide subunits, characterized in that host cells according to claim 4 are cultivated in a suitable medium and the resulting protein is separated off from the cells and the medium.

6. The process according to claim 5 wherein $C_1$ and $C_2$ comprise genes encoding subunits of heteromeric proteins.

7. The process according to claim 5, wherein $C_1$ and $C_2$ encode factor VIII, creatine kinase, haemoglobin, an immunoglobulin, a histocompatibility antigen, scatter factor (HGF-SF), a member of the transforming growth factor type β family, bone morphogenic protein (BMF), a member of the integrin family, or PDGF, or a natural or synthetic variant or a derivative thereof.

8. The multicistronic expression unit according to claim 3, characterized in that $C_1$ and $C_2$ in each case contain genes which encode polypeptide subunits of single or heteromeric proteins.

9. The multicistronic expression unit according to claim 3, characterized in that $C_1$ and $C_2$ in each case contain genes which encode the different subunits of factor VIII, creatine kinase, haemoglobin, immunoglobulins, histo-compatibility antigens, scatter factor (HGF-SF), members of the transforming growth factor type β family, of bone morphogenic protein (BMP), members of the integrin family, or PDGF, or their natural or synthetic variants and derivatives.

10. The multicistronic expression unit according to claim 3, characterized in that "n" is 1 and $C_1$ and $C_2$, alternatively contain a gene encoding the A or B chain of PDGF, or a biologically active analog or a fragment thereof, both genes being represented simultaneously in the expression unit.

11. The multicistronic expression unit according to claim 10, characterized in that $C_1$ or $C_2$ contains the PDGF-$A_g$ (SEQ ID NO: 1) or the PDGF-$A_L$ precursor sequence.

12. The multicistronic expression unit according to claim 10, characterized in that $C_1$ or $C_2$ contains the complete PDGF-B precursor sequence (SEQ ID NO: 3), the v-sis gene from simian sarcoma virus, or variants of these sequences.

13. The multicistronic expression unit according to claim 10, characterized in that $C_1$ or $C_2$ contains a gene fragment which encodes a PDGF-B precursor molecule which is truncated by replacing the arginine-encoding codon in amino acid protein 191 by translation stop codon (SEQ ID NO: 24).

14. The multicistronic expression unit according to claim 10, characterized in that $C_1$ and $C_2$ alternatively contain the PDGF-$A_g$ sequence (SEQ ID NO: 1) or the truncated PDGF-B190 precursor sequence (SEQ ID NO: 24), and both genes are represented simultaneously in the expression unit.

15. The multicistronic expression unit according to claim 3, characterized in that "n" is 1 and $C_1$ and $C_2$ contain reporter genes which are different from each other.

16. The multicistronic expression unit according to claim 15, characterized in that the reporter genes encode luciferase and secretory alkaline phosphatase.

17. The process for preparing heteromeric rPDGF-AB, characterized in that host cells comprising an expression unit of claim 3, in which "n" is 1 and $C_1$ and $C_2$, alternatively contain a gene encoding the A or B chain of PDGF, or a biologically active analog or a biologically active fragment thereof, both genes being represented simultaneously in the expression unit, are cultivated in a suitable medium and the resulting rPDGF-AB is separated off from the cells and the medium.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH: 748 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: pODA (Eichner et al., 1989)

(ix) FEATURE:
        (A) NAME/KEY: CDS
        (B) LOCATION: 95..682
        (D) OTHER INFORMATION: /product= "PDGF-A precursor sequence
            (short splice form)"
            /note= "human PDGF-A gene (short splice form, [2])
            from pODA, flanked by 5'-EcoRI and 3'-HindIII
            restriction cleavage sites"
            /citation= ([2])

(ix) FEATURE:
        (A) NAME/KEY: mat_peptide
        (B) LOCATION: 353..682
        (D) OTHER INFORMATION: /product= "mature PDGF-A chain"

(x) PUBLICATION INFORMATION:
        (A) AUTHORS: Eichner, W.
            Jaeger, V.
            Herbst, D.
            Hauser, H.
            Hoppe, J.
        (C) JOURNAL: Eur. J. Biochem.
        (D) VOLUME: 185
        (F) PAGES: 135-140
        (G) DATE: 1989

(x) PUBLICATION INFORMATION:
  (A) AUTHORS: Hoppe, J.
       Schumacher, L.
       Eichner, W.
       Weich, H. A.
  (C) JOURNAL: FEBS Lett.
  (D) VOLUME: 223
  (F) PAGES: 243-246
  (G) DATE: 1987

(xi) SEQUENCE DESCRIPTION: SEQ ID NO: 1:

```
GAATTCCCAC TGAATTTCGC CGCCACAGGA GACCGGCTGG AGCGCCCGCC CCGCGCCTCG           60

CCTCTCCTCC GAGCAGCCAG CGCCTCGGGA CGCG ATG AGG ACC TTG GCT TGC             112
                                    Met Arg Thr Leu Ala Cys
                                    -86 -85

CTG CTG CTC CTC GGC TGC GGA TAC CTC GCC CAT GTT CTG GCC GAG GAA           160
Leu Leu Leu Leu Gly Cys Gly Tyr Leu Ala His Val Leu Ala Glu Glu
-80             -75                 -70                 -65

GCC GAG ATC CCC CGC GAG GTG ATC GAG AGG CTG GCC CGC AGT CAG ATC           208
Ala Glu Ile Pro Arg Glu Val Ile Glu Arg Leu Ala Arg Ser Gln Ile
                -60                 -55                 -50

CAC AGC ATC CGG GAC CTC CAG CGA CTC CTG GAG ATA GAC TCC GTA GGG           256
His Ser Ile Arg Asp Leu Gln Arg Leu Leu Glu Ile Asp Ser Val Gly
            -45                 -40                 -35

AGT GAG GAT TCT TTG GAC ACC AGC CTG AGA GCT CAC GGG GTC CAC GCC           304
Ser Glu Asp Ser Leu Asp Thr Ser Leu Arg Ala His Gly Val His Ala
        -30                 -25                 -20

ACT AAG CAT GTG CCC GAG AAG CGG CCC CTG CCC ATT CGG AGG AAG AGA           352
Thr Lys His Val Pro Glu Lys Arg Pro Leu Pro Ile Arg Arg Lys Arg
    -15                 -10                  -5

AGC ATC GAG GAA GCT GTC CCC GCT GTC TGC AAG ACC AGG ACG GTC ATT           400
Ser Ile Glu Glu Ala Val Pro Ala Val Cys Lys Thr Arg Thr Val Ile
1                5                  10                  15

TAC GAG ATT CCT CGG AGT CAG GTC GAC CCC ACG TCC GCC AAC TTC CTG           448
Tyr Glu Ile Pro Arg Ser Gln Val Asp Pro Thr Ser Ala Asn Phe Leu
            20                  25                  30

ATC TGG CCC CCG TGC GTG GAG GTG AAA CGC TGC ACC GGC TGC TGC AAC           496
Ile Trp Pro Pro Cys Val Glu Val Lys Arg Cys Thr Gly Cys Cys Asn
        35                  40                  45

ACG AGC AGT GTC AAG TGC CAG CCC TCC CGC GTC CAC CAC CGC AGC GTC           544
Thr Ser Ser Val Lys Cys Gln Pro Ser Arg Val His His Arg Ser Val
    50                  55                  60

AAG GTG GCC AAG GTG GAA TAC GTC AGG AAG AAG CCA AAA TTA AAA GAA           592
Lys Val Ala Lys Val Glu Tyr Val Arg Lys Lys Pro Lys Leu Lys Glu
65                  70                  75                  80

GTC CAG GTG AGG TTA GAG GAG CAT TTG GAG TGC GCC TGC GCG ACC ACA           640
Val Gln Val Arg Leu Glu Glu His Leu Glu Cys Ala Cys Ala Thr Thr
                85                  90                  95

AGC CTG AAT CCG GAT TAT CGG GAA GAG GAC ACG GAT GTG AGG                   682
Ser Leu Asn Pro Asp Tyr Arg Glu Glu Asp Thr Asp Val Arg
            100                 105                 110

TGAGGATGAG CCGCAGCCCT TTCCTGGGAC ATGGATGTGG GGATCCGTCG ACCTGCAGCC         742

AAGCTT                                                                    748
```

(2) INFORMATION FOR SEQ ID NO: 2:

(i) SEQUENCE CHARACTERISTICS:
       (A) LENGTH: 196 amino acids
       (B) TYPE: amino acid
       (D) TOPOLOGY: linear (ii) MOLECULE TYPE: protein (xi) SEQUENCE DESCRIPTION: SEQ ID NO: 2:

Met Arg Thr Leu Ala Cys Leu Leu Leu Gly Cys Gly Tyr Leu Ala
-86 -85             -80                 -75

His Val Leu Ala Glu Glu Ala Glu Ile Pro Arg Glu Val Ile Glu Arg
-70             -65             -60                 -55

Leu Ala Arg Ser Gln Ile His Ser Ile Arg Asp Leu Gln Arg Leu Leu
                -50                 -45             -40

Glu Ile Asp Ser Val Gly Ser Glu Asp Ser Leu Asp Thr Ser Leu Arg
            -35             -30                 -25

Ala His Gly Val His Ala Thr Lys His Val Pro Glu Lys Arg Pro Leu
        -20             -15             -10

Pro Ile Arg Arg Lys Arg Ser Ile Glu Glu Ala Val Pro Ala Val Cys
    -5              1               5                   10

Lys Thr Arg Thr Val Ile Tyr Glu Ile Pro Arg Ser Gln Val Asp Pro
                15              20                  25

Thr Ser Ala Asn Phe Leu Ile Trp Pro Pro Cys Val Glu Val Lys Arg
            30              35              40

Cys Thr Gly Cys Cys Asn Thr Ser Ser Val Lys Cys Gln Pro Ser Arg
            45              50              55

Val His His Arg Ser Val Lys Val Ala Lys Val Glu Tyr Val Arg Lys
        60              65              70

Lys Pro Lys Leu Lys Glu Val Gln Val Arg Leu Glu Glu His Leu Glu
75              80              85                  90

Cys Ala Cys Ala Thr Thr Ser Leu Asn Pro Asp Tyr Arg Glu Glu Asp
                95              100             105

Thr Asp Val Arg
            110

(2) INFORMATION FOR SEQ ID NO: 3:

(i) SEQUENCE CHARACTERISTICS:
        (A) LENGTH: 868 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: pMVW-2 (Weich et al., 1986)

(ix) FEATURE:
        (A) NAME/KEY: CDS
        (B) LOCATION: 40..762
        (D) OTHER INFORMATION: /product= "PDGF-B
            precursor sequence"
            /note= "human PDGF-B gene from pGEM2-PDGF-B,
            flanked by 5'-EcoRI und 3'-HindIII
            restriction cleavage sites"

(ix) FEATURE:
        (A) NAME/KEY: mat_peptide
        (B) LOCATION: 283..609
        (D) OTHER INFORMATION: /product= "mature PDGF-B chain"

(x) PUBLICATION INFORMATION:
        (A) AUTHORS: Weich, H. A.
            Sebald, W.
            Schairer, H. U.
            Hoppe, U.
        (C) JOURNAL: FEBS Lett.

(D) VOLUME: 198
        (F) PAGES: 344-348
        (G) DATE: 1986

(xi) SEQUENCE DESCRIPTION: SEQ ID NO: 3:

GAATTCGAGC TCGCCCGGGG ATCCTCTAGA GTCGACACC ATG AAT CGC TGC TGG             54
                                           Met Asn Arg Cys Trp
                                           -81 -80

GCG CTC TTC CTG TCT CTC TGC TGC TAC CTG CGT CTG GTC AGC GCC GAG          102
Ala Leu Phe Leu Ser Leu Cys Cys Tyr Leu Arg Leu Val Ser Ala Glu
    -75                 -70                 -65

GGG GAC CCC ATT CCC GAG GAG CTT TAT GAG ATG CTG AGT GAT CAC TCG          150
Gly Asp Pro Ile Pro Glu Glu Leu Tyr Glu Met Leu Ser Asp His Ser
-60                 -55                 -50                 -45

ATC CGC TCC TTT GAT GAT CTC CAA CGC CTG CTG CAC GGA GAC CCC GGA          198
Ile Arg Ser Phe Asp Asp Leu Gln Arg Leu Leu His Gly Asp Pro Gly
                -40                 -35                 -30

GAG GAA GAT GGG GCC GAG TTG GAC CTG AAC ATG ACC CGC TCC CAC TCT          246
Glu Glu Asp Gly Ala Glu Leu Asp Leu Asn Met Thr Arg Ser His Ser
            -25                 -20                 -15

GGA GGC GAG CTG GAG AGC TTG GCT CGT GGA AGA AGG AGC CTG GGT TCC          294
Gly Gly Glu Leu Glu Ser Leu Ala Arg Gly Arg Arg Ser Leu Gly Ser
        -10                  -5                  1

CTG ACC ATT GCT GAG CCG GCC ATG ATC GCC GAG TGC AAG ACG CGC ACC          342
Leu Thr Ile Ala Glu Pro Ala Met Ile Ala Glu Cys Lys Thr Arg Thr
  5                  10                 15                  20

GAG GTG TTC GAG ATC TCC CGG CGC CTC ATA GAC CGC ACC AAC GCC AAC          390
Glu Val Phe Glu Ile Ser Arg Arg Leu Ile Asp Arg Thr Asn Ala Asn
                25                  30                  35

TTC CTG GTG TGG CCG CCC TGT GTG GAG GTG CAG CGC TGC TCC GGC TGC          438
Phe Leu Val Trp Pro Pro Cys Val Glu Val Gln Arg Cys Ser Gly Cys
            40                  45                  50

TGC AAC AAC CGC AAC GTG CAG TGC CGC CCC ACC CAG GTG CAG CTG CGA          486
Cys Asn Asn Arg Asn Val Gln Cys Arg Pro Thr Gln Val Gln Leu Arg
        55                  60                  65

CCT GTC CAG GTG AGA AAG ATC GAG ATT GTG CGG AAG AAG CCA ATC TTT          534
Pro Val Gln Val Arg Lys Ile Glu Ile Val Arg Lys Lys Pro Ile Phe
    70                  75                  80

AAG AAG GCC ACG GTG ACG CTG GAA GAC CAC CTG GCA TGC AAG TGT GAG          582
Lys Lys Ala Thr Val Thr Leu Glu Asp His Leu Ala Cys Lys Cys Glu
 85                  90                  95                 100

ACA GTG GCA GCT GCA CGG CCT GTG ACC CGA AGC CCG GGG GGT TCC CAG          630
Thr Val Ala Ala Ala Arg Pro Val Thr Arg Ser Pro Gly Gly Ser Gln
                105                 110                 115

GAG CAG CGA GCC AAA ACG CCC CAA ACT CGG GTG ACC ATT CGG ACG GTG          678
Glu Gln Arg Ala Lys Thr Pro Gln Thr Arg Val Thr Ile Arg Thr Val
            120                 125                 130

CGA GTC CGC CGG CCC CCC AAG GGC AAG CAC CGG AAA TTC AAG CAC ACG          726
Arg Val Arg Arg Pro Pro Lys Gly Lys His Arg Lys Phe Lys His Thr
        135                 140                 145

CAT GAC AAG ACG GCA CTG AAG GAG ACC CTT GGA GCC TAGGGGCATC               772
His Asp Lys Thr Ala Leu Lys Glu Thr Leu Gly Ala
    150                 155                 160

GGCAGGAGAG TGTGTGGGCA GGGTTATTTA ATATGGTATT TGCTGTATTG CCCCCATGGC        832

CCAATCGATC CCGTCGACCT GCAGGCATGC AAGCTT                                  868

(2) INFORMATION FOR SEQ ID NO: 4:

(i) SEQUENCE CHARACTERISTICS:
        (A) LENGTH: 241 amino acids

-continued (B) TYPE: amino acid
(D) TOPOLOGY: linear (ii) MOLECULE TYPE: protein (xi) SEQUENCE DESCRIPTION: SEQ ID NO: 4:

```
Met Asn Arg Cys Trp Ala Leu Phe Leu Ser Leu Cys Cys Tyr Leu Arg
-81 -80                 -75                 -70

Leu Val Ser Ala Glu Gly Asp Pro Ile Pro Glu Glu Leu Tyr Glu Met
-65                 -60                 -55                 -50

Leu Ser Asp His Ser Ile Arg Ser Phe Asp Asp Leu Gln Arg Leu Leu
                -45                 -40                 -35

His Gly Asp Pro Gly Glu Glu Asp Gly Ala Glu Leu Asp Leu Asn Met
            -30                 -25                 -20

Thr Arg Ser His Ser Gly Gly Glu Leu Glu Ser Leu Ala Arg Gly Arg
        -15                 -10                  -5

Arg Ser Leu Gly Ser Leu Thr Ile Ala Glu Pro Ala Met Ile Ala Glu
      1               5                  10                  15

Cys Lys Thr Arg Thr Glu Val Phe Glu Ile Ser Arg Arg Leu Ile Asp
                 20                  25                  30

Arg Thr Asn Ala Asn Phe Leu Val Trp Pro Pro Cys Val Glu Val Gln
             35                  40                  45

Arg Cys Ser Gly Cys Cys Asn Asn Arg Asn Val Gln Cys Arg Pro Thr
         50                  55                  60

Gln Val Gln Leu Arg Pro Val Gln Val Arg Lys Ile Glu Ile Val Arg
     65                  70                  75

Lys Lys Pro Ile Phe Lys Lys Ala Thr Val Thr Leu Glu Asp His Leu
 80                  85                  90                  95

Ala Cys Lys Cys Glu Thr Val Ala Ala Ala Arg Pro Val Thr Arg Ser
                100                 105                 110

Pro Gly Gly Ser Gln Glu Gln Arg Ala Lys Thr Pro Gln Thr Arg Val
            115                 120                 125

Thr Ile Arg Thr Val Arg Val Arg Arg Pro Pro Lys Gly Lys His Arg
        130                 135                 140

Lys Phe Lys His Thr His Asp Lys Thr Ala Leu Lys Glu Thr Leu Gly
    145                 150                 155

Ala
160
```

(2) INFORMATION FOR SEQ ID NO: 5:

(i) SEQUENCE CHARACTERISTICS:
(A) LENGTH: 628 base pairs
(B) TYPE: nucleic acid
(C) STRANDEDNESS: single
(D) TOPOLOGY: linear (vi) ORIGINAL SOURCE:
(A) ORGANISM: Poliovirus Typ 1 (Mahoney strain)

(vii) IMMEDIATE SOURCE:
(B) CLONE: pGEM3-5'Polio (M) (4708 bp), (Sarnow, 1989)

(ix) FEATURE:
(A) NAME/KEY: -
(B) LOCATION: 1..628
(D) OTHER INFORMATION: /note= "shown are the first 628 nt of the 5' non-translated region of poliovirus Typ 1 (Mahoney)"

(ix) FEATURE:
(A) NAME/KEY: -

(B) LOCATION: 610
            (D) OTHER INFORMATION: /note= "non-authentic sequence
                due to a base pair substitution from C to G
                at Location 610"

(x) PUBLICATION INFORMATION:
        (A) AUTHORS: Sarnow, P.
        (C) JOURNAL: J. Virol.
        (D) VOLUME: 63
        (F) PAGES: 467-470
        (G) DATE: 1989

(xi) SEQUENCE DESCRIPTION: SEQ ID NO: 5:

TTAAAACAGC TCTGGGGTTG TACCCACCCC AGAGGCCCAC GTGGCGGCTA GTACTCCGGT      60

ATTGCGGTAC CCTTGTACGC CTGTTTTATA CTCCCTTCCC GTAACTTAGA CGCACAAAAC     120

CAAGTTCAAT AGAAGGGGGT ACAAACCAGT ACCACCACGA ACAAGCACTT CTGTTTCCCC     180

GGTGATGTCG TATAGACTGC TTGCGTGGTT GAAAGCGACG GATCCGTTAT CCGCTTATGT     240

ACTTCGAGAA GCCCAGTACC ACCTCGGAAT CTTCGATGCG TTGCGCTCAG CACTCAACCC     300

CAGAGTGTAG CTTAGGCTGA TGAGTCTGGA CATCCCTCAC CGGTGACGGT GGTCCAGGCT     360

GCGTTGGCGG CCTACCTATG GCTAACGCCA TGGGACGCTA GTTGTGAACA AGGTGTGAAG     420

AGCCTATTGA GCTACATAAG AATCCTCCGG CCCCTGAATG CGGCTAATCC CAACCTCGGA     480

GCAGGTGGTC ACAAACCAGT GATTGGCCTG TCGTAACGCG CAAGTCCGTG GCGGAACCGA     540

CTACTTTGGG TGTCCGTGTT TCCTTTTATT TTATTGTGGC TGCTTATGGT GACAATCACA     600

GATTGTTATG ATAAAGCGAA TTGGATTG                                        628

(2) INFORMATION FOR SEQ ID NO: 6:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (vi) ORIGINAL SOURCE:
        (A) ORGANISM: Xenopus laevis (Falcone & Andrews; Patient et
            al.)

(ix) FEATURE:
        (A) NAME/KEY: -
        (B) LOCATION: 12..55
        (D) OTHER INFORMATION: /note= "beta-globin homology;
            partial sequence, flanked by restriction cleavage
            sites"

(ix) FEATURE:
        (A) NAME/KEY: -
        (B) LOCATION: 12..55
        (D) OTHER INFORMATION: /note= "The 5'-3' orientation relates
            to the insertion between polio-UTR und cistron 2 of the
            bicistronic vectors"

(x) PUBLICATION INFORMATION:
        (A) AUTHORS: Falcone, D.
            Andrews, D. W.
        (C) JOURNAL: Mol. Cell. Biol.
        (D) VOLUME: 11
        (E) ISSUE: 5
        (F) PAGES: 2656-2664
        (G) DATE: 1991

(x) PUBLICATION INFORMATION:
        (A) AUTHORS: Patient, R. K.
            Harris, R.
            Walmsley, M. E.
            Williams, J. G.
        (C) JOURNAL: J. Biol. Chem.
        (D) VOLUME: 258

(F) PAGES: 8521-8523
                (G) DATE: 1983

(xi) SEQUENCE DESCRIPTION: SEQ ID NO: 6:

GGCCGTCGAC GCTTGTTCTT TTTGCAGAAG CTCAGAATAA ACGCTCAACT TTGGC           55

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..17
        (D) OTHER INFORMATION: /label= M1317MER
            /note= "synthetic DNA; M13 sequencing primer
            (New England Biolabs GmbH), utilized for PCR"

(xi) SEQUENCE DESCRIPTION: SEQ ID NO: 7:

GTAAAACGAC GGCCAGT                                                    17

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..24
        (D) OTHER INFORMATION: /label= M1324MER
            /note= "synthetic DNA; M13 reverse
            sequencing primer (New England Biolabs GmbH),
            utilized for PCR"

(xi) SEQUENCE DESCRIPTION: SEQ ID NO: 8:

AGCGGATAAC AATTTCACAC AGGA                                            24

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..19
        (D) OTHER INFORMATION: /label= NCCLSA1
            /note= "synthetic DNA; synthetic linker for
            recloning of the shortened PDGF-B precursor
            from pMVW-2 in bacteriophage M13mp19"

(xi) SEQUENCE DESCRIPTION: SEQ ID NO: 9:

CATGGCCCAA TCGATCCCG                                                  19

(2) INFORMATION FOR SEQ ID NO: 10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ix) FEATURE:

(A) NAME/KEY: -
            (B) LOCATION: 1..19
            (D) OTHER INFORMATION: /label= NCCLSA2
                /note= "synthetic DNA; synthetic linker for
                recloning of the shortened PDGF-B precursor
                from pMVW-2 in bacteriophage M13mp19"

(xi) SEQUENCE DESCRIPTION: SEQ ID NO: 10:

TCGACGGGAT CGATTGGGC                                                19

(2) INFORMATION FOR SEQ ID NO: 11:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
         (A) NAME/KEY: -
         (B) LOCATION: 1..37
         (D) OTHER INFORMATION: /label= PDGBBCL
             /note= "synthetic DNA; mutagenesis primer for
             the insertion of a BclI-cleavage site into the
             5'-region of the PDGF-B precursor"

(xi) SEQUENCE DESCRIPTION: SEQ ID NO: 11:

GCTTTATGAG ATGCTGAGTG ATCACTCGAT CCGCTCC                             37

(2) INFORMATION FOR SEQ ID NO: 12:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ix) FEATURE:
         (A) NAME/KEY: -
         (B) LOCATION: 1..110
         (D) OTHER INFORMATION: /label= PPDGFB1
             /note= "synthetic DNA; synthetic linker for
             reconstitution of the mature PDGF-B
             precursor sequence"

(xi) SEQUENCE DESCRIPTION: SEQ ID NO: 12:

TCGACACCAT GAATCGCTGC TGGGCGCTCT TCCTGTCTCT CTGCTGCTAC CTGCGTCTGG    60

TCAGCGCCGA GGGGGACCCC ATTCCCGAGG AGCTTTATGA GATGCTGAGT             110

(2) INFORMATION FOR SEQ ID NO: 13:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ix) FEATURE:
         (A) NAME/KEY: -
         (B) LOCATION: 1..110
         (D) OTHER INFORMATION: /label= PPDGFB2
             /note= "synthetic DNA; synthetic linker for
             reconstitution of the mature PDGF-B
             precursor sequence"

(xi) SEQUENCE DESCRIPTION: SEQ ID NO: 13:

GATCACTCAG CATCTCATAA AGCTCCTCGG GAATGGGGTC CCCCTCGGCG CTGACCAGAC    60

GCAGGTAGCA GCAGAGAGAC AGGAAGAGCG CCCAGCAGCG ATTCATGGTG             110

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..30
        (D) OTHER INFORMATION: /label= 5'-POLIO1
            /note= "synthetic DNA; synthetic
            PCR primer"

(xi) SEQUENCE DESCRIPTION: SEQ ID NO: 14:

TTTCTGCAGA AGCTTAAAAC AGCTCTGGGG                                30

(2) INFORMATION FOR SEQ ID NO: 15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..28
        (D) OTHER INFORMATION: /label= 3'-POLIO2
            /note= "synthetic DNA; synthetic
            PCR primer"

(xi) SEQUENCE DESCRIPTION: SEQ ID NO: 15:

TTGCGGCCGC AATCCAATTC GCTTTATC                                    28

(2) INFORMATION FOR SEQ ID NO: 16:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..13
        (D) OTHER INFORMATION: /label= E-N-E1
            /note= "synthetic DNA; synthetic linker"

(xi) SEQUENCE DESCRIPTION: SEQ ID NO: 16:

AATTGCGGCC GCG                                                       13

(2) INFORMATION FOR SEQ ID NO: 17:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ix) FEATURE:
        (A) NAME/KEY: -
        (B) LOCATION: 1..13
        (D) OTHER INFORMATION: /label= E-N-E2
            /note= "synthetic DNA; synthetic linker"

(xi) SEQUENCE DESCRIPTION: SEQ ID NO: 17:

AATTCGCGGC CGC                                                         13

(2) INFORMATION FOR SEQ ID NO: 18:

```
        (i) SEQUENCE CHARACTERISTICS:
            (A) LENGTH: 19 base pairs
            (B) TYPE: nucleic acid
            (C) STRANDEDNESS: single
            (D) TOPOLOGY: linear (ix) FEATURE:
            (A) NAME/KEY: -
            (B) LOCATION: 1..16
            (D) OTHER INFORMATION: /label= PDGFB190-PRIMI
                /note= "synthetic DNA; synthetic PCR primer"

(xi) SEQUENCE DESCRIPTION: SEQ ID NO: 18:

GAATTCGAGC TCGCCCGGG                                                      19

(2) INFORMATION FOR SEQ ID NO: 19:

(i) SEQUENCE CHARACTERISTICS:
            (A) LENGTH: 37 base pairs
            (B) TYPE: nucleic acid
            (C) STRANDEDNESS: single
            (D) TOPOLOGY: linear (ix) FEATURE:
            (A) NAME/KEY: -
            (B) LOCATION: 1..37
            (D) OTHER INFORMATION: /label= PDGFB190-PRIMII
                /note= "synthetic DNA; synthetic PCR primer"

(xi) SEQUENCE DESCRIPTION: SEQ ID NO: 19:

CCCGGGAAGC TTCCGGTTAT CAGGTCACAG GCCGTGC                                  37

(2) INFORMATION FOR SEQ ID NO: 20:

(i) SEQUENCE CHARACTERISTICS:
            (A) LENGTH: 1956 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens (vii) IMMEDIATE SOURCE:
            (B) CLONE: pSQ2-SEAP (Berger et al., 1988)

(ix) FEATURE:
            (A) NAME/KEY: CDS
            (B) LOCATION: 43..1560
            (D) OTHER INFORMATION: /note= "human SEAP gene; flanked
                by 5'-EcoRI and 3'-HindIII restriction cleavage
                sites"

(ix) FEATURE:
            (A) NAME/KEY: mat_peptide
            (B) LOCATION: 94..1560
            (D) OTHER INFORMATION: /product= "mature protein"

(x) PUBLICATION INFORMATION:
            (A) AUTHORS: Berger, J.
                Hauber, J.
                Hauber, R.
                Geiger, R.
                Cullen, B. R.
            (C) JOURNAL: Gene
            (D) VOLUME: 66
            (F) PAGES: 1-10
            (G) DATE: 1988

(x) PUBLICATION INFORMATION:
            (A) AUTHORS: Millan, J. L.
            (C) JOURNAL: J. Biol. Chem.
```

(D) VOLUME: 261
(F) PAGES: 3112-3115
(G) DATE: 1986

(xi) SEQUENCE DESCRIPTION: SEQ ID NO: 20:

```
GAATTCGAGC TCGCCCGGGG ATCCTCTAGA GTCAGCTTCT GC ATG CTG CTG CTG              54
                                                Met Leu Leu Leu
                                                -17      -15

CTG CTG CTG CTG GGC CTG AGG CTA CAG CTC TCC CTG GGC ATC ATC CCA            102
Leu Leu Leu Leu Gly Leu Arg Leu Gln Leu Ser Leu Gly Ile Ile Pro
            -10              -5                      1

GTT GAG GAG GAG AAC CCG GAC TTC TGG AAC CGC GAG GCA GCC GAG GCC            150
Val Glu Glu Glu Asn Pro Asp Phe Trp Asn Arg Glu Ala Ala Glu Ala
         5                  10              15

CTG GGT GCC GCC AAG AAG CTG CAG CCT GCA CAG ACA GCC GCC AAG AAC            198
Leu Gly Ala Ala Lys Lys Leu Gln Pro Ala Gln Thr Ala Ala Lys Asn
 20              25                  30                      35

CTC ATC ATC TTC CTG GGC GAT GGG ATG GGG GTG TCT ACG GTG ACA GCT            246
Leu Ile Ile Phe Leu Gly Asp Gly Met Gly Val Ser Thr Val Thr Ala
             40                  45                  50

GCC AGG ATC CTA AAA GGG CAG AAG AAG GAC AAA CTG GGG CCT GAG ATA            294
Ala Arg Ile Leu Lys Gly Gln Lys Lys Asp Lys Leu Gly Pro Glu Ile
             55                  60                  65

CCC CTG GCC ATG GAC CGC TTC CCA TAT GTG GCT CTG TCC AAG ACA TAC            342
Pro Leu Ala Met Asp Arg Phe Pro Tyr Val Ala Leu Ser Lys Thr Tyr
         70                  75                  80

AAT GTA GAC AAA CAT GTG CCA GAC AGT GGA GCC ACA GCC ACG GCC TAC            390
Asn Val Asp Lys His Val Pro Asp Ser Gly Ala Thr Ala Thr Ala Tyr
         85                  90                  95

CTG TGC GGG GTC AAG GGC AAC TTC CAG ACC ATT GGC TTG AGT GCA GCC            438
Leu Cys Gly Val Lys Gly Asn Phe Gln Thr Ile Gly Leu Ser Ala Ala
100             105                 110                     115

GCC CGC TTT AAC CAG TGC AAC ACG ACA CGC GGC AAC GAG GTC ATC TCC            486
Ala Arg Phe Asn Gln Cys Asn Thr Thr Arg Gly Asn Glu Val Ile Ser
                120                 125                 130

GTG ATG AAT CGG GCC AAG AAA GCA GGG AAG TCA GTG GGA GTG GTA ACC            534
Val Met Asn Arg Ala Lys Lys Ala Gly Lys Ser Val Gly Val Val Thr
            135                 140                 145

ACC ACA CGA GTG CAG CAC GCC TCG CCA GCC GGC ACC TAC GCC CAC ACG            582
Thr Thr Arg Val Gln His Ala Ser Pro Ala Gly Thr Tyr Ala His Thr
            150                 155                 160

GTG AAC CGC AAC TGG TAC TCG GAC GCC GAC GTG CCT GCC TCG GCC CGC            630
Val Asn Arg Asn Trp Tyr Ser Asp Ala Asp Val Pro Ala Ser Ala Arg
            165                 170                 175

CAG GAG GGG TGC CAG GAC ATC GCT ACG CAG CTC ATC TCC AAC ATG GAC            678
Gln Glu Gly Cys Gln Asp Ile Ala Thr Gln Leu Ile Ser Asn Met Asp
180             185                 190                 195

ATT GAC GTG ATC CTA GGT GGA GGC CGA AAG TAC ATG TTT CCC ATG GGA            726
Ile Asp Val Ile Leu Gly Gly Gly Arg Lys Tyr Met Phe Pro Met Gly
                200                 205                 210

ACC CCA GAC CCT GAG TAC CCA GAT GAC TAC AGC CAA GGT GGG ACC AGG            774
Thr Pro Asp Pro Glu Tyr Pro Asp Asp Tyr Ser Gln Gly Gly Thr Arg
                215                 220                 225

CTG GAC GGG AAG AAT CTG GTG CAG GAA TGG CTG GCG AAG CGC CAG GGT            822
Leu Asp Gly Lys Asn Leu Val Gln Glu Trp Leu Ala Lys Arg Gln Gly
            230                 235                 240

GCC CGG TAT GTG TGG AAC CGC ACT GAG CTC ATG CAG GCT TCC CTG GAC            870
Ala Arg Tyr Val Trp Asn Arg Thr Glu Leu Met Gln Ala Ser Leu Asp
            245                 250                 255

CCG TCT GTG ACC CAT CTC ATG GGT CTC TTT GAG CCT GGA GAC ATG AAA            918
```

```
Pro Ser Val Thr His Leu Met Gly Leu Phe Glu Pro Gly Asp Met Lys
260                 265                 270                 275

TAC GAG ATC CAC CGA GAC TCC ACA CTG GAC CCC TCC CTG ATG GAG ATG      966
Tyr Glu Ile His Arg Asp Ser Thr Leu Asp Pro Ser Leu Met Glu Met
                    280                 285                 290

ACA GAG GCT GCC CTG CGC CTG CTG AGC AGG AAC CCC CGC GGC TTC TTC     1014
Thr Glu Ala Ala Leu Arg Leu Leu Ser Arg Asn Pro Arg Gly Phe Phe
                295                 300                 305

CTC TTC GTG GAG GGT GGT CGC ATC GAC CAT GGT CAT CAT GAA AGC AGG     1062
Leu Phe Val Glu Gly Gly Arg Ile Asp His Gly His His Glu Ser Arg
            310                 315                 320

GCT TAC CGG GCA CTG ACT GAG ACG ATC ATG TTC GAC GAC GCC ATT GAG     1110
Ala Tyr Arg Ala Leu Thr Glu Thr Ile Met Phe Asp Asp Ala Ile Glu
        325                 330                 335

AGG GCG GGC CAG CTC ACC AGC GAG GAG GAC ACG CTG AGC CTC GTC ACT     1158
Arg Ala Gly Gln Leu Thr Ser Glu Glu Asp Thr Leu Ser Leu Val Thr
340                 345                 350                 355

GCC GAC CAC TCC CAC GTC TTC TCC TTC GGA GGC TAC CCC CTG CGA GGG     1206
Ala Asp His Ser His Val Phe Ser Phe Gly Gly Tyr Pro Leu Arg Gly
                360                 365                 370

AGC TCC ATC TTC GGG CTG GCC CCT GGC AAG GCC CGG GAC AGG AAG GCC     1254
Ser Ser Ile Phe Gly Leu Ala Pro Gly Lys Ala Arg Asp Arg Lys Ala
            375                 380                 385

TAC ACG GTC CTC CTA TAC GGA AAC GGT CCA GGC TAT GTG CTC AAG GAC     1302
Tyr Thr Val Leu Leu Tyr Gly Asn Gly Pro Gly Tyr Val Leu Lys Asp
        390                 395                 400

GGC GCC CGG CCG GAT GTT ACC GAG AGC GAG AGC GGG AGC CCC GAG TAT     1350
Gly Ala Arg Pro Asp Val Thr Glu Ser Glu Ser Gly Ser Pro Glu Tyr
405                 410                 415

CGG CAG CAG TCA GCA GTG CCC CTG GAC GAA GAG ACC CAC GCA GGC GAG     1398
Arg Gln Gln Ser Ala Val Pro Leu Asp Glu Glu Thr His Ala Gly Glu
420                 425                 430                 435

GAC GTG GCG GTG TTC GCG CGC GGC CCG CAG GCG CAC CTG GTT CAC GGC     1446
Asp Val Ala Val Phe Ala Arg Gly Pro Gln Ala His Leu Val His Gly
                440                 445                 450

GTG CAG GAG CAG ACC TTC ATA GCG CAC GTC ATG GCC TTC GCC GCC TGC     1494
Val Gln Glu Gln Thr Phe Ile Ala His Val Met Ala Phe Ala Ala Cys
            455                 460                 465

CTG GAG CCC TAC ACC GCC TGC GAC CTG GCG CCC CCC GCC GGC ACC ACC     1542
Leu Glu Pro Tyr Thr Ala Cys Asp Leu Ala Pro Pro Ala Gly Thr Thr
        470                 475                 480

GAC GCC GCG CAC CCG GGT TAACCCGTGG TCCCCGCGTT GCTTCCTCTG            1590
Asp Ala Ala His Pro Gly
        485

CTGGCCGGGA CCCTGCTGCT GCTGGAGACG GCCACTGCTC CCTGAGTGTC CCGTCCCTGG   1650

GGCTCCTGCT TCCCCATCCC GGAGTTCTCC TGCTCCCCAC CTCCTGTCGT CCTGCCTGGC   1710

CTCCAGCCCG AGTCGTCATC CCCGGAGTCC CTATACAGAG GTCCTGCCAT GGAACCTTCC   1770

CCTCCCCGTG CGCTCTGGGG ACTGAGCCCA TGACACCAAA CCTGCCCCTT GGCTGCTCTC   1830

GGACTCCCTA CCCCAACCCC AGGGACTGCA GGTTGTGCCC TGTGGCTGCC TGCACCCCAG   1890

GAAAGGAGGG GGCTCAGGCC ATCCAGCCAC CACCTACAGC CCAGTGGCCT CGAGCTGCAG   1950

AAGCTT                                                              1956

(2) INFORMATION FOR SEQ ID NO: 21:

(i) SEQUENCE CHARACTERISTICS:
        (A) LENGTH: 506 amino acids
        (B) TYPE: amino acid
```

(D) TOPOLOGY: linear (ii) MOLECULE TYPE: protein (xi) SEQUENCE DESCRIPTION: SEQ ID NO: 21:

```
Met Leu Leu Leu Leu Leu Leu Gly Leu Arg Leu Gln Leu Ser Leu
-17     -15                 -10                 -5
Gly Ile Ile Pro Val Glu Glu Asn Pro Asp Phe Trp Asn Arg Glu
     1               5                  10                 15
Ala Ala Glu Ala Leu Gly Ala Ala Lys Lys Leu Gln Pro Ala Gln Thr
                 20              25                  30
Ala Ala Lys Asn Leu Ile Ile Phe Leu Gly Asp Gly Met Gly Val Ser
             35                  40                  45
Thr Val Thr Ala Ala Arg Ile Leu Lys Gly Gln Lys Lys Asp Lys Leu
         50                  55                  60
Gly Pro Glu Ile Pro Leu Ala Met Asp Arg Phe Pro Tyr Val Ala Leu
     65                  70                  75
Ser Lys Thr Tyr Asn Val Asp Lys His Val Pro Asp Ser Gly Ala Thr
 80                  85                  90                  95
Ala Thr Ala Tyr Leu Cys Gly Val Lys Gly Asn Phe Gln Thr Ile Gly
                100                 105                 110
Leu Ser Ala Ala Ala Arg Phe Asn Gln Cys Asn Thr Thr Arg Gly Asn
                115                 120                 125
Glu Val Ile Ser Val Met Asn Arg Ala Lys Lys Ala Gly Lys Ser Val
            130                 135                 140
Gly Val Val Thr Thr Thr Arg Val Gln His Ala Ser Pro Ala Gly Thr
    145                 150                 155
Tyr Ala His Thr Val Asn Arg Asn Trp Tyr Ser Asp Ala Asp Val Pro
160                 165                 170                 175
Ala Ser Ala Arg Gln Glu Gly Cys Gln Asp Ile Ala Thr Gln Leu Ile
                180                 185                 190
Ser Asn Met Asp Ile Asp Val Ile Leu Gly Gly Gly Arg Lys Tyr Met
            195                 200                 205
Phe Pro Met Gly Thr Pro Asp Pro Glu Tyr Pro Asp Asp Tyr Ser Gln
        210                 215                 220
Gly Gly Thr Arg Leu Asp Gly Lys Asn Leu Val Gln Glu Trp Leu Ala
225                 230                 235
Lys Arg Gln Gly Ala Arg Tyr Val Trp Asn Arg Thr Glu Leu Met Gln
240                 245                 250                 255
Ala Ser Leu Asp Pro Ser Val Thr His Leu Met Gly Leu Phe Glu Pro
            260                 265                 270
Gly Asp Met Lys Tyr Glu Ile His Arg Asp Ser Thr Leu Asp Pro Ser
        275                 280                 285
Leu Met Glu Met Thr Glu Ala Ala Leu Arg Leu Leu Ser Arg Asn Pro
    290                 295                 300
Arg Gly Phe Phe Leu Phe Val Glu Gly Gly Arg Ile Asp His Gly His
    305                 310                 315
His Glu Ser Arg Ala Tyr Arg Ala Leu Thr Glu Thr Ile Met Phe Asp
320                 325                 330                 335
Asp Ala Ile Glu Arg Ala Gly Gln Leu Thr Ser Glu Glu Asp Thr Leu
            340                 345                 350
Ser Leu Val Thr Ala Asp His Ser His Val Phe Ser Phe Gly Gly Tyr
        355                 360                 365
Pro Leu Arg Gly Ser Ser Ile Phe Gly Leu Ala Pro Gly Lys Ala Arg
```

```
              370                 375                 380
Asp Arg Lys Ala Tyr Thr Val Leu Leu Tyr Gly Asn Gly Pro Gly Tyr
385                 390                 395

Val Leu Lys Asp Gly Ala Arg Pro Asp Val Thr Glu Ser Glu Ser Gly
400                 405                 410                 415

Ser Pro Glu Tyr Arg Gln Gln Ser Ala Val Pro Leu Asp Glu Thr
                    420                 425                 430

His Ala Gly Glu Asp Val Ala Val Phe Ala Arg Gly Pro Gln Ala His
                435                 440                 445

Leu Val His Gly Val Gln Glu Gln Thr Phe Ile Ala His Val Met Ala
            450                 455                 460

Phe Ala Ala Cys Leu Glu Pro Tyr Thr Ala Cys Asp Leu Ala Pro Pro
        465                 470                 475

Ala Gly Thr Thr Asp Ala Ala His Pro Gly
480                 485
```

(2) INFORMATION FOR SEQ ID NO: 22:

(i) SEQUENCE CHARACTERISTICS:
        (A) LENGTH: 1811 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: fire fly (Photinus pyralis)

(vii) IMMEDIATE SOURCE:
        (B) CLONE: pRSVLUC (de Wet et al., 1987)

(ix) FEATURE:
        (A) NAME/KEY: CDS
        (B) LOCATION: 94..1743
        (D) OTHER INFORMATION: /note= "coding region of the
            luciferase gene; flanked by 5'-SmaI and
            3'-HindIII restriction cleavage sites"

(x) PUBLICATION INFORMATION:
        (A) AUTHORS: de Wet, J. R.
            Wood, K. V.
            DeLuca, M.
            Helinski, D. R.
            Subramani, S.
        (C) JOURNAL: Mol. Cell. Biol.
        (D) VOLUME: 7
        (F) PAGES: 725-737
        (G) DATE: 1987

(xi) SEQUENCE DESCRIPTION: SEQ ID NO: 22:

```
CCCGGGGATC CTCTAGAGTC AGCTTGAATT CCTTTGTGTT ACATTCTTGA ATGTCGCTCG        60

CAGTGACATT AGCATTCCGG TACTGTTGGT AAA ATG GAA GAC GCC AAA AAC ATA       114
                                   Met Glu Asp Ala Lys Asn Ile
                                     1               5

AAG AAA GGC CCG GCG CCA TTC TAT CCT CTA GAG GAT GGA ACC GCT GGA        162
Lys Lys Gly Pro Ala Pro Phe Tyr Pro Leu Glu Asp Gly Thr Ala Gly
         10                  15                  20

GAG CAA CTG CAT AAG GCT ATG AAG AGA TAC GCC CTG GTT CCT GGA ACA        210
Glu Gln Leu His Lys Ala Met Lys Arg Tyr Ala Leu Val Pro Gly Thr
     25                  30                  35

ATT GCT TTT ACA GAT GCA CAT ATC GAG GTG AAC ATC ACG TAC GCG GAA        258
Ile Ala Phe Thr Asp Ala His Ile Glu Val Asn Ile Thr Tyr Ala Glu
 40                  45                  50                  55

TAC TTC GAA ATG TCC GTT CGG TTG GCA GAA GCT ATG AAA CGA TAT GGG        306
```

```
                Tyr Phe Glu Met Ser Val Arg Leu Ala Glu Ala Met Lys Arg Tyr Gly
                                60                  65                  70

CTG AAT ACA AAT CAC AGA ATC GTC GTA TGC AGT GAA AAC TCT CTT CAA          354
Leu Asn Thr Asn His Arg Ile Val Val Cys Ser Glu Asn Ser Leu Gln
            75                  80                  85

TTC TTT ATG CCG GTG TTG GGC GCG TTA TTT ATC GGA GTT GCA GTT GCG          402
Phe Phe Met Pro Val Leu Gly Ala Leu Phe Ile Gly Val Ala Val Ala
        90                  95                  100

CCC GCG AAC GAC ATT TAT AAT GAA CGT GAA TTG CTC AAC AGT ATG AAC          450
Pro Ala Asn Asp Ile Tyr Asn Glu Arg Glu Leu Leu Asn Ser Met Asn
    105                 110                 115

ATT TCG CAG CCT ACC GTA GTG TTT GTT TCC AAA AAG GGG TTG CAA AAA          498
Ile Ser Gln Pro Thr Val Val Phe Val Ser Lys Lys Gly Leu Gln Lys
120                 125                 130                 135

ATT TTG AAC GTG CAA AAA AAA TTA CCA ATA ATC CAG AAA ATT ATT ATC          546
Ile Leu Asn Val Gln Lys Lys Leu Pro Ile Ile Gln Lys Ile Ile Ile
                140                 145                 150

ATG GAT TCT AAA ACG GAT TAC CAG GGA TTT CAG TCG ATG TAC ACG TTC          594
Met Asp Ser Lys Thr Asp Tyr Gln Gly Phe Gln Ser Met Tyr Thr Phe
            155                 160                 165

GTC ACA TCT CAT CTA CCT CCC GGT TTT AAT GAA TAC GAT TTT GTA CCA          642
Val Thr Ser His Leu Pro Pro Gly Phe Asn Glu Tyr Asp Phe Val Pro
        170                 175                 180

GAG TCC TTT GAT CGT GAC AAA ACA ATT GCA CTG ATA ATG AAT TCC TCT          690
Glu Ser Phe Asp Arg Asp Lys Thr Ile Ala Leu Ile Met Asn Ser Ser
    185                 190                 195

GGA TCT ACT GGG TTA CCT AAG GGT GTG GCC CTT CCG CAT AGA ACT GCC          738
Gly Ser Thr Gly Leu Pro Lys Gly Val Ala Leu Pro His Arg Thr Ala
200                 205                 210                 215

TGC GTC AGA TTC TCG CAT GCC AGA GAT CCT ATT TTT GGC AAT CAA ATC          786
Cys Val Arg Phe Ser His Ala Arg Asp Pro Ile Phe Gly Asn Gln Ile
                220                 225                 230

ATT CCG GAT ACT GCG ATT TTA AGT GTT GTT CCA TTC CAT CAC GGT TTT          834
Ile Pro Asp Thr Ala Ile Leu Ser Val Val Pro Phe His His Gly Phe
            235                 240                 245

GGA ATG TTT ACT ACA CTC GGA TAT TTG ATA TGT GGA TTT CGA GTC GTC          882
Gly Met Phe Thr Thr Leu Gly Tyr Leu Ile Cys Gly Phe Arg Val Val
        250                 255                 260

TTA ATG TAT AGA TTT GAA GAA GAG CTG TTT TTA CGA TCC CTT CAG GAT          930
Leu Met Tyr Arg Phe Glu Glu Glu Leu Phe Leu Arg Ser Leu Gln Asp
    265                 270                 275

TAC AAA ATT CAA AGT GCG TTG CTA GTA CCA ACC CTA TTT TCA TTC TTC          978
Tyr Lys Ile Gln Ser Ala Leu Leu Val Pro Thr Leu Phe Ser Phe Phe
280                 285                 290                 295

GCC AAA AGC ACT CTG ATT GAC AAA TAC GAT TTA TCT AAT TTA CAC GAA          1026
Ala Lys Ser Thr Leu Ile Asp Lys Tyr Asp Leu Ser Asn Leu His Glu
                300                 305                 310

ATT GCT TCT GGG GGC GCA CCT CTT TCG AAA GAA GTC GGG GAA GCG GTT          1074
Ile Ala Ser Gly Gly Ala Pro Leu Ser Lys Glu Val Gly Glu Ala Val
            315                 320                 325

GCA AAA CGC TTC CAT CTT CCA GGG ATA CGA CAA GGA TAT GGG CTC ACT          1122
Ala Lys Arg Phe His Leu Pro Gly Ile Arg Gln Gly Tyr Gly Leu Thr
        330                 335                 340

GAG ACT ACA TCA GCT ATT CTG ATT ACA CCC GAG GGG GAT GAT AAA CCG          1170
Glu Thr Thr Ser Ala Ile Leu Ile Thr Pro Glu Gly Asp Asp Lys Pro
    345                 350                 355

GGC GCG GTC GGT AAA GTT GTT CCA TTT TTT GAA GCG AAG GTT GTG GAT          1218
Gly Ala Val Gly Lys Val Val Pro Phe Phe Glu Ala Lys Val Val Asp
360                 365                 370                 375
```

-continued

```
CTG GAT ACC GGG AAA ACG CTG GGC GTT AAT CAG AGA GGC GAA TTA TGT      1266
Leu Asp Thr Gly Lys Thr Leu Gly Val Asn Gln Arg Gly Glu Leu Cys
            380                 385                 390

GTC AGA GGA CCT ATG ATT ATG TCC GGT TAT GTA AAC AAT CCG GAA GCG      1314
Val Arg Gly Pro Met Ile Met Ser Gly Tyr Val Asn Asn Pro Glu Ala
                395                 400                 405

ACC AAC GCC TTG ATT GAC AAG GAT GGA TGG CTA CAT TCT GGA GAC ATA      1362
Thr Asn Ala Leu Ile Asp Lys Asp Gly Trp Leu His Ser Gly Asp Ile
            410                 415                 420

GCT TAC TGG GAC GAA GAC GAA CAC TTC TTC ATA GTT GAC CGC TTG AAG      1410
Ala Tyr Trp Asp Glu Asp Glu His Phe Phe Ile Val Asp Arg Leu Lys
                425                 430                 435

TCT TTA ATT AAA TAC AAA GGA TAT CAG GTG GCC CCC GCT GAA TTG GAA      1458
Ser Leu Ile Lys Tyr Lys Gly Tyr Gln Val Ala Pro Ala Glu Leu Glu
440                 445                 450                 455

TCG ATA TTG TTA CAA CAC CCC AAC ATC TTC GAC GCG GGC GTG GCA GGT      1506
Ser Ile Leu Leu Gln His Pro Asn Ile Phe Asp Ala Gly Val Ala Gly
                    460                 465                 470

CTT CCC GAC GAT GAC GCC GGT GAA CTT CCC GCC GCC GTT GTT GTT TTG      1554
Leu Pro Asp Asp Asp Ala Gly Glu Leu Pro Ala Ala Val Val Val Leu
                475                 480                 485

GAG CAC GGA AAG ACG ATG ACG GAA AAA GAG ATC GTG GAT TAC GTC GCC      1602
Glu His Gly Lys Thr Met Thr Glu Lys Glu Ile Val Asp Tyr Val Ala
            490                 495                 500

AGT CAA GTA ACA ACC GCG AAA AAG TTG CGC GGA GGA GTT GTG TTT GTG      1650
Ser Gln Val Thr Thr Ala Lys Lys Leu Arg Gly Gly Val Val Phe Val
505                 510                 515

GAC GAA GTA CCG AAA GGT CTT ACC GGA AAA CTC GAC GCA AGA AAA ATC      1698
Asp Glu Val Pro Lys Gly Leu Thr Gly Lys Leu Asp Ala Arg Lys Ile
520                 525                 530                 535

AGA GAG ATC CTC ATA AAG GCC AAG AAG GGC GGA AAG TCC AAA TTG          1743
Arg Glu Ile Leu Ile Lys Ala Lys Lys Gly Gly Lys Ser Lys Leu
                540                 545                 550

TAAAATGTAA CTGTATTCAG CGATGACGAA ATTCTTAGCT ATTGTAATAG CTGCAGGCAT    1803

GCAAGCTT                                                             1811
```

(2) INFORMATION FOR SEQ ID NO: 23:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO: 23:

```
Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
```

-continued

```
                100             105             110
Glu Leu Leu Asn Ser Met Asn Ile Ser Gln Pro Thr Val Phe Val
            115             120             125
Ser Lys Lys Gly Leu Gln Lys Ile Leu Asn Val Gln Lys Lys Leu Pro
130             135             140
Ile Ile Gln Lys Ile Ile Ile Met Asp Ser Lys Thr Asp Tyr Gln Gly
145             150             155             160
Phe Gln Ser Met Tyr Thr Phe Val Thr Ser His Leu Pro Pro Gly Phe
                165             170             175
Asn Glu Tyr Asp Phe Val Pro Glu Ser Phe Asp Arg Asp Lys Thr Ile
            180             185             190
Ala Leu Ile Met Asn Ser Ser Gly Ser Thr Gly Leu Pro Lys Gly Val
            195             200             205
Ala Leu Pro His Arg Thr Ala Cys Val Arg Phe Ser His Ala Arg Asp
210             215             220
Pro Ile Phe Gly Asn Gln Ile Ile Pro Asp Thr Ala Ile Leu Ser Val
225             230             235             240
Val Pro Phe His His Gly Phe Gly Met Phe Thr Thr Leu Gly Tyr Leu
            245             250             255
Ile Cys Gly Phe Arg Val Val Leu Met Tyr Arg Phe Glu Glu Glu Leu
            260             265             270
Phe Leu Arg Ser Leu Gln Asp Tyr Lys Ile Gln Ser Ala Leu Leu Val
            275             280             285
Pro Thr Leu Phe Ser Phe Phe Ala Lys Ser Thr Leu Ile Asp Lys Tyr
            290             295             300
Asp Leu Ser Asn Leu His Glu Ile Ala Ser Gly Gly Ala Pro Leu Ser
305             310             315             320
Lys Glu Val Gly Glu Ala Val Ala Lys Arg Phe His Leu Pro Gly Ile
            325             330             335
Arg Gln Gly Tyr Gly Leu Thr Glu Thr Thr Ser Ala Ile Leu Ile Thr
            340             345             350
Pro Glu Gly Asp Asp Lys Pro Gly Ala Val Gly Lys Val Val Pro Phe
            355             360             365
Phe Glu Ala Lys Val Val Asp Leu Asp Thr Gly Lys Thr Leu Gly Val
            370             375             380
Asn Gln Arg Gly Glu Leu Cys Val Arg Gly Pro Met Ile Met Ser Gly
385             390             395             400
Tyr Val Asn Asn Pro Glu Ala Thr Asn Ala Leu Ile Asp Lys Asp Gly
                405             410             415
Trp Leu His Ser Gly Asp Ile Ala Tyr Trp Asp Glu Asp Glu His Phe
            420             425             430
Phe Ile Val Asp Arg Leu Lys Ser Leu Ile Lys Tyr Lys Gly Tyr Gln
            435             440             445
Val Ala Pro Ala Glu Leu Glu Ser Ile Leu Leu Gln His Pro Asn Ile
450             455             460
Phe Asp Ala Gly Val Ala Gly Leu Pro Asp Asp Ala Gly Glu Leu
465             470             475             480
Pro Ala Ala Val Val Val Leu Glu His Gly Lys Thr Met Thr Glu Lys
            485             490             495
Glu Ile Val Asp Tyr Val Ala Ser Gln Val Thr Thr Ala Lys Lys Leu
            500             505             510
Arg Gly Gly Val Val Phe Val Asp Glu Val Pro Lys Gly Leu Thr Gly
            515             520             525
```

Lys Leu Asp Ala Arg Lys Ile Arg Glu Ile Leu Ile Lys Ala Lys Lys
    530                 535                 540

Gly Gly Lys Ser Lys Leu
545             550

(2) INFORMATION FOR SEQ ID NO: 24:

(i) SEQUENCE CHARACTERISTICS:
        (A) LENGTH: 625 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: pSBC-1/-2-PDGF-B (ix) FEATURE:
        (A) NAME/KEY: CDS
        (B) LOCATION: 40..609
        (D) OTHER INFORMATION: /product= "PDGF-B
            precursor sequence"

(ix) FEATURE:
        (A) NAME/KEY: mat_peptide
        (B) LOCATION: 283..609
        (D) OTHER INFORMATION: /product= "mature PDGF-B chain"

(xi) SEQUENCE DESCRIPTION: SEQ ID NO: 24:

```
GAATTCGAGC TCGCCCGGGG ATCCTCTAGA GTCGACACC ATG AAT CGC TGC TGG        54
                                           Met Asn Arg Cys Trp
                                           -81 -80

GCG CTC TTC CTG TCT CTC TGC TGC TAC CTG CGT CTG GTC AGC GCC GAG      102
Ala Leu Phe Leu Ser Leu Cys Cys Tyr Leu Arg Leu Val Ser Ala Glu
    -75             -70             -65

GGG GAC CCC ATT CCC GAG GAG CTT TAT GAG ATG CTG AGT GAT CAC TCG      150
Gly Asp Pro Ile Pro Glu Glu Leu Tyr Glu Met Leu Ser Asp His Ser
-60             -55             -50             -45

ATC CGC TCC TTT GAT GAT CTC CAA CGC CTG CTG CAC GGA GAC CCC GGA      198
Ile Arg Ser Phe Asp Asp Leu Gln Arg Leu Leu His Gly Asp Pro Gly
            -40             -35             -30

GAG GAA GAT GGG GCC GAG TTG GAC CTG AAC ATG ACC CGC TCC CAC TCT      246
Glu Glu Asp Gly Ala Glu Leu Asp Leu Asn Met Thr Arg Ser His Ser
        -25             -20             -15

GGA GGC GAG CTG GAG AGC TTG GCT CGT GGA AGA AGG AGC CTG GGT TCC      294
Gly Gly Glu Leu Glu Ser Leu Ala Arg Gly Arg Arg Ser Leu Gly Ser
    -10              -5                  1

CTG ACC ATT GCT GAG CCG GCC ATG ATC GCC GAG TGC AAG ACG CGC ACC      342
Leu Thr Ile Ala Glu Pro Ala Met Ile Ala Glu Cys Lys Thr Arg Thr
 5              10              15                  20

GAG GTG TTC GAG ATC TCC CGG CGC CTC ATA GAC CGC ACC AAC GCC AAC      390
Glu Val Phe Glu Ile Ser Arg Arg Leu Ile Asp Arg Thr Asn Ala Asn
            25              30              35

TTC CTG GTG TGG CCG CCC TGT GTG GAG GTG CAG CGC TGC TCC GGC TGC      438
Phe Leu Val Trp Pro Pro Cys Val Glu Val Gln Arg Cys Ser Gly Cys
        40              45              50

TGC AAC AAC CGC AAC GTG CAG TGC CGC CCC ACC CAG GTG CAG CTG CGA      486
Cys Asn Asn Arg Asn Val Gln Cys Arg Pro Thr Gln Val Gln Leu Arg
    55              60              65

CCT GTC CAG GTG AGA AAG ATC GAG ATT GTG CGG AAG AAG CCA ATC TTT      534
Pro Val Gln Val Arg Lys Ile Glu Ile Val Arg Lys Lys Pro Ile Phe
```

-continued

```
                    70                    75                    80
AAG AAG GCC ACG GTG ACG CTG GAA GAC CAC CTG GCA TGC AAG TGT GAG        582
Lys Lys Ala Thr Val Thr Leu Glu Asp His Leu Ala Cys Lys Cys Glu
 85                  90                  95                 100

ACA GTG GCA GCT GCA CGG CCT GTG ACC TGATAACCGG AACGTT                  625
Thr Val Ala Ala Ala Arg Pro Val Thr
                    105
```

(2) INFORMATION FOR SEQ ID NO: 25:

(i) SEQUENCE CHARACTERISTICS:
        (A) LENGTH: 190 amino acids
        (B) TYPE: amino acid
        (D) TOPOLOGY: linear (ii) MOLECULE TYPE: protein (xi) SEQUENCE DESCRIPTION: SEQ ID NO: 25:

```
Met Asn Arg Cys Trp Ala Leu Phe Leu Ser Leu Cys Cys Tyr Leu Arg
-81 -80                 -75                 -70

Leu Val Ser Ala Glu Gly Asp Pro Ile Pro Glu Glu Leu Tyr Glu Met
-65                 -60                 -55                 -50

Leu Ser Asp His Ser Ile Arg Ser Phe Asp Asp Leu Gln Arg Leu Leu
                -45                 -40                 -35

His Gly Asp Pro Gly Glu Glu Asp Gly Ala Glu Leu Asp Leu Asn Met
                -30                 -25                 -20

Thr Arg Ser His Ser Gly Gly Glu Leu Glu Ser Leu Ala Arg Gly Arg
                -15                 -10                  -5

Arg Ser Leu Gly Ser Leu Thr Ile Ala Glu Pro Ala Met Ile Ala Glu
  1                   5                  10                  15

Cys Lys Thr Arg Thr Glu Val Phe Glu Ile Ser Arg Arg Leu Ile Asp
                 20                  25                  30

Arg Thr Asn Ala Asn Phe Leu Val Trp Pro Pro Cys Val Glu Val Gln
                 35                  40                  45

Arg Cys Ser Gly Cys Cys Asn Asn Arg Asn Val Gln Cys Arg Pro Thr
                 50                  55                  60

Gln Val Gln Leu Arg Pro Val Gln Val Arg Lys Ile Glu Ile Val Arg
                 65                  70                  75

Lys Lys Pro Ile Phe Lys Lys Ala Thr Val Thr Leu Glu Asp His Leu
 80                  85                  90                  95

Ala Cys Lys Cys Glu Thr Val Ala Ala Ala Arg Pro Val Thr
                100                 105
```